US008178104B2

(12) United States Patent
Ruoslahti et al.

(10) Patent No.: US 8,178,104 B2
(45) Date of Patent: May 15, 2012

(54) METHODS AND COMPOSITIONS FOR TARGETING GC1QR/P32

(75) Inventors: Erkki Ruoslahti, LaJolla, CA (US);
Valentina Fogal, LaJolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 11/777,382

(22) Filed: Jul. 13, 2007

(65) Prior Publication Data

US 2008/0014143 A1  Jan. 17, 2008

Related U.S. Application Data

(60) Provisional application No. 60/807,255, filed on Jul. 13, 2006.

(51) Int. Cl.
*A61K 39/385* (2006.01)

(52) U.S. Cl. .................................................. 424/193.1

(58) Field of Classification Search ........................ None
See application file for complete search history.

(56) References Cited

U.S. PATENT DOCUMENTS

2004/0087499 A1* 5/2004 Laakkonen et al. ............ 514/12

FOREIGN PATENT DOCUMENTS

WO       WO03040693       5/2003

OTHER PUBLICATIONS

Rubinstein et al (Int J. Cancer, 2004, 110: 741-750).*
Alirol, E., and Martinou, J. C. (2006). Mitochondria and cancer: is there a morphological connection? Oncogene 25, 4706-4716.
Alitalo, K., Mohla, S., and Ruoslahti, E. (2004). Lymphangiogenesis and cancer: meeting report. Cancer Res 64, 9225-9229.
Arap, W., Haedicke, W., Bernasconi, M., Kain, R., Rajotte, D., Krajewski, S., Ellerby, H. M., Bredesen, D. E., Pasqualini, R., and Ruoslahti, E. (2002). Targeting the prostate for destruction through,a vascular address. Proc Natl Acad Sci U S A 99, 1527-1531.
Arap, W., Pasqualini, R., and Ruoslahti, E. (1998a). Cancer treatment by targeted drug delivery to tumor vasculature in a mouse model. Science 279, 377-380.
Arap, W., Pasqualini, R., and Ruoslahti, E. (1998b). Chemotherapy targeted to tumor vasculature. Curr Opin Oncol 10, 560-565.
Blancato, J., Singh, B., Liu, A., Liao, D. J., and Dickson, R. B. (2004). Correlation of amplification and overexpression of the c-myc oncogene in high-grade breast cancer: FISH, in situ hybridisation and immunohistochemical analyses. Br J Cancer 90, 1612-1619.
Braun, L., Ghebrehiwet, B., and Cossart, P. (2000). gC1q-R/p32, a C1q-binding protein, is a receptor for the InlB invasion protein of Listeria monocytogenes. Embo J 19, 1458-1466.
Christian, S., Pilch, J., Akerman, M. E., Porkka, K., Laakkonen, P., and Ruoslahti, E. (2003). Nucleolin expressed at the cell surface is a marker of endothelial cells in angiogenic blood vessels. J Cell Biol 163, 871-878.

Deb, T. B., and Datta, K. (1996). Molecular cloning of human fibroblast hyaluronic acid-binding protein confirms its identity with P-32, a protein co-purified with splicing factor SF2. Hyaluronic acid-binding protein as P-32 protein, co-purified with splicing factor SF2. J Biol Chem 271, 2206-2212.
Dedio, J., Jahnen-Dechent, W., Bachmann, M., and Muller-Esterl, W. (1998). The multiligand-binding protein gC1qR, putative C1q receptor, is a mitochondrial protein. J Immunol 160, 3534-3542.
Degenhardt, K., Mathew, R., Beaudoin, B., Bray, K., Anderson, D., Chen, G., Mukherjee, C., Shi, Y., Gelinas, C., Fan, Y., et al. (2006). Autophagy promotes tumor cell survival and restricts necrosis, inflammation, and tumorigenesis. Cancer Cell 10, 51-64.
Effert, P. J., Bares, R., Handt, S., Wolff, J. M., Bull, U., and Jakse, G. (1996). Metabolic imaging of untreated prostate cancer by positron emission tomography with 18fluorine-labeled deoxyglucose. J Urol 155, 994-998.
Fantin, V. R., St-Pierre, J., and Leder, P. (2006). Attenuation of LDH-A expression uncovers a link between glycolysis, mitochondrial physiology, and tumor maintenance. Cancer Cell 9, 425-434.
Garber, K. (2006). Energy deregulation: licensing tumors to grow. Science 312, 1158-1159.
Ghebrehiwet, B., Jesty, J., and Peerschke, E. I. (2002). gC1q-R/p33: structure-function predictions from the crystal structure. Immunobiology 205, 421-432.
Ghebrehiwet, B., Lim, B. L., Peerschke, E. I., Willis, A. C., and Reid, K. B. (1994). Isolation, cDNA cloning, and overexpression of a 33-kD cell surface glycoprotein that binds to the globular "heads" of C1q. J Exp Med 179, 1809-1821.
Ghosh, I., Chowdhury, A. R., Rajeswari, M. R., and Datta, K. (2004). Differential expression of Hyaluronic Acid Binding Protein 1 (HABP1)/P32/C1QBP during progression of epidermal carcinoma. Mol Cell Biochem 267, 133-139.
Guarino, R. D., Dike, L. E., Hag, T. A., Rowley, J. A., Pitner, J. B., and Timmins, M. R. (2004). Method for determining oxygen consumption rates of static cultures from microplate measurements of pericellular dissolved oxygen concentration. Biotechnol Bioeng 86, 775-787.
Guo, W. X., Ghebrehiwet, B., Weksler, B., Schweitzer, K., and Peerschke, E. I. (1999). Up-regulation of endothelial cell binding proteins/receptors for complement component C1q by inflammatory cytokines. J Lab Clin Med 133, 541-550.
Gupta, S., Batchu, R. B., and Datta, K. (1991). Purification, partial characterization of rat kidney hyaluronic acid binding protein and its localization on the cell surface. Eur J Cell Biol 56, 58-67.
Herwald, H., Dedio, J., Kellner, R., Loos, M., and Muller-Esterl, W. (1996). Isolation and characterization of the kininogen-binding protein p33 from endothelial cells. Identity with the gC1q receptor. J Biol Chem 271, 13040-13047.
Hirasawa, A., Awaji, T., Xu, Z., Shinoura, H., and Tsujimoto, G. (2001). Regulation of subcellular localization of alphal-adrenoceptor subtypes. Life Sci 68, 2259-2267.
Hofer, C., Laubenbacher, C., Block, T., Breul, J., Hartung, R., and Schwaiger, M. (1999). Fluorine-18-fluorodeoxyglucose positron emission tomography is useless for the detection of local recurrence after radical prostatectomy. Eur Urol 36, 31-35.
Hoffman, J. A., Giraudo, E., Singh, M., Zhang, L., Inoue, M., Porkka, K., Hanahan, D., and Ruoslahti, E. (2003). Progressive vascular changes in a transgenic mouse model of squamous cell carcinoma. Cancer Cell 4, 383-391.

(Continued)

*Primary Examiner* — Sean Aeder
(74) *Attorney, Agent, or Firm* — Pabst Patent Group LLP

(57) ABSTRACT

Disclosed are compositions and methods useful for targeting gC1q/p32 receptors. The disclosed targeting is useful for delivering therapeutic and detectable agents to cancerous cells, and to areas of inflammation.

13 Claims, 19 Drawing Sheets

OTHER PUBLICATIONS

Figure 1A:
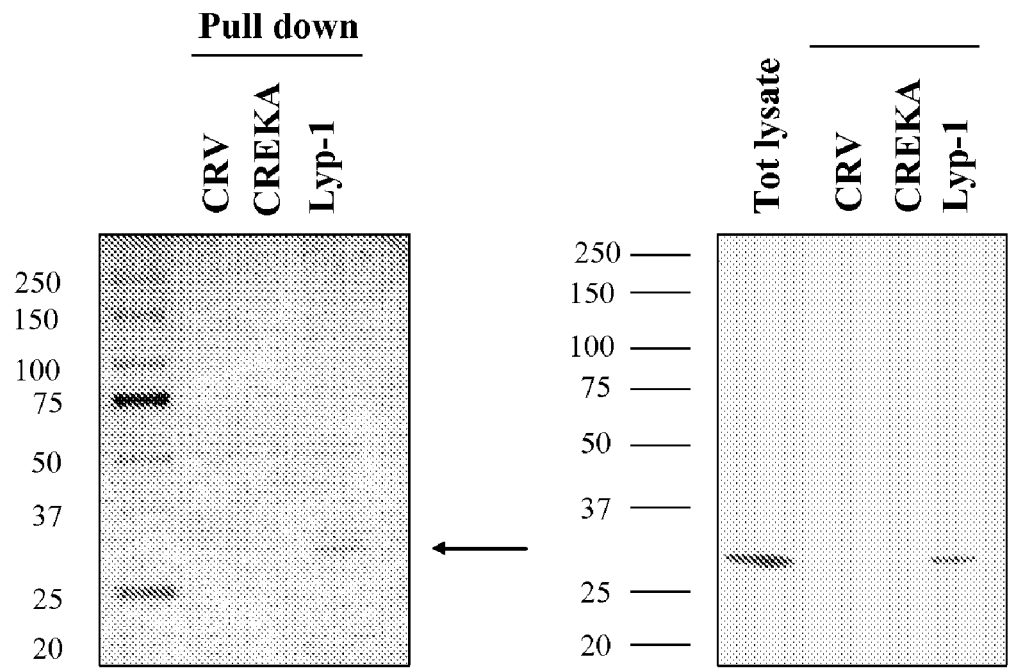

Inoki, K., Zhu, T., and Guan, K. L. (2003). TSC2 mediates cellular energy response to control cell growth and survival. Cell 115, 577-590.

Isidoro, A., Casado, E., Redondo, A., Acebo, P., Espinosa, E., Alonso, A. M., Cejas, P., Hardisson, D., Fresno Vara, J. A., Belda-lniesta, C., et al. (2005). Breast carcinomas fulfill the Warburg hypothesis and provide metabolic markers of cancer prognosis. Carcinogenesis 26, 2095-2104.

Jain, R. K. (1998). The next frontier of molecular medicine: delivery of therapeutics. Nat Med 4, 655-657.

Jiang, J., Zhang, Y., Krainer, A. R., and Xu, R. M. (1999). Crystal structure of human p32, a doughnut-shaped acidic mitochondrial matrix protein. Proc Natl Acad Sci U S A 96, 3572-3577.

Jin, S., DiPaola, R. S., Mathew, R., and White, E. (2007). Metabolic catastrophe as a means to cancer cell death. J Cell Sci 120, 379-383.

Jones, R. G., Plas, D. R., Kubek, S., Buzzai, M., Mu, J., Xu, Y., Birnbaum, M. J., and Thompson, C. B. (2005). AMP-activated protein kinase induces a p53-dependent metabolic checkpoint. Mol Cell 18, 283-293.

Joseph, K., Ghebrehiwet, B., Peerschke, E. I., Reid, K. B., and Kaplan, A. P. (1996). Identification of the zinc-dependent endothelial cell binding protein for high molecular weight kininogen and factor XII: identity with the receptor that binds to the globular "heads" of C1q (gC1q-R). Proc Natl Acad Sci U S A 93, 8552-8557.

Joyce, J. A., Laakkonen, P., Bernasconi, M., Bergers, G., Ruoslahti, E., and Hanahan, D. (2003). Stage-specific vascular markers revealed by phage display in a mouse model of pancreatic islet tumorigenesis. Cancer Cell 4, 393-403.

Kaur, I., Voss, S. D., Gupta, R. S., Schell, K., Fisch, P., and Sondel, P. M. (1993). Human peripheral gamma delta T cells recognize hsp60 molecules on Daudi Burkitt's lymphoma cells. J Immunol 150, 2046-2055.

Kerjaschki, D. (2005). The crucial role of macrophages in lymphangiogenesis. J Clin Invest 115, 2316-2319.

Kerjaschki, D., Huttary, N., Raab, I., Regele, H., Bojarski-Nagy, K., Bartel, G., Krober, S. M., Greinix, H., Rosenmaier, A., Karlhofer, F., et al. (2006). Lymphatic endothelial progenitor cells contribute to de novo lymphangiogenesis in human renal transplants. Nat Med 12, 230-234.

Khan, I. U., Wallin, R., Gupta, R. S., and Kammer, G. M. (1998). Protein kinase A-catalyzed phosphorylation of heat shock protein 60 chaperone regulates its attachment to histone 2B in the T lymphocyte plasma membrane. Proc Natl Acad Sci U S A 95, 10425-10430.

Kittlesen, D. J., Chianese-Bullock, K. A., Yao, Z. Q., Braciale, T. J., and Hahn, Y. S. (2000). Interaction between complement receptor gC1qR and hepatitis C virus core protein inhibits T-lymphocyte proliferation. J Clin Invest 106, 1239-1249.

Krainer, A. R., Mayeda, A., Kozak, D., and Binns, G. (1991). Functional expression of cloned human splicing factor SF2: homology to RNA-binding proteins, U1 70K, and Drosophila splicing regulators. Cell 66, 383-394.

Laakkonen, P., Akerman, M. E., Biliran, H., Yang, M., Ferrer, F., Karpanen, T., Hoffman, R. M., and Ruoslahti, E. (2004). Antitumor activity of a homing peptide that targets tumor lymphatics and tumor cells. Proc Natl Acad Sci U S A 101, 9381-9386.

Laakkonen, P., Porkka, K., Hoffman, J. A., and Ruoslahti, E. (2002). A tumor-homing peptide with a targeting specificity related to lymphatic vessels. Nat Med 8, 751-755.

Lee, S. M., Lee, E. J., Hong, H. Y., Kwon, M. K., Kwon, T. H., Choi, J. Y., Park, R. W., Kwon, T. G., Yoo, E. S., Yoon, G. S., et al. (2007). Targeting bladder tumor cells in vivo and in the urine with a peptide identified by phage display. Mol Cancer Res 5, 11-19.

Levine, B. (2007). Cell biology: autophagy and cancer. Nature 446, 745-747.

Liao, D. J., and Dickson, R. B. (2000). c-Myc in breast cancer. Endocr Relat Cancer 7, 143-164.

Lim, B. L., Reid, K. B., Ghebrehiwet, B., Peerschke, E. I., Leigh, L. A., and Preissner, K. T. (1996). The binding protein for globular heads of complement C1q, gC1qR. Functional expression and characterization as a novel vitronectin binding factor. J Biol Chem 271, 26739-26744.

Liu, Y. (2006). Fatty acid oxidation is a dominant bioenergetic pathway in prostate cancer. Prostate Cancer Prostatic Dis 9, 230-234.

Majumdar, M., Meenakshi, J., Goswami, S. K., and Datta, K. (2002). Hyaluronan binding protein 1 (HABP1)/C1QBP/p32 is an endogenous substrate for MAP kinase and is translocated to the nucleus upon mitogenic stimulation. Biochem Biophys Res Commun 291, 829-837.

Maruyama, K., Asai, J., li, M., Thorne, T., Losordo, D. W., and D'Amore, P. A. (2007). Decreased macrophage number and activation lead to reduced lymphatic vessel formation and contribute to impaired diabetic wound healing. Am J Pathol 170, 1178-1191.

Maruyama, K., li, M., Cursiefen, C., Jackson, D. G., Keino, H., Tomita, M., Van Rooijen, N., Takenaka, H., D'Amore, P. A., Stein-Streilein, J., et al. (2005). Inflammation-induced lymphangiogenesis in the cornea arises from CD11b-positive macrophages. J Clin Invest 115, 2363-2372.

Matthews, D. A., and Russell, W. C. (1998). Adenovirus core protein V interacts with p32—a protein which is associated with both the mitochondria and the nucleus. J Gen Virol 79 ( Pt 7), 1677-1685.

Muta, T., Kang, D., Kitajima, S., Fujiwara, T., and Hamasaki, N. (1997). p32 protein, a splicing factor 2-associated protein, is localized in mitochondrial matrix and is functionally important in maintaining oxidative phosphorylation. J Biol Chem 272, 24363-24370.

Oh, P., Li, Y., Yu, J., Durr, E., Krasinska, K. M., Carver, L. A., Testa, J. E., and Schnitzer, J. E. (2004). Subtractive proteomic mapping of the endothelial surface in lung and solid tumours for tissue-specific therapy. Nature 429, 629-635.

Parle-McDermott, A., McWilliam, P., Tighe, O., Dunican, D., and Croke, D. T. (2000). Serial analysis of gene expression identifies putative metastasis-associated transcripts in colon tumour cell lines. Br J Cancer 83, 725-728.

Peerschke, E. I., Reid, K. B., and Ghebrehiwet, B. (1994). Identification of a novel 33-kDa C1q-binding site on human blood platelets. J Immunol 152, 5896-5901.

Porkka, K., Laakkonen, P., Hoffman, J. A., Bernasconi, M., and Ruoslahti, E. (2002). A fragment of the HMGN2 protein homes to the nuclei of tumor cells and tumor endothelial cells in vivo. Proc Natl Acad Sci U S A 99, 7444-7449.

Reef, S., Shifman, O., Oren, M., and Kimchi, A. (2007). The autophagic inducer smARF interacts with and is stabilized by the mitochondrial p32 protein. Oncogene. Epub.

Robles-Flores, M., Rendon-Huerta, E., Gonzalez-Aguilar, H., Mendoza-Hernandez, G., Islas, S., Mendoza, V., Ponce-Castaneda, M. V., Gonzalez-Mariscal, L., and Lopez-Casillas, F. (2002). p32 (gC1qBP) is a general protein kinase C (PKC)-binding protein; interaction and cellular localization of P32-PKC complexes in ray hepatocytes. J Biol Chem 277, 5247-5255.

Rozanov, D. V., Ghebrehiwet, B., Postnova, T. I., Eichinger, A., Deryugina, E. I., and Strongin, A. Y. (2002a). The hemopexin-like C-terminal domain of membrane type 1 matrix metalloproteinase regulates proteolysis of a multifunctional protein, gC1qR. J Biol Chem 277, 9318-9325.

Rozanov, D. V., Ghebrehiwet, B., Ratnikov, B., Monosov, E. Z., Deryugina, E. I., and Strongin, A. Y. (2002b). The cytoplasmic tail peptide sequence of membrane type-1 matrix metalloproteinase (MT1-MMP) directly binds to gC1qR, a compartment-specific chaperone-like regulatory protein. FEBS Lett 527, 51-57.

Rubinstein, D. B., Stortchevoi, A., Boosalis, M., Ashfaq, R., Ghebrehiwet, B., Peerschke, E. I., Calvo, F., and Guillaume, T. (2004). Receptor for the globular heads of C1q (gC1q-R, p33, hyaluronan-binding protein) is preferentially expressed by adenocarcinoma cells. Int J Cancer 110, 741-750.

Rubinsztein, D. C., Gestwicki, J. E., Murphy, L. O., and Klionsky, D. J. (2007). Potential therapeutic applications of autophagy. Nat Rev Drug Discov 6, 304-312.

Ruoslahti, E. (2002). Specialization of tumour vasculature. Nat Rev Cancer 2, 83-90.

Schaerer, M. T., Kannenberg, K., Hunziker, P., Baumann, S. W., and Sigel, E. (2001). Interaction between GABA(A) receptor beta subunits and the multifunctional protein gC1q-R. J Biol Chem 276, 26597-26604.

Schledzewski, K., Falkowski, M., Moldenhauer, G., Metharom, P., Kzhyshkowska, J., Ganss, R., Demory, A., Falkowska-Hansen, B., Kurzen, H., Ugurel, S., et al. (2006). Lymphatic endothelium-specific hyaluronan receptor LYVE-1 is expressed by stabilin-1+, F4/80+, CD11 b+ macrophages in malignant tumours and wound healing tissue in vivo and in bone marrow cultures in vitro: implications for the assessment of lymphangiogenesis. J Pathol 209, 67-77.

Sengupta, A., Tyagi, R. K., and Datta, K. (2004). Truncated variants of hyaluronan-binding protein 1 bind hyaluronan and induce identical morphological aberrations in COS-1 cells. Biochem J 380, 837-844.

Shaw, R. J. (2006). Glucose metabolism and cancer. Curr Opin Cell Biol 18, 598-608.

Shim, H., Dolde, C., Lewis, B. C., Wu, C. S., Dang, G., Jungmann, R. A., Dalla-Favera, R., and Dang, C. V. (1997). c-Myc transactivation of LDH-A: implications for tumor metabolism and growth. Proc Natl Acad Sci U S A 94, 6658-6663.

Simberg, D., Duza, T., Park, J. H., Essler, M., Pilch, J., Zhang, L., Derfus, A. M., Yang, M., Hoffman, R. M., Bhatia, S., et al. (2007). Biomimetic amplification of nanoparticle homing to tumors. Proc Natl Acad Sci U S A 104, 932-936.

Singh, B., Soltys, B. J., Wu, Z. C., Patel, H. V., Freeman, K. B., and Gupta, R. S. (1997). Cloning and some novel characteristics of mitochondrial Hsp70 from Chinese hamster cells. Exp Cell Res 234, 205-216.

Soltys, B. J., and Gupta, R. S. (1996). Immunoelectron microscopic localization of the 60-kDa heat shock chaperonin protein (Hsp60) in mammalian cells. Exp Cell Res 222, 16-27.

Soltys, B. J., and Gupta, R. S. (1997). Cell surface localization of the 60 kDa heat shock chaperonin protein (hsp60) in mammalian cells. Cell Biol Int 21, 315-320.

Soltys, B. J., and Gupta, R. S. (1999). Mitochondrial-matrix proteins at unexpected locations: are they exported? Trends Biochem Sci 24, 174-177.

Soltys, B. J., Kang, D., and Gupta, R. S. (2000). Localization of P32 protein (gC1 q-R) in mitochondria and at specific extramitochondrial locations in normal tissues. Histochem Cell Biol 114, 245-255.

St Croix, B., Rago, C., Velculescu, V., Traverso, G., Romans, K. E., Montgomery, E., Lal, A., Riggins, G. J., Lengauer, C., Vogelstein, B., and Kinzler, K. W. (2000). Genes expressed in human tumor endothelium. Science 289, 1197-1202.

Stacker, S. A., Achen, M. G., Jussila, L., Baldwin, M. E., and Alitalo, K. (2002). Lymphangiogenesis and cancer metastasis. Nat Rev Cancer 2, 573-583.

Storz, P., Hausser, A., Link, G., Dedio, J., Ghebrehiwet, B., Pfizenmaier, K., and Johannes, F. J. (2000). Protein kinase C [micro] is regulated by the multifunctional chaperon protein p32. J Biol Chem 275, 24601-24607.

Tange, T. O., Jensen, T. H., and Kjems, J. (1996). In vitro interaction between human immunodeficiency virus type 1 Rev protein and splicing factor ASF/SF2-associated protein, p32. J Biol Chem 271, 10066-10072.

van Leeuwen, H. C., and O'Hare, P. (2001). Retargeting of the mitochondrial protein p32/gC1Qr to a cytoplasmic compartment and the cell surface. J Cell Sci 114, 2115-2123.

Wallace, D. C. (2005). Mitochondria and cancer: Warburg addressed. Cold Spring Harb Symp Quant Biol 70, 363-374.

Xu, Q., Schett, G., Seitz, C. S., Hu, Y., Gupta, R. S., and Wick, G. (1994). Surface staining and cytotoxic activity of heat-shock protein 60 antibody in stressed aortic endothelial cells. Circ Res 75, 1078-1085.

Zhang, L., Giraudo, E., Hoffman, J. A., Hanahan, D., and Ruoslahti, E. (2006). Lymphatic zip codes in premalignant lesions and tumors. Cancer Res 66, 5696-5706.

Zhang, Y., Qi, H., Taylor, R., Xu, W., Liu, L. F., and Jin, S. (2007). The Role of Autophagy in Mitochondria Maintenance: Characterization of Mitochondrial Functions in Autophagy-Deficient S. cerevisiae Strains. Autophagy 3, 337-346.

Erkki Ruoslahti; Targeting Breast Cancer Vasculature. Grant Proposal Final Progress Report, Submitted Mar. 2006.

Akerman M, Chan W, Laakkonen P, Bhatia S, and Ruoslahti E Nanocrystal targeting in vivo. *PNAS*, Oct. 1, 2002, vol. 99, No. 20, pp. 12617-12621.

Brown D and Ruoslahti E. Metadherin, a cell surface protein in breast tumors that mediates lung metastasis. Cancer Cell. Apr. 2004, vol. 5, p. 365-374.

Brown D, Pellecchia M and Ruoslahti D. Drug Identification through in vivo screening of chemical libraries. ChemBioChem. 2004, vol. 5, p. 871-875.

Pai J and Ruoslahti E. Identification of endothelial genes up-regulated in vivo. Gene 2005, vol. 347, p. 21-33.

Pilch J, Brown D, Komatsu M, Jarvinen T, Yang M, Peters D, Hoffman R and Ruoslahti E. Peptides selected for binding to clotted plasma accumulate in tumor stroma and wounds. PNAS Feb 2006, vol. 103, No. 8, p. 2800-2804.

Ruoslahti E. Drug targeting to specific vascular sites. Drug Discovery Today. Nov 2002, vol. 7, No. 22, p. 1138-1143.

Ruoslahti E. Vascular zip codes in angiogenesis and metastasis. Biochemical Society Transactions. 2004, vol. 32, part 3, p. 397-402.

Ruoslahti E, Duza T and Zhang L. Vascular homing peptides with cell-penetrating properties. Current Pharmaceutical Design, 2005, vol. 11, p. 3655-3660.

* cited by examiner

Control p32 kd

SEQUENCE LISTING

<160> NUMBER OF SEQ ID NOS: 12

<210> SEQ ID NO 1
<211> LENGTH: 9
<212> TYPE: PRT
<213> ORGANISM: Artificial Sequence

```
<220> FEATURE:
<223> OTHER INFORMATION: Description of Artificial Sequence; note =
      synthetic construct

<400> SEQUENCE: 1

Cys Gly Asn Lys Arg Thr Arg Gly Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Gly Asn Lys Arg Thr Arg Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 3

Cys Arg Glu Lys Ala
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Cys Arg Val Arg Thr Arg Ser Gly Cys
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 5

Ala Arg Ala Leu Pro Ser Gln Arg Ser Arg
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 6

Lys Leu Ala Lys Leu Ala Lys
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7

Cys Asn Arg Arg Thr Lys Ala Gly Cys
 1               5

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 8

Thr Glu Gly Asp Lys Ala Phe Val Glu Phe Leu Thr Asp Glu Ile Lys
 1               5                  10                  15

Glu Glu

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

Thr Asp Gly Asp Lys Ala Phe Val Asp Phe Leu Ser Asp Glu Ile Lys
 1               5                  10                  15

Glu Glu

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 10
ggatgaggtt ggacaagaag a                                           21

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 11
cccaatatcg tggttgatgt tataa                                       25

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct
```

```
<400> SEQUENCE: 12
ggatgaggtt ggacaggagg a                                        21
```

METHODS AND COMPOSITIONS FOR TARGETING GC1QR/P32

CROSS-REFERENCE TO RELATED APPLICATIONS

This application claims benefit of U.S. Provisional Application No. 60/807,255, filed Jul. 13, 2006, herein incorporated by reference in its entirety.

STATEMENT REGARDING FEDERALLY SPONSORED RESEARCH

This invention was made with government support under NIH grants PO1 CA 82713, and RO1 CA115410; and Cancer Center support grant P30 CA 30199; as well as Department of Defense grant DAMD 17-02-1-0315. The government has certain rights in the invention.

FIELD OF THE INVENTION

The present invention relates generally to the fields of molecular medicine and cancer biology and, more specifically, to molecules that interact with the gC1q/p32 receptor.

BACKGROUND OF THE INVENTION

C1q is a component of the CI complex of the classical complement pathway (R. B. Sim and K. B. M. Reid, Immunology Today 1991; 12:307-311). The biological functions of C1q are diverse, including initiation of the complement cascade for opsonization and cytolysis, and mediation of several different functions depending on the cell types expressing the C1q receptor. C1q enhances FcR and CR1-mediated phagocytosis in monocytes/macrophages (D. A. Bobak et al., Eur. J. Immunol. 1988; 18:2001-2007; D. A. Bobak et al., J. Immunol. 1987; 138:1150-1156), stimulates immunoglobulin production by B cells (K. R. Young et al., J. Immunol. 1991; 146:3356-3364), activates platelets to express αIIb/β3 integrins, P-selectin, and procoagulant activity (E. I. B. Peerschke et al., J. Exp. Med. 1993; 178:579-587; E. I. B. Peerschke et al., J. Immunol. 1994; 152:5896-5901), activates tumor cytotoxicity of macrophages (R. W. Leu et al., J. Immunol. 1990; 144:2281-2286), exerts anti-proliferative effects on T cell growth (A. Chen et al., J. Immunol. 1994; 153:1430-1440), and serves as a receptor for the *Listeria monocytogenes* invasion protein InIB Braun et al., EMBO J, 2000; 19: 1458-1466).

A 33 kilodalton (kD) receptor, designated gC1qR/p32 (and alternatively referred to as p32, and referred to herein as gC1qR/p32), which binds to the globular head of C1q molecules has been identified, cloned and sequenced (B. Ghebrehiwet et al., J. Exp. Med. 1994; 179:1809-1821; E. I. B. Peerschke et al., J. Immunol. 1994; 152:5896-5901; A. Chen et al., J. Immunol. 1994; 153: 1430-1440). The crystal structure of gC1qR/p32 has also been solved (Jiang et al. PNAS, 1999; 96, 3572-3577). Another 60 kD receptor, designated cC1qR, binds to the amino-terminal collagen-like region of C1q (B. Ghebrehiwet, Behring Inst. Mitt. 1989; 84:204-215; A. Chen et al., J. Immunol. 1994; 153:1430-1440). Based on the detection of gC1q-R mRNA by polymerase chain reaction (PCR) amplification and gC1q-R protein expression by immunochemical methods, this receptor was found to exist on a large number of different cell types, e.g. B cells, T cells, monocytes/macrophages, neutrophils, eosinophils, fibroblasts, platelets, endothelial cells, liver cells, neural cells and smooth muscle cells. The gC1q-R protein is over-expressed in tumor cells and tumors (Rubinstein et al., Int J Cancer, 2004; 110: 741-750).

The endothelial lining of blood vessels is highly diversified. Many, and perhaps all, normal tissues impart a tissue-specific "signature" on their vasculature, and tumor vessels differ from normal vessels both in morphology and molecular composition (Ruoslahti E. Specialization of tumor vasculature. Nat Rev Cancer 2002; 2:83-90). Tumors induce angiogenesis to support expansive growth (Hanahan D, Weinberg R A. The hallmarks of cancer. Cell 2000; 100:57-70) and many of the changes in tumor vessels are angiogenesis related (Brooks P G et al. J Reprod Med 1994; 39:755-60; Christian et al. J Cell Biol 2003; 163:871-8; Ferrara et al. Nat Med 1999; 5: 1359-64; Pasqualini et al Cancer Res 2000; 60: 722-7). Moreover, tumor blood vessels have tumor type-specific and, in some stages, stage-specific characteristics; in vivo screening of phage libraries has yielded distinct sets of homing peptides selectively recognizing angiogenic signatures in two transgenic mouse models of organ-specific tumorigenesis. Homing peptides can also distinguish the angiogenic blood vessels of premalignant lesions from those of fully malignant lesions in the same tumor. Lymphatic vessels in tumors also carry specific markers that distinguish tumor lymphatics from lymphatics in normal tissues (Laakkonen et al., Nat Med 2002; 8: 751-755; Laakkonen et al., Proc Natl Acad Sci USA, 2004; 101: 9381-9386: Zhang et al., Cancer Res, 2006; 66: 5696-9706). Tumor blood vessels and lymphatics provide important targets for tumor therapy. Destroying tumor blood vessels or preventing their growth suppresses tumor growth, whereas tumor lymphatics are not essential for tumor growth, but destroying them reduces metastasis (Saharinen et al. Trends Immunol 2004; 25:387-95).

The elevated expression of gC1qR/p32 in tumors and the findings reported here show there is a need for new therapeutic strategies for selectively targeting gC1q receptors (gC1qR, alternatively referred to in the art and herein as p32, and throughout as gC1qR/p32). The present invention satisfies this need by providing molecules that selectively interact with gC1qR/p32, and which are suitable for selectively targeting chemotherapeutic drugs, gene therapy vectors or other agents to the appropriate tissue. Related advantages also are provided.

BRIEF SUMMARY OF THE INVENTION

Disclosed herein are methods of treating a disease associated with gC1q/p32 receptor comprising identifying a subject having a disease associated with the gC1q/p32 receptor; and administering to the subject a composition comprising SEQ ID NO: 1.

Also disclosed are methods of detecting the presence of gC1q/p32 receptor, comprising bringing into contact a cell and a Lyp-1 composition, wherein the Lyp-1 composition comprises a moiety linked to a composition comprising SEQ ID NO: 1; and detecting interaction between gC1q/p32 receptor and the Lyp-1 composition, thereby detecting the presence of gC1q/p32 receptor.

Further disclosed are methods of detecting interaction between a gC1q/p32 receptor and a Lyp-1 composition, wherein the Lyp-1 composition comprises a moiety linked to a composition comprising SEQ ID NO: 1, the method comprising: selecting a cell for its potential to comprise a gC1q/p32 receptor; bringing into contact the Lyp-1 composition and the cell; and detecting interaction between the gC1q/p32 receptor and the Lyp-1 composition.

Also disclosed are methods of delivering a Lyp-1 composition to a gC1q/p32 receptor, wherein the Lyp-1 composition comprises a moiety linked to a composition comprising SEQ ID NO: 1; wherein the method comprises bringing into contact the Lyp-1 composition and a cell, thereby delivering the Lyp-1 composition to the gC1q/p32 receptor.

Disclosed are methods of delivering a Lyp-1 composition to a gC1q/p32 receptor, wherein the Lyp-1 composition comprises a moiety linked to a composition comprising SEQ ID NO: 1; comprising: selecting a cell for its potential to comprise a gC1q/p32 receptor; and bringing into contact the Lyp-1 composition and the cell, thereby delivering the Lyp-1 composition to the gC1q/p32 receptor.

Further disclosed are methods of determining and/or assessing gC1q/p32 receptor level in a cell of a subject, comprising: bringing into contact a cell of the subject and a Lyp-1 composition comprising a detectable agent linked to a composition comprising SEQ ID NO: 1; and detecting the level of Lyp-1 composition interacting with gC1q/p32 receptor, thereby determining and/or assessing gC1q/p32 receptor level in the cell.

Disclosed herein are methods of identifying a subject having a disease associated with gC1q/p32 receptor, the method comprising bringing into contact a cell of the subject and a Lyp-1 composition, wherein the Lyp-1 composition comprises a moiety linked to a composition comprising SEQ ID NO:1; and detecting interaction between gC1q/p32 receptor and the Lyp-1 composition, thereby detecting the presence or level of gC1q/p32 on the cell, wherein the presence or level of gC1q/p32 receptor on the cell identifies the subject as having a disease associated with a gC1q/p32 receptor.

Further disclosed are methods of screening for a compound that interacts with a gC1q/p32 receptor, comprising: bringing into contact a test compound, a Lyp-1 composition, and a gC1q/p32 receptor, wherein the Lyp-1 composition comprises SEQ ID NO: 1; and detecting unbound Lyp-1 composition, wherein a given amount of unbound Lyp-1 composition indicates a compound that interacts with gC1q/p32 receptor.

Also disclosed are methods of treating a disease associated with gC1q/p32 receptor comprising identifying a subject having a disease associated with the gC1q/p32 receptor; and administering to the subject a composition that interacts with the gC1q/p32 receptor in the same location as Lyp-1, thereby treating a disease associated with the gC1q/p32 receptor.

The gC1q/p32 receptor can be, for example, on or in a cell. The cell can be in any context, such as in an organism, in situ, ex vivo, in culture, and/or in vitro.

Also disclosed is a method of treating or preventing a disease in a subject associated with gC1q/p32 receptor, the method comprising administering to the subject a composition that modulates gC1q/p32 receptor expression or activity, thereby treating or preventing a disease in a subject associated with the gC1q/p32 receptor. The disease can be cancer. Expression or activity of the gC1q/p32 receptor can be inhibited. This can occur by the use of interfering nucleic acid, such as shRNA or siRNA. Activity of the gC1q/p32 receptor can be inhibited by the LyP-1 peptide, an antibody, or a small molecule mimic of Lyp-1.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1 shows gC1q/p32R binds Lyp-1 peptide in pull down assay. Pull down assays are shown with biotinylated Lyp-1 peptide (SEQ ID NO: 1, CGNKRTRGC) from protein extracts derived from MDA-MB-435 cultured cells (a) or MDA-MB-435 tumor xenografts (b). A tumor homing peptide, CREKA (SEQ ID NO: 3), and a peptide CRV which resembles Lyp-1 in its amino acid composition and cyclic structure (SEQ ID NO: 4, CRVRTRSGC), were used as negative controls. (a) Left panel: silver staining of Lyp-1 bound proteins. The arrow indicates a specific 33 kD band, which was identified as gC1q/p32R by mass spectrometry. Right panel: immunoblot of total cell extract (Tot lysate) and proteins bound to Lyp-1 and control peptides using a monoclonal antibody against gC1q/p32 receptor. The antibody recognizes a band of 33 kD in the total proteins lysate and in the Lyp-1 pull down. Anti gC1q/p32 receptor reactive bands are not detected in the pull downs from both control peptides. Silver staining of proteins pulled down from MDA-MB-435 tumor xenografts by Lyp-1 peptide, revealed an additional 75 kD band (b-left panel), which was also identified as gC1q/p32 receptor by mass spectrometry. The monoclonal antibody against gC1qR/p32 recognized a 75 kD and a 33 kD band only in the Lyp-1 peptide pull down (b-right panel).

FIG. 2 shows Lyp-1 phage specifically binds to purified gC1qR/p32 protein. (a) Purified gC1qR or BSA, as a control, were coated onto microtiter wells (5 μg/ml) and targeted for binding with 108 pfu of insertless phage, Lyp-1 phage, or control phage carrying another tumor homing peptide (CREKA, SEQ ID NO: 3). After 16 hours of incubation at 37° C., bound phages were eluted and quantified by plaque assay. Results are expressed as fold of Lyp-1 and CREKA (SEQ ID NO: 3) phages recovered over insertless phage and are representative of five independent experiments. (b) An antibody against the N-terminus of gC1qR inhibits Lyp-1 phage binding to purified gC1qR/p32. Left panel: Diagram of precursor (aa 1-282) and mature (aa 74-282) gC1qR/p32 protein. Boxes indicate the amino acid residues recognized by the monoclonal antibodies, mAb 60.11 and mAb 74.5.2, respectively at the N-terminus (aa 76-93) and C-terminus (aa 204-282) of the mature protein. The amino acid sequence recognized by mAb 60.11 is also indicated. Right panel: $1.5\times10^7$ pfu of insertless and Lyp-1 phages were allowed to bind for 6 hours at 37° C. to gC1qR/p32 protein coated onto microtiter plates in the presence or absence of 20 μg/ml of either mAbs 60.11, 74.5.2 or purified mouse IgG1 (mIgG). The results are representative of three independent experiments and are expressed as percentage of phage binding, with Lyp-1 phage binding alone as 100%.

FIG. 3 shows LyP-1 peptide binds to p32 protein in tumor cell extracts. A. Proteins bound to biotinylated LyP-1 peptide (CGNKRTRGC, SEQ ID NO: 1) from extracts of cultured MDA-MB-435 cells. Peptides with the sequences CREKA (SEQ ID NO: 3) and CRVRTRSGC (CRV, SEQ ID NO: 4) were used as negative controls in the pull down. Left panel: silver staining of LyP-1 bound proteins. The arrow indicates a specific band that was identified as p32 by mass spectrometry. Right panel: Anti-p32 immunoblot of total cell extract (lysate) and proteins bound to the LyP-1 and control peptides. B. Phage binding to p32. Purified p32, or BSA as a control, were coated onto microtiter wells and binding of LyP-1 phage, insertless phage, and phage clones displaying the tumor homing peptides CREKA (SEQ ID NO: 3) and LyP-2 (CNRRTKAGC, SEQ ID NO: 7) to the wells was tested. Results are expressed as fold of bound peptide phage over insertless phage (±SD) and are representative of five independent experiments. C. Diagrammatic representation of precursor (amino acids 1-282) and mature (amino acids 74-282) forms of p32 protein. Boxes indicate the amino acid residues recognized by the monoclonal antibodies, mAb 60.11 and mAb 74.5.2, respectively, at the N-terminus (amino acids 76-93) and C-terminus (amino acids 204-282) of the mature protein. The amino acid sequence recognized by mAb 60.11 is also shown. D. Inhibition of LyP-1 phage binding to purified p32 by mAb 60.11. Anti-p32 mAb 74.5.2 and purified mouse IgG1 (mIgG; negative control) do not inhibit the binding. The results are representative of three independent experiments and are expressed as percentage of phage binding (±SD), with LyP-1 phage binding alone as 100%.

FIG. 4 shows expression and cell surface localization of p32 in tumor cells. A. Immunoblot of endogenous p32 in extracts of the indicated cultured tumor cell lines. p32 was detected with mAb 60.11, and β-actin was used as loading control. B and C. FACS analysis to detect cell surface expression of p32 in tumor cell cultures (B) and primary cell suspensions from MDA-MB-435 and C8161 tumor xenografts (C, left panel). Rabbit IgG or a polyclonal antibody against full-length p32 were applied to live cells and detected with an Alexa 488-labeled secondary antibody. Propidium iodide-negative (living) cells were gated for the analysis. The total expression level of p32 in lysates from tumor xenografts was detected by immunoblot (C, right panel).

FIG. 5 shows LyP-1 binds to p32 at the cell surface. A. C8161 cells were transiently transfected with pEGFP together with either empty pcDNA3.1 vector or p32 pcDNA3.1 vector. Transfected cells were sorted for EGFP expression and the sorted populations were used for phage binding assay and immunoblot analysis with anti-p32. LyP-1 phage binding to cells transfected with the empty vector or p32 vector is expressed as fold binding over insertless phage. The graph represents the mean of binding in two independent experiments performed in duplicate (LyP-1 vs insertless phage in p32-transfected cells p<0.05; Student's t test). B. MDA-MB-435 S35 cells were transiently transfected with p32-specific or control siRNAs. 48 hours after transfection, inhibition of p32 expression was checked by immunoblot analysis and immunostaining (upper panels). β-actin was used as a control. (Lower panels) cells transfected with p32 siRNA or control siRNA were incubated for 1 h at 4° C. in the presence of 10 µM FITC conjugated LyP-1 peptide or a control peptide, ARALPSQRSR (ARAL, SEQ ID NO: 5), which has same overall charge as LyP-1. Cells incubated in the absence of peptide served as negative control. Down-regulation of p32 expression reduced LyP-1 binding to the cells (left panel), but control peptide fluorescence was unaffected (right panel). A representative experiment out of three is shown. C. LyP-1 phage binding in Raji cells in the presence of 40 µg/ml of mIgG1 (control), mAb 60.11, or mAb 74.5.2. Insertless phage was used to determine background phage binding. The results are representative of three independent experiments and are expressed as percentage of phage binding (±SD), with binding of LyP-1 phage in the presence of mIgG1 set as 100%.

FIG. 6 shows expression of p32 in tumor xenografts and human cancers. A. Double staining of sections from MDA-MB-435 xenograft tumors for p32 and podoplanin as a marker for lymphatic vessels, or CD31 and Meca-32 as markers for blood vessels. Polyclonal anti-p32 antibody recognizes cell clusters in podoplanin-positive areas. Cells that are positive both for p32 and podoplanin frequently line vessel-like structures that are negative for the blood vessel markers (lower panels). B. Co-localization of LyP-1 peptide and p32 in tumors. Fluorescein-conjugated LyP-1 peptide was intravenously injected into mice bearing MDA-MB-435 tumors and allowed to circulate for 1 hour before removal of the tumor for p32 immunohistochemical staining and analysis of LyP-1 fluorescence. C. Partial tumor co-localization of intravenously injected FITC-LyP-1 peptide (upper panel) and p32 protein (lower panels) with the macrophages markers CD11b and Gr-1. D and E. Immunohistochemical detection of p32 in human tissue arrays. Anti-p32 mAb 60.11 was used for the staining. (D) Sequential tissue sections were stained separately for p32 and epithelial membrane antigen (EMA). (E) Comparison of p32 expression in tumors and the corresponding normal tissues. Parallel sections of all tissues examined were incubated with mIgG instead of mAb60.11 and showed no staining.

FIG. 7 shows knockdown of p32 in MDA-MB-435 tumor cells. A. Upper left panel, immunoblot analysis on whole cell lysates from three MDA-MB-435 clones stably expressing ShRNA for p32 (p32 kd; Cl 1, 2, and 3) and three clones expressing a base mismatch control ShRNA (Control, Cl 4, 5, and 6). Upper right panel-acidification of the culture media in p32 knockdown clones, as indicated by the color change of the phenol red indicator in the media to orange/yellow. Lower panels: lactate production and glucose consumption 4 days post cells seeding calculated as described in materials and shown as relative to control (p<0.001). B. Cellular ATP from lysates of p32 knockdown and control cells grown for 4 days in media with the indicated glucose concentrations. The ATP present in each lysate was normalized for the ATP production of control clones grown in 25 mM glucose. The result is the average (±SEM) of two independent experiments performed with three p32 kd and three control clones. (*=p<0.03, =p<0.002). C. Oxygen consumption. Shown are the values for p32 knockdown clones relative to control clones. The results come from three independent experiments (±SD) performed in triplicate (=p<0.001, *=p<0.05). D. Confocal analysis of p32 localization in cells. p32 knockdown and control cells were stained with anti-N-terminal p32 polyclonal antibody and anti-cytochrome c monoclonal antibody, followed by Alexa 488 and Alexa 594 anti-rabbit and anti-mouse secondary antibodies, respectively. The panels on the right are high magnification of the white-framed areas in the merge panels.

FIG. 8 shows the effect of p32 knockdown on growth and survival of tumor cells in vitro. A. Proliferation of MDA-MB-435 p32 knockdown (kd) and control cells under high (25 mM) and low (2.5 mM) glucose conditions. Average cell number at each time point was determined by counting absolute cell number in duplicate wells of three p32 knockdown and control clones (p<0.0002). The panel on the right shows the color media of two control and p32 kd clones after 6 days in 25 mM or 2.5 mM glucose. B. Left panel-Microscopic analysis of p32 knockdown and control cells after 3 days in medium containing the indicated glucose concentration. The p32 kd clones show morphological changes in 2.5 mM glucose and cell death becomes pronounced in 0.5 mM glucose. Cell death was quantified by FACS analysis of cells that bind FITC-annexin V (right panel; *=<0.05). C. Upper left panel, immunoblot analysis of a parental p32 kd clone and single clones derived from it that express p32 from a cDNA resistant to the p32 shRNA silencing (Cl #3, 8, 14) or that were transfected with empty cDNA vector (Cl #9, 10, 18). A clone expressing control ShRNA (Control) was used to detect the endogenous level of p32. The lower left panel shows the restoration of culture medium pH by reintroduction of p32. The middle panels and the panel on the right show lactate production, glucose consumption, and growth rate in control, p32 kd and p32-restored (p32 kd+p32) clones.

FIG. 9 shows growth properties of tumors derived from p32 knockdown cells. Tumors were grown from three p32 kd and control clones (6 mice per clone) in the mammary fat pad of nude mice. A. Control tumors are homogenous in size, while p32 kd tumors are either significantly smaller than the control cell tumors, or swollen and hemorrhagic. The middle panel shows an example of a knockdown cell tumor with extensive necrosis accompanied by hemorrhage. The right panel shows average of tumor volume as a function of time (±SEM, p<0.001). B. BrdU incorporation in tumor cells. Mice were administered a pulse of BrdU 24 h prior to sacrifice. The graph indicates the number of cells per field that scored positive for BrdU staining. The data were derived by counting via Image-J software the number of BrdU positive cells in 4 random fields per tumor (N=14 tumors per group); p<0.003. C. Hematoxylin/eosin staining of tumors derived from p32 kd and control cell clones. Dark areas in p32 kd tumors are indicative of extensive necrosis. The upper images were taken with a 10× magnification, the lower images correspond to the indicated framed areas at 200× magnification. The percentage of necrotic areas was calculated via Image-J software (p<0.001).

Figure 10A:
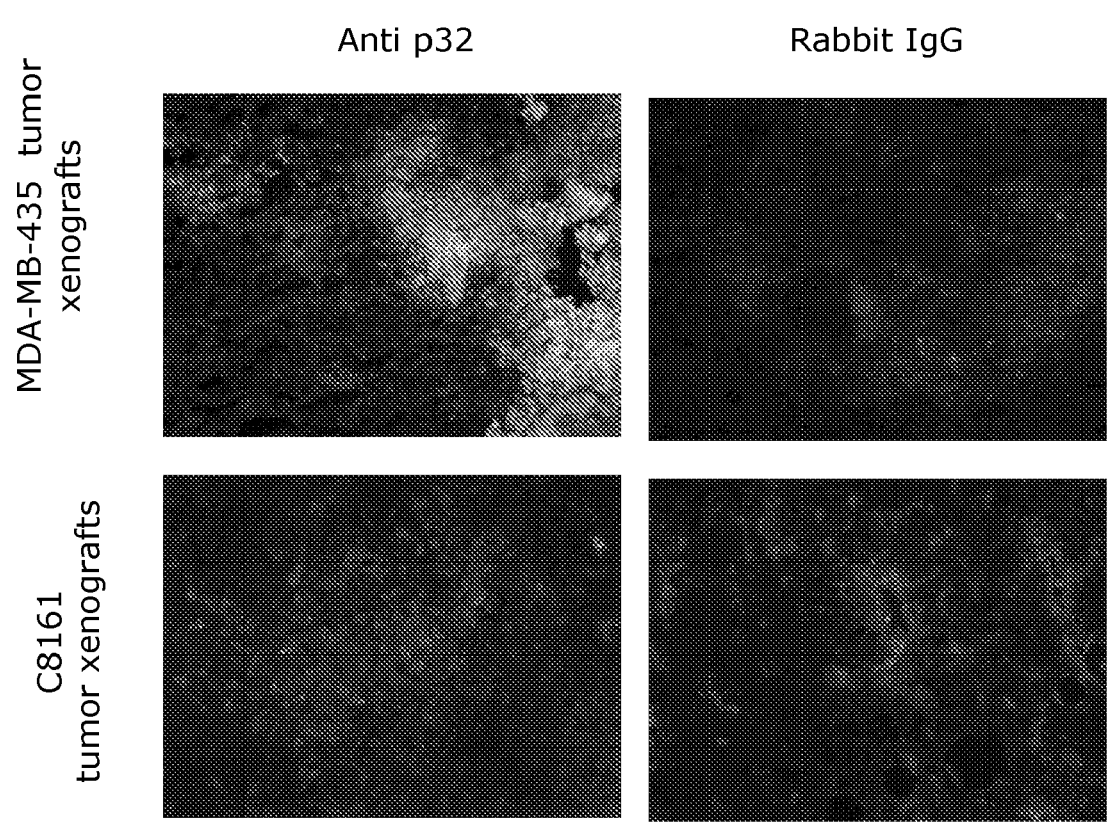
Figure 10B:
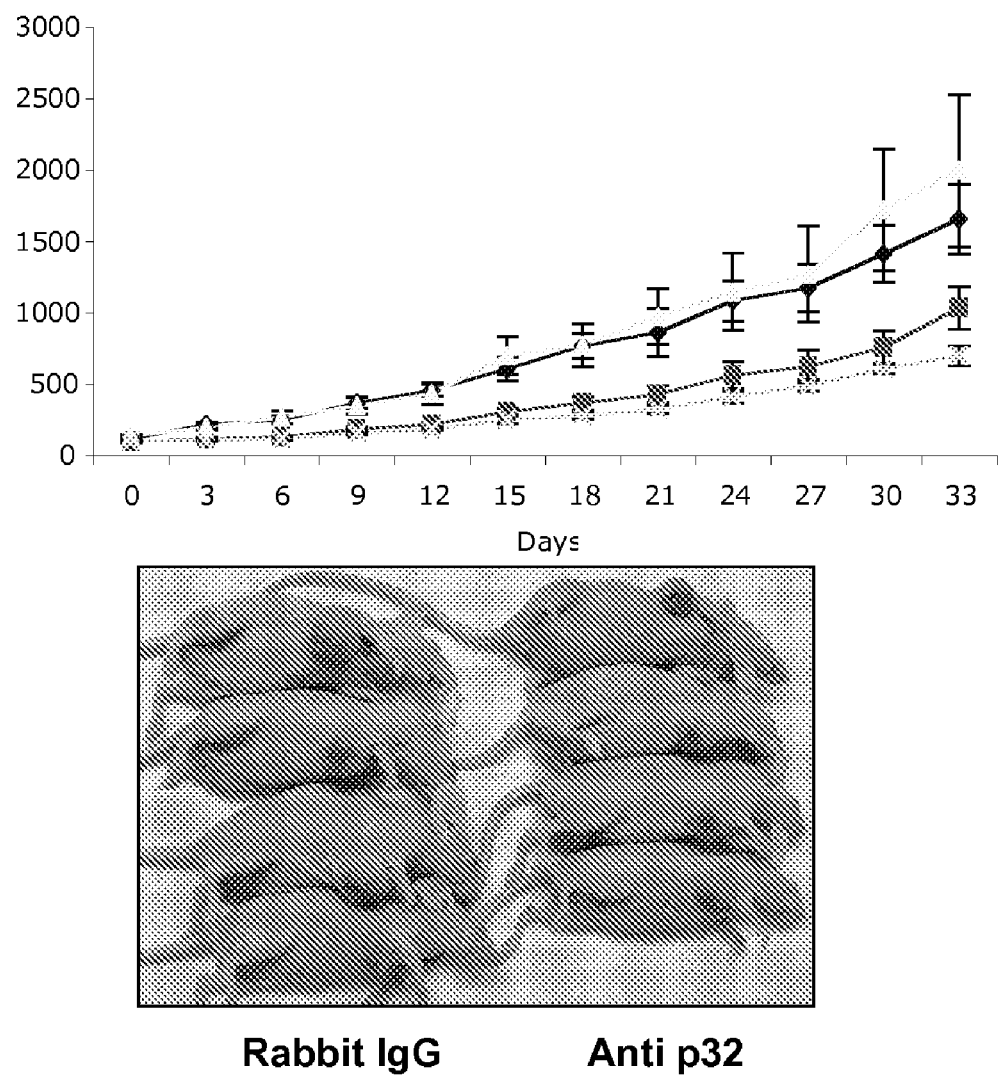
Figure 10B:
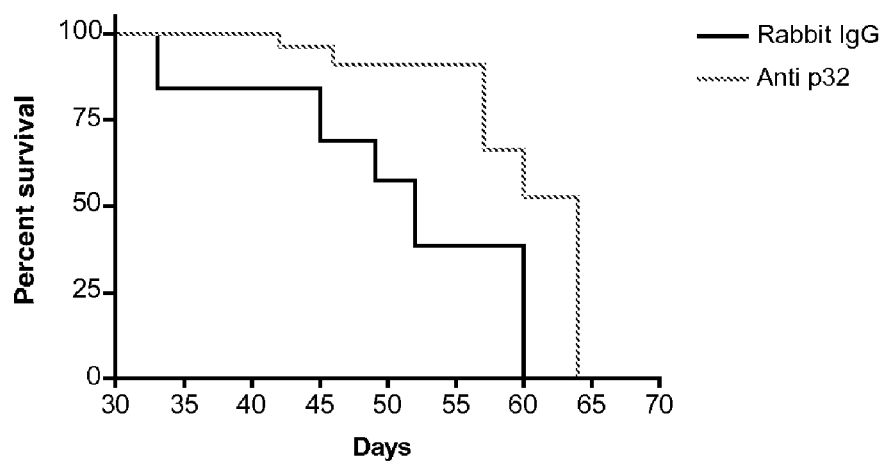

FIG. 10 shows inhibition of tumor growth by anti p32 treatment. A polyclonal antibody directed against aa 76-93 of both human and mouse p32 was produced and tested for homing to tumors in vivo. FIG. 10A—Affinity purified anti N-terminus p32 polyclonal antibody or rabbit IgG, as a control, was injected into the tail vein of mice bearing MDA-MB-435 or C8161 tumor xenografts. The tumor and various organs were removed 1 hour after the injection, sectioned, and examined for the presence of rabbit IgG using Alexa 488 anti rabbit IgG secondary antibody. The antibody recognizes clusters of cells similar to those visualized after i.v. injection of FITC LyP-1 or by p32 staining of tumor sections (FIG. 10A left panel). Homing to MDA-MB-435 xenografts is more efficient than to C8161 tumors, which express high and low levels of p32 respectively (FIG. 10A—right panel). FIG. 10B—Mice bearing MDA-MB-435 tumor xenografts were i.v. injected every three days with 400 and 800 μg of polyclonal anti p32 or rabbit IgG (n=4 mice per group) for a total of 33 days. In the graph are shown the kinetics of tumor growth in anti p32 and rabbit IgG treated mice. Both doses of antibody significantly inhibited tumor growth (Student's t test, p<0.001) without exhibiting any toxic effect as indicated by the constant body weight of the mice throughout the treatment.

DETAILED DESCRIPTION OF THE INVENTION

The disclosed method and compositions can be understood more readily by reference to the following detailed description of particular embodiments and the Example included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The term "multiwell plate" refers to a two dimensional array of addressable wells located on a substantially flat surface. Multiwell plates can include any number of discrete addressable wells, and include addressable wells of any width or depth. Common examples of multiwell plates include 96 well plates, 384 well plates and 3456 well Nanoplates™. Such multiwell plates can be constructed of any suitable material. Examples of suitable material include plastic, glass, or any essentially electrically nonconductive material By "knockdown" is meant a decrease in detectable mRNA expression. Nucleic acids are generally used to knockdown gene expression and generally comprise a sequence capable of hybridizing to the target sequence, such as mRNA. Examples of such functional nucleic acids include antisense molecules, ribozymes, triplex forming nucleic acids, external guide sequences (EGS), and small interfering RNAs (siRNA).

The term "gene knockout" as used herein, refers to the targeted disruption of a gene in vivo with complete loss of function that has been achieved by any transgenic technology familiar to those in the art. In one example, transgenic animals having gene knockouts are those in which the target gene has been rendered nonfunctional by an insertion targeted to the gene to be rendered non-functional by homologous recombination.

The term "hit" refers to a test compound that shows desired properties in an assay.

The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The term "transgenic" is used to describe an organism that includes exogenous genetic material within all of its cells. The term includes any organism whose genome has been altered by in vitro manipulation of the early embryo or fertilized egg or by any transgenic technology to induce a specific gene knockout.

The term "transgene" refers to any piece of DNA which is inserted by artifice into a cell, and becomes part of the genome of the organism (i.e., either stably integrated or as a stable extrachromosomal element) which develops from that cell. Such a transgene can include a gene which is partly or entirely heterologous (i.e., foreign) to the transgenic organism, or may represent a gene homologous to an endogenous gene of the organism. Included within this definition is a transgene created by the providing of an RNA sequence that is transcribed into DNA and then incorporated into the genome. The transgenes disclosed herein can include DNA sequences that encode the fluorescent or bioluminescent protein that may be expressed in a transgenic non-human animal.

The term "activity" as used herein refers to a measurable result of the interaction of molecules. Some exemplary methods of measuring these activities are provided herein.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist".

The term "inhibit" means to reduce or decrease in activity or expression. This can be a complete inhibition or activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The term "treating" as used herein refers to administering a compound after the onset of clinical symptoms.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The terms "higher," "increases," "elevates," or "elevation" refer to increases above basal levels, e.g., as compared to a control. The terms "low," "lower," "reduces," or "reduction" refer to decreases below basal levels, e.g., as compared to a control.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Materials

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to a number of molecules including the peptide are discussed, specifically contemplated is each and every combination and permutation of the peptides and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

A. Lyp-1 and gC1qR/p32

It has been discovered that the Lyp-1 (SEQ ID NO: 1, CGNKRTRGC) selectively interacts with the gC1q receptor (gC1qR/p32, which has been described in the literature by one of the alternative terms gC1qR and p32, and is described herein as either gC1qR, gC1q receptor, or p32, or as "gC1qR/p32" which refers to the protein known in the literature as gC1qR and as p32). gC1qR/p32 is associated with tumor lymphatic vasculature, for example, the lymphatic vasculature of breast cancer tumors, squamous carcinomas, and osteosarcomas. gC1qR/p32 is also associated with inflammation (Waggoner et al., J. Immunol. 2005 Oct. 1; 175(7):4706-14, herein incorporated by reference in its entirety for its teaching concerning gC1q/p32 receptors and inflammation).

As disclosed herein, the interaction of peptide Lyp-1 (SEQ ID NO: 1) and gC1qR/p32 was identified by pull down assays with biotinylated Lyp-1 peptide from protein extracts (FIG. 1). A tumor homing peptide, CREKA (SEQ ID NO: 3), and a peptide (CRV) which resembles Lyp-1 in its amino acid composition and cyclic structure (CRVRTRSGC, SEQ ID NO: 4), were used as negative controls. Anti gC1qR/p32 reactive bands were not detected in the pull downs from both control peptides. The monoclonal antibody against gC1qR/p32 recognized a 75 kD and a 33 kD band only in the Lyp-1 peptide pull down.

Figure 2A:
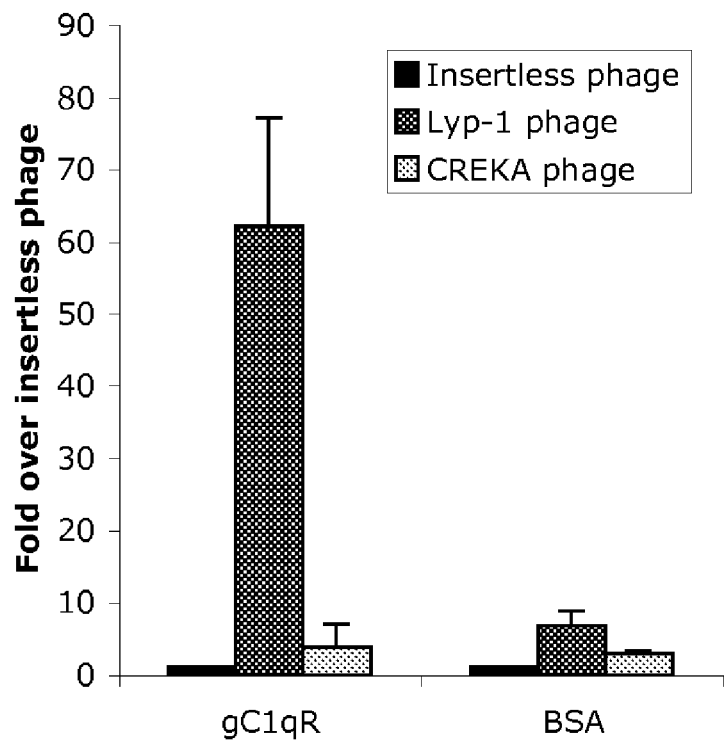
Figure 2B:
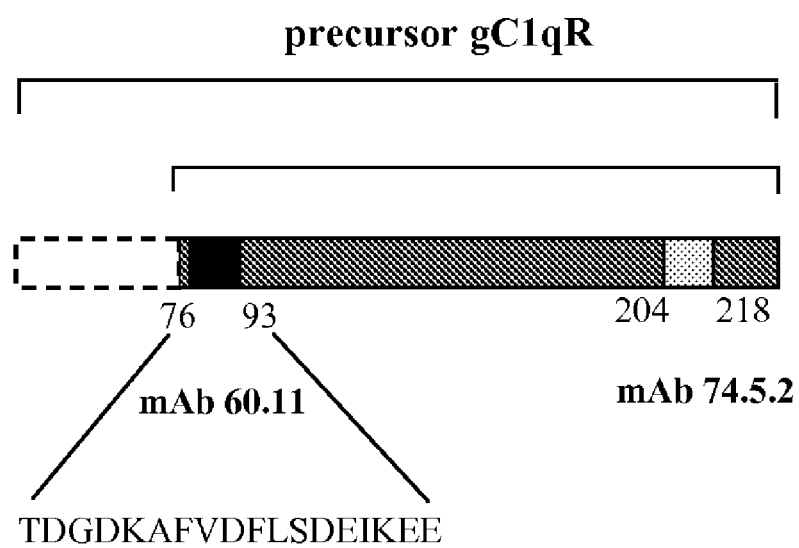
Figure 4A:
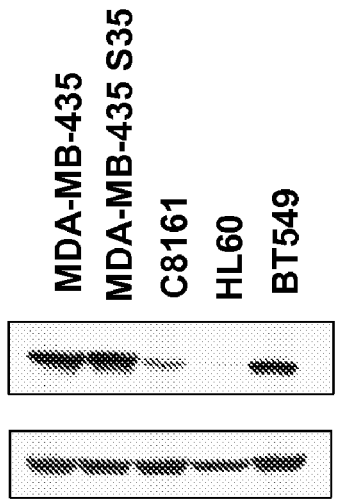

Furthermore, Lyp-1 phage specifically bound to purified gC1qR/p32 protein. Purified gC1qR/p32 or BSA, as a control, were coated onto microtiter wells and targeted for binding with insertless phage, Lyp-1 phage, or control phage carrying another tumor homing peptide (CREKA, SEQ ID NO: 3). As can be seen in FIG. 2a, the Lyp-1 phage bound gC1qR/p32, while the insertless and control phages showed essentially no interaction. Furthermore, an antibody against the N-terminus of gC1qR/p32 inhibited Lyp-1 phage binding to purified gC1qR/p32 (FIG. 2B).

gC1qR/p32 protein levels and cell surface expression are also shown in cultured tumor cells and tumor xenografts. FIG. 4A shows gC1qR/p32 western blot analysis from lysates of different tumor cell lines. C8161 melanoma cells and HL-60 promyelocitic leukemia cells, both low binders of Lyp-1 phage (Laakkonen et al., 2002), express low levels of gC1qR/p32 compared to MDA-MB-435 and BT549 breast cancer cells which exhibit higher Lyp-1 phage binding ability. FACS analysis was used to detect the cell surface expression of gC1qR/p32 in tumor cell cultures or primary cell suspensions from MDA-MB-435 tumor xenografts. Propidium iodide negative (living) cells were gated for the analysis. In cell suspensions from MDA-MB-435 tumor xenografts, polyclonal anti-gC1qR/p32 antibody caused a significant shift of the FACS peak compared with the rabbit IgG control. The cell surface expression of gC1qR/p32 was low in cultured MDA-MB-435 and BT549 cells. There was not cell surface expression of gC1qR/p32 in C8161 cells.

Furthermore, gC1qR/p32 overexpression enhanced Lyp-1 phage binding to C8161 melanoma cells (FIG. 5). A phage binding assay and western blot analysis were used to detect gC1qR/p32 overexpression. Lyp-1 phage binding to gC1qR/p32 was much greater than to empty vector. RNAi-mediated gC1qR/p32 silencing also decreases Lyp-1 peptide binding to the cell surface. MDA-MB-435 cells were transiently transfected with gC1qR/p32-specific or control siRNAs. Cells incubated in the absence of peptide served as FITC negative control. Compared to control siRNA transfected cells, down-regulation of gC1qR/p32 expression caused a shift in the peak of Lyp-1, but not control peptide fluorescence.

FIG. 3 shows tumor localization of gC1qR/p32 and Lyp-1 peptide. Staining of gC1qR/p32 and lymphatic or blood vessels, podoplanin and Meca32/CD31, respectively, in MDA-MB-435 tumor xenografts was done. Polyclonal anti-gC1qR/p32 antibody recognized cell clusters that lack blood vessels but contain lymphatics, or cells lining vessel-like structures positive for Podoplanin but not CD31 or Meca32. Lyp-1 peptide localized in gC1qR/p32-positive patches within the tumor.

Based on these findings, disclosed herein are Lyp-1 compositions useful in diseases and disorders associated with gC1qR/p32. For example, the Lyp-1 compositions disclosed herein are useful for reducing or preventing tumor metastasis in cancer patients having a primary tumor. The Lyp-1 compositions can be administered, for example, to a subject having pre-metastatic breast or bone cancer or to a subject having early or late stage metastatic breast or bone cancer. Lyp-1 polypeptides can also be useful, for example, for imaging tumor lymphatic vasculature, such as breast cancer or osteosarcoma lymphatic vasculature. The disclosed compositions are also useful for reducing or preventing inflammation in patients in need thereof.

Thus, disclosed herein are isolated peptides or peptidomimetic containing the amino acid sequence GNKRTRG (SEQ ID NO:2), or a peptidomimetic thereof. The invention further provides an isolated peptide or peptidomimetic containing the amino acid sequence CGNKRTRGC (SEQ ID NO:1) or a peptidomimetic thereof.

Disclosed are compositions, such as those comprising Lyp-1, that selectively interact with tumors and sites of inflammation, as well as other diseases and disorders associated with gC1qR/p32. A variety of Lyp-1 compositions can be used in the disclosed methods. Such compositions include, without limitation, peptides as disclosed herein. The disclosed compounds, compositions, molecules and methods can include or use the disclosed Lyp-1 compositions in various forms, including peptides and peptidomimetics as disclosed. For convenience of expression, in many places herein the use or inclusion of peptides will be recited. It is understood that, in such cases, it is considered Lyp-1 compositions in various forms can also be used or included in the same or similar ways as is described in terms of peptides, and such use and inclusion is specifically contemplated and disclosed thereby.

There are multiple diseases and disorders associated with the gC1q/p32 receptor. Examples include, but are not limited to, cancer and inflammation.

The composition comprising SEQ ID NO:1 can further comprise a moiety. Examples of moieties include, but are not limited to, therapeutic or diagnostic moieties. Therapeutic moieties can include anti-angiogenic agents or cytotoxic agents. The therapeutic moiety can target a DNA-associated process. The therapeutic moiety can be selected from the group consisting of an alkylating agent, an anti-tumor antibiotic and a sequence-selective agent. Other examples of therapeutic moieties include cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286. The moiety can also be a nanoparticle.

Disclosed are methods of detecting the presence of gC1q/p32 receptor, the method comprising bringing into contact a cell and a Lyp-1 composition, wherein the Lyp-1 composition comprises a moiety linked to a composition comprising SEQ ID NO: 1; and detecting interaction between gC1q/p32 receptor and the Lyp-1 composition, thereby detecting the presence of gC1q/p32 receptor. The gC1q/p32 receptor can be, for example, on or in a cell. The cell can be in any context, such as in an organism, in situ, ex vivo, in culture, and/or in vitro.

The moiety can be a detectable moiety. Examples of such moieties include, but are not limited to, a polypeptide, a nucleic acid molecule, a small molecule, a fluorophore, fluorescein, rhodamine, a radionuclide, indium-111, technetium-99, carbon-11, carbon-13, or a combination thereof.

The Lyp-1 composition being brought into contact with the cell described above can comprise a virus in one example. The Lyp-1 composition can also comprise a phage.

By "selectively interacts with" is meant that a stated compound or material can preferentially interact with a stated target compared with non-targets. Thus, for example, in vivo, Lyp-1 can preferentially interact with the gC1qR/p32 as compared to non-target. Therefore, when gC1qR/p32 is associated with a cancerous cell, or a site of inflammation, Lyp-1 will interact with the cancerous cell or site of inflammation preferentially, as compared to a non-cancerous cell, or a site without inflammation. Selective or preferential interaction with, for example, tumors, generally is characterized by at least a two-fold or greater localization at the cancerous site. A Lyp-1 peptide can be characterized by 5-fold, 10-fold, 20-fold or more preferential localization to cancerous sites such as tumors, as compared to several or many tissue types of non-tumoral tissue, or as compared to most or all non-tumoral tissue. Thus, it is understood that, in some cases, Lyp-1 interacts with, in part, one or more normal organs in addition to those with gC1qR/p32 present. Selective interaction can also be referred to as targeting or homing.

As discussed above, selectively interacting with, including preferential and/or selective homing, does not mean that Lyp-1 does not bind to any normal and/or non-targeted areas. In some embodiments, interaction selectivity can be, for example, at least about 20-fold, at least about 30-fold, at least about 50-fold, at least about 75-fold, at least about 100-fold, at least about 150-fold, or at least about 200-fold selective for a corresponding target. Selective interaction can be, for example, in terms of relative amounts or in terms of relative $K_i$ over other non-target components. In some embodiments, Lyp-1 can have at least about a 50-fold selectivity, at least about a 100-fold selectivity, at least about a 200-fold selectivity, at least about a 300-fold selectivity, at least about a 400-fold selectivity, at least about a 500-fold selectivity, at least about a 600-fold selectivity, at least about a 700-fold selectivity, at least about an 800-fold selectivity, at least about a 1000-fold selectivity, or at least about a 1500-fold selectivity to a corresponding target. For example, in some preferred embodiments, Lyp-1 can have a $K_i$ value against a target of less than about 200 nM, less than about 150 nM, less than about 100 nM, or less than about 75 nM. In some preferred embodiments, Lyp-1 can have a $K_i$ value against a target of more than about 50 nM, more than about 25 nM, more than about 20 nM, more than about 15 nM, more than about 10 nM, more than about 5 nM, more than about 3 nM, or more than about 1 nM. In some preferred embodiments, the targeting moiety binds its target with a $K_D$ less than about $10^{-8}$ M, less than about $10^{-9}$ M, less than about $10^{-10}$ M, less than about $10^{-11}$ M, less than about $10^{-12}$ M, less than about $10^{-13}$ M, or less than about $10^{-14}$ M.

B. P32/GC1Q RECEPTOR

It has been found that knocking down gC1qR/p32 expression in tumor cells shift their metabolism toward glycolysis and that, surprisingly, the glycolytic phenotype is associated with impaired tumor cell survival and growth, especially under adverse growth conditions (Example 2). At the same time, tumorigenicity of the gC1qR/p32 knockdown cells is reduced. Therefore, disclosed herein are methods of targeting the gC1q/p32 receptor in order to treat gC1q/p32 receptor-related disorders and diseases, as described herein. An example of such a disease is cancer.

Also disclosed herein is a method of treating a disease in a subject associated with gC1q/p32 receptor, the method comprising administering to the subject a composition that modulates gC1q/p32 receptor expression or activity, thereby treating a disease in a subject associated with the gC1q/p32 receptor. The subject can have cancer. Expression or activity of the gC1q/p32 receptor can be inhibited. This can occur by the use of interfering nucleic acid, such as shRNA or siRNA. Activity of the gC1q/p32 receptor can be inhibited by LyP-1 peptide, an antibody, or a small molecule mimic of Lyp-1. The methods of treating cancer disclosed herein can be used in conjunction with other treatment therapies as well, as described below in the section relating to moieties.

Disclosed herein are subjects having a disease associated with the gC1q/p32 receptor. By this is meant that the subject has either an increased level of gC1q/p32 receptor, a decreased level of gC1q/p32 receptor, or that the gC1q/p32 receptor can be targeted to treat or ameliorate the symptoms of a disease or disorder. By an "increased level of gC1q/p32 receptor" is meant that the number of gC1q/p32 receptors in the subject as a whole is increased over normal, basal, or standard levels accepted by those of skill in the art. It can also mean that the number of gC1q/p32 receptors present in a given cell are increased over a basal, normal, or standard amount. By a "decreased level of gC1q/p32 receptor" is meant that the number of gC1q/p32 receptors in the subject as a whole is deceased over normal, basal, or standard levels accepted by those of skill in the art. It can also mean that the number of gC1q/p32 receptors present in a given cell are decreased over a basal, normal, or standard amount. One of skill in the art would be able to determine gC1q/p32 levels in a subject as a whole, as well as in individual cells, using the methods disclosed herein and those known to those of skill in the art. One method of doing so involves using Lyp-1, as disclosed herein. Diseases associated with the gC1q/p32 receptor include cancer, for example.

C. PEPTIDES AND PEPTIDOMIMETICS

Disclosed are compositions related to an isolated peptide comprising SEQ ID NO:1 (Lyp-1). The isolated peptides can comprise, for example, SEQ ID NO:1, an amino acid sequence at least about 90% identical to SEQ ID NO: 1, or the amino acid sequence of SEQ ID NO:1 having one or more conservative amino acid substitutions. The peptide can be at least about 90%, 80%, 70%, or 60% identical to the amino acid sequence of SEQ ID NO:1. The amino acid sequence of SEQ ID NO:1 can have one, two, three, four, five, six, seven, eight, or nine conservative amino acid substitutions, for example. The peptide can comprise a chimera of the amino acid sequence SEQ ID NO:1. Such a chimera can be additive, where sequence of one sequence is added to another sequence, substitutional, where sequence of one sequence is substituted for sequence of another sequence, or a combination. As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity.

The amino acid sequence can be linear, circular or cyclic. The amino acid segment can be circularized or cyclized via any suitable linkage, for example, a disulfide bond. The peptide can have any suitable length, such as a length of less than 100 residues. The peptide can have a length of less than 50 residues. The peptide can have a length of less than 20 residues.

The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides can have any suitable length. The disclosed peptides can have, for example, a relatively short length of less than six, seven, eight, nine, ten, 12, 15, 20, 25, 30, 35 or 40 residues. The disclosed peptides also can be useful in the context of a significantly longer sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH—(cis and trans), —$COCH_2$—, —$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. 1307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—$CH(OH)CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as β-alanine, γ-aminobutyric acid, and the like.

Also disclosed are chimeric proteins containing a disclosed peptide fused to a heterologous protein. In one embodiment, the heterologous protein can have a therapeutic activity such as cytokine activity, cytotoxic activity or pro-apoptotic activity. In a further embodiment, the heterologous protein can be an antibody or antigen-binding fragment thereof. In other embodiments, the chimeric protein includes a peptide containing the amino acid sequence SEQ ID NO:1, or a conservative variant or peptidomimetic thereof, fused to a heterologous protein. The term "heterologous," as used herein in reference to a protein fused to the disclosed peptides, means a protein derived from a source other than the gene encoding the peptide or from which the peptidomimetic is derived. The disclosed chimeric proteins can have a variety of lengths including, but not limited to, a length of less than 100 residues, less than 200 residues, less than 300 residues, less than 400 residues, less than 500 residues, less than 800 residues or less than 1000 residues.

As used herein, "chimera" and "chimeric" refer to any combination of sequences derived from two or more sources. This includes, for example, from single moiety of subunit (e.g., nucleotide, amino acid) up to entire source sequences added, inserted and/or substituted into other sequences. Chimeras can be, for example, additive, where one or more portions of one sequence are added to one or more portions of one or more other sequences; substitutional, where one or more portions of one sequence are substituted for one or more portions of one or more other sequences; or a combination. "Conservative substitutional chimeras" can be used to refer to substitutional chimeras where the source sequences for the chimera have some structural and/or functional relationship and where portions of sequences having similar or analogous structure and/or function are substituted for each other. Typical chimeric and humanized antibodies are examples of conservative substitutional chimeras.

Also disclosed are bifunctional peptides, which contain Lyp-1 fused to a second peptide having a separate function. Such bifunctional peptides have at least two functions conferred by different portions of the full-length molecule and can, for example, display anti-angiogenic activity or pro-apoptotic activity in addition to the ability to selectively interact with gC1qR/p32.

Also disclosed are isolated multivalent peptides that include at least two subsequences each independently containing a peptide (for example, the amino acid sequence SEQ ID NO:1, or a conservative variant or peptidomimetic thereof). The multivalent peptide can have, for example, at least three, at least five or at least ten of such subsequences each independently containing a peptide. In particular embodiments, the multivalent peptide can have two, three, four, five, six, seven, eight, nine, ten, fifteen or twenty identical or non-identical subsequences. In a further embodiment, the multivalent peptide can contain identical subsequences, such as repeats of SEQ ID NO:1. In a further embodiment, the multivalent peptide contains contiguous identical or non-identical subsequences, which are not separated by any intervening amino acids. In yet further embodiments, the multivalent peptide can be cyclic or otherwise conformationally constrained. In one example, the peptide can be circularized or cyclized via a disulfide bond.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective interaction with a target of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an $N^\alpha$—$C^\alpha$ cyclized amino acid; an $N^\alpha$-methylated amino acid; a β- or γ-amino cycloalkane carboxylic acid; an α,β-unsaturated amino acid; a β,β-dimethyl or β-methylamino acid; a β-substituted-2,3-methano amino acid; an N—$C^\epsilon$ or $C^\alpha$—$C^\Delta$ cyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., Acta Crystalloqr. Section B, 35:2331 (1979)). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively interacting with cancerous cells.

If desired, an isolated peptide such as Lyp-1 can be cyclic or otherwise conformationally constrained. As used herein, a "conformationally constrained" molecule, such as a peptide, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further elsewhere herein.

As used herein in reference to a peptide, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl) benzoic acid (Mamb). Cyclization additionally can be effected, for example, through the formation of a lysinonor-leucine bond between lysine (Lys) and leucine (Leu) residues or a dityrosine bond between two tyrosine (Tyr) residues. The skilled person understands that these and other bonds can be included in a cyclic peptide.

D. FUNCTIONAL NUCLEIC ACIDS

As disclosed herein, functional nucleic acids can be used to modulate expression of the gC1q/p32 receptor, for example. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. As disclosed herein, the functional nucleic acid can interact with the gC1q/p32 receptor. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide.

Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukaryotic cells. (Yuan et al., *Proc. Natl. Acad. Sci. USA* 89:8006-8010 (1992); WO 93/22434 by Yale; WO 95/24489 by Yale; Yuan and Altman, *EMBO J.* 14:159-168 (1995), and Carrara et al., *Proc. Natl. Acad. Sci.* (USA) 92:2627-2631 (1995)). Representative examples of how to make and use EGS molecules to facilitate cleavage of a variety of different target molecules can be found in the following non-limiting list of U.S. Pat. Nos. 5,168,053, 5,624,824, 5,683,873, 5,728,521, 5,869,248, and 5,877,162.

E. NUCLEIC ACID DELIVERY

In the methods described herein which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPO-FECTAMINE (GIBCO-BRL, Inc., Gaithersburg, Md.), SUPERFECT (Qiagen, Inc. Hilden, Germany) and TRANS-FECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This disclosed compositions and methods can be used in conjunction with any of these or other commonly used gene transfer methods.

As one example, if the antibody-encoding nucleic acid is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

F. ANTIBODIES i. Antibodies Generally

Disclosed herein are antibodies that can be used to modulate the gC1q/p32 receptor, or Lyp-1. Examples of such antibodies can be found in FIG. 10. The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with gC1qR/p32. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

ii. Human Antibodies

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germline mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

iii. Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature*, 321:522-525 (1986), Riechmann et al., *Nature*, 332:323-327 (1988), Verhoeyen et al., *Science*, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

iv. Administration of Antibodies

Administration of the antibodies can be done as disclosed herein. Nucleic acid approaches for antibody delivery also exist. The broadly neutralizing anti DES-1 antibodies, for example, and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

G. LYP-1 COMPOSITIONS

Disclosed are Lyp-1 compositions comprising SEQ ID NO:1 (Lyp-1), and optionally also comprising a moiety. The moiety can be any molecule. For example, disclosed are moieties containing a therapeutic agent linked to SEQ ID NO:1.

Preferably the moiety is a molecule that is usefully targeted to the gC1q/p32 receptor. For example, moieties that affect the target, such as moieties with therapeutic effect, or that facilitate detection, visualization or imaging of the target, such as fluorescent molecule or radionuclides. The disclosed peptides, such as SEQ ID NO:1, that selectively interact with gC1qR/p32 can be usefully combined with, for example, moieties that can, for example, affect tumors and cancer, reduce or eliminate inflammation or infection, and/or promote wound healing. A variety of therapeutic agents are useful in the Lyp-1 compositions, including, without limitation, cancer chemotherapeutic agents, cytotoxic agents, anti-angiogenic agents, polypeptides, nucleic acid molecules and small molecules.

A Lyp-1 composition can comprise, for example, two or more, three or more, five or more, ten or more, twenty or more, thirty or more, forty or more, fifty or more, 100 or more, 200 or more, 300 or more, 400 or more, 500 or more, or 1000 or more copies of SEQ ID NO:1. The Lyp-1 composition can comprise peptides that all have an identical amino acid sequence. In another embodiment, the Lyp-1 composition can comprise two or more non-identical amino acid sequences. For example, SEQ ID NO:1 and another targeting peptide can be used separately or together. Moieties useful in a Lyp-1 composition incorporating multiple peptides include, without limitation, phage, retroviruses, adenoviruses, adeno-associated viruses and other viruses, cells, liposomes, polymeric matrices, non-polymeric matrices, particles such as gold particles, microdevices, nanodevices, and nano-scale semiconductor materials.

A Lyp-1 composition can contain, for example, a liposome or other polymeric matrix linked to at least two peptides. If desired, the liposome or other polymeric matrix can be linked to at least ten, at least 100 or at least 1000 peptides such as SEQ ID NO:1. Liposomes can be useful in such conjugates; liposomes consist of phospholipids or other lipids, are non-toxic, physiologically acceptable and metabolizable carriers that are relatively simple to make and administer (Gregoriadis, Liposome Technology, Vol. 1 (CRC Press, Boca Raton, Fla. (1984)). The liposome or other polymeric matrix can optionally include another component such as, without limitation, a therapeutic agent, cancer chemotherapeutic agent, cytotoxic agent, anti-angiogenic agent, polypeptide or nucleic acid molecule.

Components of the disclosed Lyp-1 compositions can be combined, linked and/or coupled in any suitable manner. For example, moieties and peptides can be associated covalently or non-covalently, directly or indirectly, with or without a linker moiety.

1. Moieties

Disclosed are compositions useful for directing a moiety to a target. For example, the moiety can be incorporated into a Lyp-1 composition. As used herein, the term "moiety" is used broadly to mean a physical, chemical, or biological material that generally imparts a biologically useful function to a linked molecule. A moiety can be any natural or nonnatural material including, without limitation, a biological material, such as a cell, phage or other virus; an organic chemical such as a small molecule; a radionuclide; a nucleic acid molecule or oligonucleotide; a polypeptide; or a peptide. Useful moieties include, but are not limited to, therapeutic agents such as cancer chemotherapeutic agents, cytotoxic agents, pro-apoptotic agents, and anti-angiogenic agents; detectable labels and imaging agents; and tags or other insoluble supports. Useful moieties further include, without limitation, phage and other viruses, cells, liposomes, polymeric matrices, non-polymeric matrices or particles such as gold particles, microdevices and nanodevices, and nano-scale semiconductor materials. These and other moieties known in the art can be components of a conjugate.

i. Therapeutic Agents

The moiety can be a therapeutic agent. As used herein, the term "therapeutic agent" means a molecule which has one or more biological activities in a normal or pathologic tissue. A variety of therapeutic agents can be used as a moiety.

In some embodiments, the therapeutic agent can be a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

Taxanes are chemotherapeutic agents useful in Lyp-1 compositions. Useful taxanes include, without limitation, docetaxel (Taxotere; Aventis Pharmaceuticals, Inc.; Parsippany, N.J.) and paclitaxel (Taxol; Bristol-Myers Squibb; Princeton, N.J.). See, for example, Chan et al., J. Clin. Oncol. 17:2341-2354 (1999), and Paridaens et al., J. Clin. Oncol. 18:724 (2000).

A cancer chemotherapeutic agent useful in a Lyp-1 composition also can be an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, Nature Biotechnology 15:510 (1997); Steiner, In "Angiogenesis: Key principles-Science, technology and medicine," pp. 449-454 (eds. Steiner et al.; Birkhauser Verlag, 1992)), which can contribute to its effectiveness in treating cancer.

An alkylating agent such as melphalan or chlorambucil also can be a useful cancer chemotherapeutic agent. Similarly, a vinca alkaloid such as vindesine, vinblastine or vinorelbine; or an antimetabolite such as 5-fluorouracil, 5-fluorouridine or a derivative thereof can be a useful cancer chemotherapeutic agent.

A platinum agent also can be a useful cancer chemotherapeutic agent. Such a platinum agent can be, for example, cisplatin or carboplatin as described, for example, in Crown, Seminars in Oncol. 28:28-37 (2001). Other useful cancer chemotherapeutic agents include, without limitation, methotrexate, mitomycin-C, adriamycin, ifosfamide and ansamycins.

A cancer chemotherapeutic agent useful for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a conjugate for treatment of breast cancer (Fisher et al., J. Natl. Cancer Instit. 90:1371-1388 (1998)).

The therapeutic agent can be an antibody such as a humanized monoclonal antibody. As an example, the anti-epidermal growth factor receptor 2 (HER2) antibody, trastuzumab (Herceptin; Genentech, South San Francisco, Calif.) can be a therapeutic agent useful for treating HER2/neu overexpressing breast cancers (White et al., Annu. Rev. Med. 52:125-141 (2001)).

Useful therapeutic agents also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, Pseudomonas exotoxin A, cholera toxin, ligand fusion toxins such as DAB389EGF, ricinus communis toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed conjugates and methods.

In one embodiment, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β, granulocyte macrophage colony stimulating factor (GM-CSF), granulocyte colony stimulating factor (G-CSF), interferon alpha. (IFN-α); interferon gamma. (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, Pseudomonas exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art (see below). It is understood that these and other polypeptides with biological activity can be a "therapeutic polypeptide."

A therapeutic agent can also be an anti-angiogenic agent. As used herein, the term "anti-angiogenic agent" means a molecule that reduces or prevents angiogenesis, which is the growth and development of blood vessels. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Vascular endothelial growth factor (VEGF) has been shown to be important for angiogenesis in many types of cancer, including breast cancer angiogenesis in vivo (Borgstrom et al., Anticancer Res. 19:4213-4214 (1999)). The biological effects of VEGF include stimulation of endothelial cell proliferation, survival, migration and tube formation, and regulation of vascular permeability. An anti-angiogenic agent can be, for example, an inhibitor or neutralizing antibody that reduces the expression or signaling of VEGF or another angiogenic factor, for example, an anti-VEGF neutralizing monoclonal antibody (Borgstrom et al., supra, 1999). An anti-angiogenic agent also can inhibit another angiogenic factor such as a member of the fibroblast growth factor family such as FGF-1 (acidic), FGF-2 (basic), FGF-4 or FGF-5 (Slavin et al., Cell Biol. Int. 19:431-444 (1995); Folkman and Shing, J. Biol. Chem. 267:10931-10934 (1992)) or an angiogenic factor such as angiopoietin-1, a factor that signals through the endothelial cell-specific Tie2 receptor tyrosine kinase (Davis et al., Cell 87:1161-1169 (1996); and Suri et al., Cell 87:1171-1180 (1996)), or the receptor of one of these angiogenic factors. It is understood that a variety of mechanisms can act to inhibit activity of an angiogenic factor including, without limitation, direct inhibition of receptor binding, indirect inhibition by reducing secretion of the angiogenic factor into the extracellular space, or inhibition of expression, function or signaling of the angiogenic factor.

A variety of other molecules also can function as anti-angiogenic agents including, without limitation, angiostatin; a kringle peptide of angiostatin; endostatin; anastellin, heparin-binding fragments of fibronectin; modified forms of anti-thrombin; collagenase inhibitors; basement membrane turnover inhibitors; angiostatic steroids; platelet factor 4 and fragments and peptides thereof; thrombospondin and fragments and peptides thereof; and doxorubicin (O'Reilly et al., Cell 79:315-328 (1994)); O'Reilly et al., Cell 88:277-285 (1997); Homandberg et al., Am. J. Path. 120:327-332 (1985); Homandberg et-al., Biochim. Biophys. Acta 874:61-71 (1986); and O'Reilly et al., Science 285:1926-1928 (1999)). Commercially available anti-angiogenic agents include, for example, angiostatin, endostatin, metastatin and 2ME2 (EntreMed; Rockville, Md.); anti-VEGF antibodies such as Avastin (Genentech; South San Francisco, Calif.); and VEGFR-2 inhibitors such as SU5416, a small molecule inhibitor of VEGFR-2 (SUGEN; South San Francisco, Calif.) and SU6668 (SUGEN), a small molecule inhibitor of VEGFR-2, platelet derived growth factor and fibroblast growth factor I receptor. It is understood that these and other anti-angiogenic agents can be prepared by routine methods and are encompassed by the term "anti-angiogenic agent" as used herein.

The Lyp-1 compositions disclosed herein can also be used to site of inflammation. Moieties useful for this purpose can include therapeutic agents belonging to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue. Examples of useful therapeutic agents include but are not limited to steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, and integrins.

Useful therapeutic agents also can be antimicrobial peptides. This can be particularly useful to target a wound or other infected sites. Thus, for example, also disclosed are Lyp-1 compositions comprising an antimicrobial peptide, where the Lyp-1 composition is selectively internalized and exhibits a high toxicity to the targeted area. Useful antimicrobial peptides can have low mammalian cell toxicity when not incorporated into the Lyp-1 composition. As used herein, the term "antimicrobial peptide" means a naturally occurring or synthetic peptide having antimicrobial activity, which is the ability to kill or slow the growth of one or more microbes. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli*, *Pseudomonas aeruginosa* or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic .alpha.-helical structure (see U.S. Pat. No. 5,789,542; Javadpour et al., J. Med. Chem. 39:3107-3113 (1996); and Blondelle and Houghten, Biochem. 31: 12688-12694 (1992)). An antimicrobial peptide also can be, for example, a β-strand/sheet-forming peptide as described in Mancheno et al., J. Peptide Res. 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, Biopolymers 37:105-122 (1995); Alvarez-Bravo et al., Biochem. J. 302:535-538 (1994); Bessalle et al., FEBS 274:-151-155 (1990.); and Blondelle and Houghten in Bristol (Ed.), Annual Reports in Medicinal Chemistry pages 159-168 Academic Press, San Diego). An antimicrobial peptide also can be an analog of a natural peptide, especially one that retains or enhances amphipathicity (see below).

An antimicrobial peptide incorporated into a Lyp-1 composition can have low mammalian cell toxicity linked to Lyp-1. Mammalian cell toxicity readily can be assessed using routine assays. As an example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 μM for lytic activity, preferably concentrations greater than 200, 300, 500 or 1000 μM.

In one embodiment, disclosed are Lyp-1 compositions in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art. $_D$(KLAKLAK)$_2$, (SEQ ID NO:6) for example, is an antimicrobial peptide which induces marked mitochondrial swelling at a concentration of 10 μM, significantly less than the concentration required to kill eukaryotic cells.

An antimicrobial peptide that induces significant mitochondrial swelling at, for example, 50 μM, 40 μM, 30 μM, 20 μM, 10 μM, or less, is considered a peptide that promotes disruption of mitochondrial membranes.

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, Proteins: Structures and Molecular Properties W. H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., Biochim. Biophys. Acta 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., Biopolymers 37:105-122 (1995)).

As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic .alpha.-helical structure generally has an equivalent number of polar and nonpolar residues within the amphipathic domain and a sufficient number of basic residues to give the peptide an overall positive charge at neutral pH (Saberwal et al., Biochim. Biophys. Acta 1197: 109-131 (1994)). One skilled in the art understands that helix-promoting amino acids such as leucine and alanine can be advantageously included in an antimicrobial peptide (see, for example, Creighton, supra, 1984). Synthetic, antimicrobial peptides having an amphipathic α-helical structure are known in the art, for example, as described in U.S. Pat. No. 5,789,542 to McLaughlin and Becker.

It is understood by one skilled in the art of medicinal oncology that these and other agents are useful therapeutic agents, which can be used separately or together in the disclosed compositions and methods. Thus, it is understood that a Lyp-1 composition can contain one or more of such therapeutic agents and that additional components can be included as part of the composition, if desired. As a non-limiting example, it can be desirable in some cases to utilize an oligopeptide spacer between Lyp-1 and the therapeutic agent (Fitzpatrick and Garnett, Anticancer Drug Des. 10:1-9 (1995)).

Other useful agents include thrombolytics, aspirin, anticoagulants, painkillers and tranquilizers, beta-blockers, ace-inhibitors, nitrates, rhythm-stabilizing drugs, and diuretics. Agents that limit damage to the heart work best if given within a few hours of the heart attack. Thrombolytic agents that break up blood clots and enable oxygen-rich blood to flow through the blocked artery increase the patient's chance of survival if given as soon as possible after the heart attack. Thrombolytics given within a few hours after a heart attack are the most effective. Injected intravenously, these include anisoylated plasminogen streptokinase activator complex (APSAC) or anistreplase, recombinant tissue-type plasminogen activator (r-tPA), and streptokinase. The disclosed Lyp-1 compositions can use any of these or similar agents.

ii. Detectable Agents

The moiety in the disclosed Lyp-1 compositions can also be a detectable agent. A variety of detectable agents are useful in the disclosed methods. As used herein, the term "detectable agent" refers to any molecule which can be detected. Useful detectable agents include compounds and molecules that can be administered in vivo and subsequently detected. Detectable agents useful in the disclosed compositions and methods include yet are not limited to radiolabels and fluorescent molecules. The detectable agent can be, for example, any molecule that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrasting agent, e.g., where the contrasting agent is ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, Gd can be used as a non-radioactive detectable agent in certain embodiments.

Other examples of detectable agents include molecules which emit or can be caused to emit detectable radiation (e.g., fluorescence excitation, radioactive decay, spin resonance excitation, etc.), molecules which affect local electromagnetic fields (e.g., magnetic, ferromagnetic, ferromagnetic, paramagnetic, and/or superparamagnetic species), molecules which absorb or scatter radiation energy (e.g., chromophores and/or fluorophores), quantum dots, heavy elements and/or compounds thereof. See, e.g., detectable agents described in U.S. Publication No. 2004/0009122. Other examples of detectable agents include a proton-emitting molecules, a radiopaque molecules, and/or a radioactive molecules, such as a radionuclide like Tc-99m and/or Xe-13. Such molecules can be used as a radiopharmaceutical. In still other embodiments, the disclosed compositions can comprise one or more different types of detectable agents, including any combination of the detectable agents disclosed herein.

Useful fluorescent moieties include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Particularly useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio. Fluorescent probes and there use are also described in Handbook of Fluorescent Probes and Research Products by Richard P. Haugland.

Further examples of radioactive detectable agents include gamma emitters, e.g., the gamma emitters In-111, I-125 and I-131, Rhenium-186 and 188, and Br-77 (see. e.g., Thakur, M. L. et al., Throm Res. Vol. 9 pg. 345 (1976); Powers et al., Neurology Vol. 32 pg. 938 (1982); and U.S. Pat. No. 5,011, 686); positron emitters, such as Cu-64, C-11, and O-15, as well as Co-57, Cu-67, Ga-67, Ga-68, Ru-97, Tc-99m, In-113m, Hg-197, Au-198, and Pb-203. Other radioactive detectable agents can include, for example tritium, C-14 and/or thallium, as well as Rh-105, I-123, Nd-147, Pm-151, Sm-153, Gd-159, Tb-161, Er-171 and/or Tl-201.

The use of Technitium-99m (Tc-99m) is preferable and has been described in other applications, for example, see U.S. Pat. No. 4,418,052 and U.S. Pat. No. 5,024,829. Tc-99m is a gamma emitter with single photon energy of 140 keV and a half-life of about 6 hours, and can readily be obtained from a Mo-99/Tc-99 generator.

In some embodiments, compositions comprising a radioactive detectable agent can be prepared by coupling a targeting moiety with radioisotopes suitable for detection. Coupling can occur via a chelating agent such as diethylenetriaminepentaacetic acid (DTPA), 4,7,10-tetraazacyclododecane-N,N',N'',N'''-tetraacetic acid (DOTA) and/or metallothionein, any of which can be covalently attached to the targeting moiety. In some embodiments, an aqueous mixture of technetium-99m, a reducing agent, and a water-soluble ligand can be prepared and then allowed to react with a disclosed targeting moiety. Such methods are known in the art, see e.g., International Publication No. WO 99/64446. In some embodiments, compositions comprising radioactive iodine, can be prepared using an exchange reaction. For example, exchange of hot iodine for cold iodine is well known in the art. Alternatively, a radio-iodine labeled compound can be prepared from the corresponding bromo compound via a tributylstannyl intermediate.

Magnetic detectable agents include paramagnetic contrasting agents, e.g., gadolinium diethylenetriaminepentaacetic acid, e.g., used with magnetic resonance imaging (MRI) (see, e.g., De Roos, A. et al., Int. J. Card. Imaging Vol. 7 pg. 133 (1991)). Some preferred embodiments use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70. Suitable ions include, but are not limited to, chromium(III), manganese(II), iron(II), iron(III), cobalt(II), nickel(II), copper(II), praseodymium(III), neodymium(III), samarium(III) and ytterbium(III), as well as gadolinium(III), terbium(III), dysoprosium(III), holmium(III), and erbium(III). Some preferred embodiments use atoms with strong magnetic moments, e.g., gadolinium(III).

In some embodiments, compositions comprising magnetic detectable agents can be prepared by coupling a targeting moiety with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the targeting moiety in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (e.g., hydroxides, carbonates and/or bicarbonates of sodium, potassium and/or lithium), organic bases, and/or basic amino acids can be used to neutralize acidic groups, e.g., to facilitate isolation or purification of the composition.

In preferred embodiments, the detectable agent can be coupled to Lyp-1 in such a way so as not to interfere with the ability of Lyp-1 to interact with gC1qR/p32. In some embodiments, the detectable agent can be chemically bound to Lyp-1. In some embodiments, the detectable agent can be chemically bound to a moiety that is itself chemically bound to Lyp-1, indirectly linking the imaging and targeting moieties.

H. PHARMACEUTICAL COMPOSITIONS AND CARRIERS

The disclosed compositions can be administered in vivo in a pharmaceutically acceptable carrier. By "pharmaceutically acceptable" is meant a material that is not biologically or otherwise undesirable, i.e., the material can be administered to a subject, along with the Lyp-1 composition, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

1. Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

I. COMBINATORIAL CHEMISTRY/SCREENING METHODS

The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed in SEQ ID NO:1 or portions thereof, are used as the target in a combinatorial or screening protocol.

It is understood that when using the disclosed compositions in combinatorial techniques or screening methods, molecules, such as macromolecular molecules, will be identified that have particular desired properties, such as interaction with gC1qR/p32. The molecules identified and isolated when using the disclosed compositions, such as Lyp-1, are also disclosed. Thus, the products produced using the combinatorial or screening approaches that involve the disclosed compositions, such as Lyp-1, are also considered herein disclosed.

Disclosed herein are methods of screening for a compound that interacts with a gC1q/p32 receptor, comprising: bringing into contact a test compound, a Lyp-1 composition, and a gC1q receptor, wherein the Lyp-1 composition comprises SEQ ID NO: 1; and detecting unbound Lyp-1 composition, wherein a given amount of unbound Lyp-1 composition indicates a compound that interacts with gC1q/p32 receptor.

Also disclosed is a method of screening for a test compound that modulates gC1q/p32 receptor activity, comprising: contacting a cell that comprises the gC1q/p32 receptor with a test compound; and detecting altered gC1q/p32 receptor activity; wherein altered levels of gC1q/p32 receptor activity indicate a compound that modulates gC1q/p32 receptor activity.

By "altered levels of activity" is meant that the gC1q/p32 receptor can display an increase or decrease in activity. The increase in activity can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% increase, or a 1 2, 3, 4, 5, 6, 7, 8, 9, 10, 20, 25, 30, 35, 40, 45, 50, 75, or 100 fold or more increase in activity, as compared to a standard, control, or basal level. The decrease in activity can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease in activity as compared to a standard, control, or basal level. For example, a test compound can interact with the gC1q/p32 receptor in such as way as to decrease the ability of the gC1q/p32 receptor to interact with another compound, thereby decreasing its activity. In another example, a test compound can prevent the synthesis of the gC1q/p32 receptor, thereby decreasing its activity in that way.

Disclosed is a method of screening for a test compound that interacts with the gC1q/p32 receptor, comprising: contacting a cell that comprises the gC1q/p32 receptor with a test compound; and detecting interaction between the gC1q/p32 receptor and the test compound. After the test compound has been shown to interact with the gC1q/p32 receptor, it can further be tested for its ability to modulate gC1q/p32 receptor activity, including the ability to treat a gC1q/p32 receptor-related disorder.

Further disclosed is a method of screening for a test compound that can be used to treat a gC1q/p32 receptor-related disorder, such as cancer, comprising: contacting a cell that comprises the gC1q/p32 receptor with a test compound; and detecting altered gC1q/p32 receptor activity; wherein altered levels of gC1q/p32 receptor activity indicate a compound that can modulate gC1q/p32 receptor activity. After the test compound has been shown to modulate gC1q/p32 receptor activity, the test compound can then be tested for its ability to treat a gC1q/p32 receptor-related disorder.

The modulation can comprise a decrease in gC1q/p32 receptor activity, expression, or the ability to treat a gC1q/p32 receptor-related disease. By a "decrease" is meant that the activity is less in the presence of the test compound than not in the presence of the test compound. The modulation can comprise an increase in gC1q/p32 receptor activity or related activity. By an "increase" is meant that the activity is greater in the presence of the test compound than not in the presence of the test compound.

The response of the gC1q/p32 receptor can be measured in the presence of various concentrations of test compound. The measuring steps can also comprise measuring the response at various concentrations of the test compound. For example, the concentration of the test compound can range from 1 nM to 1000 μM.

Assays contemplated by the invention include both binding assays and activity assays; these assays may be performed in conventional or high throughput formats. Modulator screens are designed to identify stimulatory and inhibitory agents. The sources for potential agents to be screened include natural sources, such as a cell extract (e.g., invertebrate cells including, but not limited to, bacterial, fungal, algal, and plant cells) and synthetic sources, such as chemical compound libraries or biological libraries such as antibody substance or peptide libraries. Agents are screened for the ability to either stimulate or inhibit the activity. Binding assays are used to detect activity levels. Both functional and binding assays of activity are readily adapted to screens for modulators such as agonist (stimulatory) and antagonist (inhibitory) compounds.

Contemplated herein are a multitude of assays to screen and identify modulators, such as agonists and antagonists, of the gC1q/p32 receptor (and downstream activity). In one example, the cell is immobilized and interaction with a candidate modulator is detected. In another example, the test compound is immobilized. In yet another example, interaction between gC1q/p32 receptor and the test compound is assessed in a solution assay. Another contemplated assay involves a variation of the di-hybrid assay wherein a modulator of protein/protein interactions is identified by detection of a positive signal in a transformed or transfected host cell.

Candidate modulators for screening according to contemplated by the invention include any chemical compounds, including libraries of chemical compounds. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, or analogs of known compounds, or analogs of compounds that have been identified as "hits" or "leads" in prior drug discovery screens, some of which may be derived from natural products or from non-directed synthetic organic chemistry. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see Science 282:63-68 (1998). Combinatorial libraries are composed of large numbers of peptides, oligonucleotides, or organic compounds as a mixture. These libraries are relatively easy to prepare by traditional automated synthesis methods, PCR, cloning, or synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997). Identification of modulators through use of the various libraries described herein permits modification of the candidate "hit" (or "lead") to optimize the capacity of the "hit" to modulate activity.

Candidate modulators contemplated by the invention can be designed and include soluble forms of binding partners, as well as chimeric, or fusion, proteins thereof. A "binding partner" as used herein broadly encompasses non-peptide modulators, peptide modulators (e.g., neuropeptide variants), antibodies (including monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR and/or antigen-binding sequences, which specifically recognize a polypeptide as disclosed herein), antibody fragments, and modified compounds comprising antibody domains that are immunospecific for the expression product.

Assays that measure binding or interaction of compounds with target proteins include assays that identify compounds that inhibit unfolding or denaturation of a target protein, assays that separate compounds that bind to target proteins through affinity ultrafiltration followed by ion spray mass spectroscopy/HPLC methods or other physical and analytical methods, capillary electrophoresis assays and two-hybrid assays.

One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method which distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., Anal. Chem., 69:1683-1691 (1997), incorporated herein by reference. This technique screens combinatorial libraries of 20-30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Alternatively, such binding interactions are evaluated indirectly using the yeast two-hybrid system described in Fields et al., Nature, 340:245-246 (1989), and Fields et al., Trends in Genetics, 10:286-292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene.

The literature is replete with examples of the use of radiolabeled ligands in HTS binding assays for drug discovery (see Williams, Med. Res. Rev. 11: 147-184 (1991); Sweetnam et al., J. Nat. Prod. 56:441-455 (1993) herein incorporated by reference in their entirety for their teaching concerning high throughput screens). It is also possible to screen for novel neuroregeneration compounds with radiolabeled ligands in HTS binding screens. Other reasons that recombinant receptors are preferred for HTS binding assays include better specificity (higher relative purity) and ability to generate large amounts of receptor material (see Hodgson, Bio/Technology 10:973-980 (1992)).

A variety of heterologous systems are available for expression of recombinant proteins and are well known to those skilled in the art. Such systems include bacteria (Strosberg et al., Trends in Pharm. Sci. 13:95-98 (1992)), yeast (Pausch, Trends in Biotech. 15:487-494 (1997)), several kinds of insect cells (Vanden Broeck, Intl. Rev. Cytol. 164:189-268 (1996)), amphibian cells (Jayawickreme et al., Curr. Opin. Biotechnol. 8:629-634 (1997)) and several mammalian cell lines (CHO, HEK293, COS, etc.; see Gerhardt et al., Eur. J. Pharmacol. 334:1-23 (1997); Wilson et al., Brit. J. Pharmacol. 125:1387-1392 (1998)). These examples do not preclude the use of other possible cell expression systems, including cell lines obtained from nematodes (WO 98/37177).

Inhibition of gC1qR/p32, or downstream products or genes related thereto, can result in a variety of biological responses, which are typically mediated by proteins expressed in the host cells. The proteins can be native constituents of the host cell or can be introduced through well-known recombinant technology. They can be mutants of native varieties as well. The proteins can be intact or chimeric.

Fluorescence changes can also be used to monitor ligand-induced changes in membrane potential or intracellular pH; an automated system suitable for HTS has been described for these purposes (Schroeder et al., J. Biomol. Screening 1:75-80 (1996)). Among the modulators that can be identified by these assays are natural ligand compounds; synthetic analogs and derivatives of natural ligands; antibodies, antibody fragments, and/or antibody-like compounds derived from natural antibodies or from antibody-like combinatorial libraries; and/or synthetic compounds identified by high throughput screening of libraries; and other libraries known in the art. All modulators that interact with gC1qR/p32 are useful for identifying Lyp-1-like polypeptides (e.g., for diagnostic purposes, pathological purposes, and other purposes known in the art). Agonist and antagonist modulators are useful for up-regulating and down-regulating gC1qR/p32 activity, respectively, for purposes described herein.

The assays may be performed using single putative modulators; they may also be performed using a known agonist in combination with candidate antagonists (or visa versa). Detectable molecules that may be used include, but are not limited to, molecules that are detectable by spectroscopic, photochemical, biochemical, immunochemical, electrical, radioactive, and optical means, including but not limited to bioluminescence, phosphorescence, and fluorescence. These detectable molecules should be a biologically compatible molecule and should not compromise the biological function of the molecule and must not compromise the ability of the detectable molecule to be detected. Preferred detectable molecules are optically detectable molecules, including optically detectable proteins, such that they may be excited chemically, mechanically, electrically, or radioactively to emit fluorescence, phosphorescence, or bioluminescence. More preferred detectable molecules are inherently fluorescent molecules, such as fluorescent proteins, including, for example, Green Fluorescent Protein (GFP). The detectable molecule may be conjugated to the GRK protein by methods as described in Barak et al. (U.S. Pat. Nos. 5,891,646 and 6,110,693). The detectable molecule may be conjugated at the front-end, at the back-end, or in the middle.

J. COMPUTER ASSISTED DRUG DESIGN

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as Lyp-1, are also disclosed. Thus, the products produced using the molecular modeling approaches that involve the disclosed compositions, such as Lyp-1, are also considered herein disclosed.

Thus, one way to isolate molecules that bind a molecule of choice is through rational design. This can be achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario.

Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

K. COMPOSITIONS WITH SIMILAR FUNCTIONS

It is understood that the compositions disclosed herein have certain functions, such as interacting with gC1qR/p32. Disclosed herein are certain structural requirements for performing the disclosed functions, and it is understood that there are a variety of structures which can perform the same function which are related to the disclosed structures, and that these structures will ultimately achieve the same result, for example stimulation or inhibition.

L. KITS

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include Lyp-1 and gC1q/p32 receptors.

M. MIXTURES

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

N. SYSTEMS

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated.

O. COMPUTER READABLE MEDIA

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

P. PEPTIDE SYNTHESIS

The compositions disclosed herein and the compositions necessary to perform the disclosed methods can be made using any method known to those of skill in the art for that particular reagent or compound unless otherwise specifically noted.

One method of producing the disclosed proteins, such as SEQ ID NO:1, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Methods

Disclosed are methods of interacting compositions with gC1qR/p32. Such interactions can be, for example, selective, targeted or homing. Interaction with gC1qR/p32 can be mediated by Lyp-1 and can involve any Lyp-1 or Lyp-1 composition as described herein. Interaction with gC1qR/p32 can be useful for detecting and/or treating diseases and conditions, such as diseases and/or conditions associated with gC1qR/p32.

Disclosed herein are methods of treating a disease associated with gC1q/p32 receptor comprising identifying a subject having a disease associated with the gC1q/p32 receptor; and administering to the subject a composition comprising SEQ ID NO:1 (Lyp-1).

Also disclosed are methods of treating a disease associated with gC1q/p32 receptor comprising identifying a subject having a disease associated with the gC1q/p32 receptor; and administering to the subject a composition that interacts with the gC1q/p32 receptor in the same location as Lyp-1, thereby treating a disease associated with the gC1q/p32 receptor. The composition that interacts with the gC1q/p32 receptor can be, for example, an antibody, protein, or chemical.

Disclosed are methods of delivering a Lyp-1 composition to a gC1q/p32 receptor, wherein the Lyp-1 composition comprises a moiety linked to a composition comprising SEQ ID NO:1; wherein the method comprises bringing into contact the Lyp-1 composition and a cell, thereby delivering the Lyp-1 composition to the gC1q/p32 receptor.

In one example, the cell is in a subject. When the cell is in a subject, the cell can be selected for its potential to comprise a gC1q/p32 receptor by detecting the presence of gC1q/p32 receptor on another cell of the subject.

Also disclosed are methods of delivering a Lyp-1 composition to a gC1q/p32 receptor, wherein the Lyp-1 composition comprises a moiety linked to a composition comprising SEQ ID NO:1; comprising: selecting a cell for its potential to comprise a gC1q/p32 receptor; and bringing into contact the Lyp-1 composition and the cell, thereby delivering the Lyp-1 composition to the gC1q/p32 receptor.

Also disclosed are methods of detecting interaction between a gC1q/p32 receptor and a Lyp-1 composition, wherein the Lyp-1 composition comprises a moiety linked to a composition comprising SEQ ID NO:1, the method comprising: selecting a cell for its potential to comprise a gC1q/p32 receptor; bringing into contact the Lyp-1 composition and the cell; and detecting interaction between the gC1q/p32 receptor and the Lyp-1 composition.

Disclosed are methods of determining and/or assessing gC1q/p32 receptor level in a cell of a subject, comprising: bringing into contact a cell of the subject and a Lyp-1 composition comprising a detectable agent linked to a composition comprising SEQ ID NO:1; and detecting the level of Lyp-1 composition interacting with gC1q/p32 receptor, thereby determining and/or assessing gC1q/p32 receptor level in the cell. The level of gC1q/p32 receptor in the subject is compared to a previous measurement in the same subject, or can be compared to a control level or standard level.

Also disclosed are methods of identifying a subject having a disease associated with gC1q/p32 receptor, the method comprising bringing into contact a cell of the subject and a Lyp-1 composition, wherein the Lyp-1 composition comprises a moiety linked to a composition comprising SEQ ID NO:1; and detecting interaction between gC1q/p32 receptor and the Lyp-1 composition, thereby detecting the presence or level of gC1q/p32 on the cell, wherein the presence or level of gC1q/p32 receptor on the cell identifies the subject as having a disease associated with a gC1q/p32 receptor.

Also disclosed are methods of screening for a compound that interacts with a gC1q/p32 receptor, comprising bringing into contact a test compound, a Lyp-1 composition, and a gC1q/p32 receptor, wherein the Lyp-1 composition comprises SEQ ID NO:1; and detecting unbound Lyp-1 composition, wherein a given amount of unbound Lyp-1 composition indicates a composition that interacts with gC1q/p32 receptor. The Lyp-1 composition can comprise a moiety, wherein the moiety comprises SEQ ID NO:1. In one example, the moiety can be a detectable agent. Methods of screening are discussed in more detail below.

Further disclosed herein is a method of treating or preventing a disease in a subject associated with gC1q/p32 receptor, the method comprising administering to the subject a composition that modulates gC1q/p32 receptor expression or activity, thereby treating a disease in a subject associated with the gC1q/p32 receptor. The subject can have cancer. The composition can have a therapeutic effect on the cancer. The size of a tumor can be reduced. The growth of a tumor can be reduced, stopped or reversed.

Expression or activity of the gC1q/p32 receptor can be inhibited. This can occur by the use of interfering nucleic acid, such as shRNA or siRNA. Activity of the gC1q/p32 receptor can be inhibited by LyP-1 peptide, an antibody, or a small molecule mimic of Lyp-1. Examples of these can be found in FIG. 10 and Example 2. The methods of treating or preventing cancer disclosed herein can be used in conjunction with other treatment therapies as well.

The therapeutic effect of the composition disclosed above can be a slowing in the increase of or a reduction of tumor burden. This slowing in the increase of, or reduction in the tumor burden, can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement in the increase of, or reduction in the tumor burden of, compared with a non-treated tumor, or a tumor treated by a different method.

The gC1q/p32 receptor involved in the disclosed methods can be, for example, on or in a cell. The cell can be in any context, such as in an organism, in situ, ex vivo, in culture, and/or in vitro.

The disclosed compositions can be used to treat any disease where uncontrolled cellular proliferation occurs such as cancers. A non-limiting list of different types of cancers can be as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Example 1

Lyp-1 and gC1qR/p32

Figure 1B:
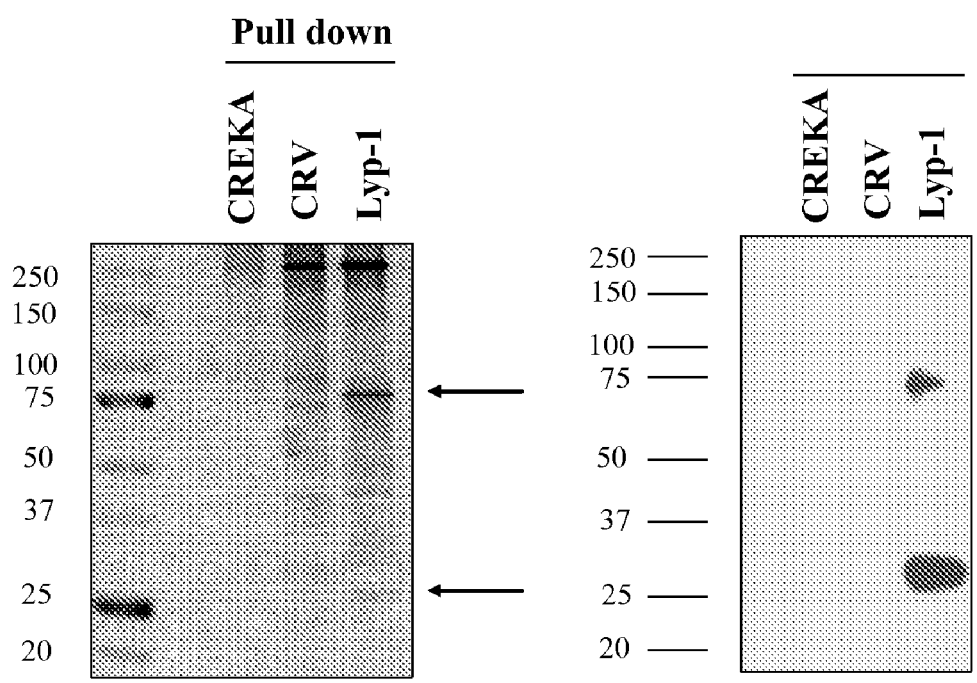

Interaction of Lyp-1 with gC1qR/p32 was demonstrated in a pull down assay. Pull down assays were performed with biotinylated Lyp-1 peptide (SEQ ID NO:1, CGNKRTRGC) from protein extracts derived from MDA-MB-435 cultured cells or MDA-MB-435 tumor xenografts. A tumor homing peptide, CREKA (SEQ ID NO:3), and a peptide CRV which resembles Lyp-1 in its amino acid composition and cyclic structure (SEQ ID NO:4, CRVRTRSGC), were used as negative controls. The Lyp-1 bound proteins were visualized using silver staining and immunoblotting. The left panel of FIG. 1(a) shows the results of silver staining. The arrow indicates a specific 33 kD band, which was identified as gC1qR/p32 by mass spectrometry. The right panel of FIG. 1(a) shows the results of immunoblotting of total cell extract (Tot lysate) and proteins bound to Lyp-1 and control peptides using a monoclonal antibody against gC1qR/p32. The antibody recognizes a band of 33 kD in the total proteins lysate and in the Lyp-1 pull down. Anti gC1qR/p32 reactive bands are not detected in the pull downs from both control peptides. The left panel of FIG. 1(b) shows the results of silver staining of proteins pulled down from MDA-MB-435 tumor xenografts by Lyp-1 peptide, revealed an additional 75 kD band, which was also identified as gC1qR/p32 by mass spectrometry. The right panel of FIG. 1(b) shows the results of immunoblotting. The monoclonal antibody against gC1qR/p32 recognized a 75 kD and a 33 kD band only in the Lyp-1 peptide pull down.

Lyp-1 expressing phage was shown to specifically bind to purified gC1qR/p32 protein. Purified gC1qR/p32 or BSA, as a control, were coated onto microtiter wells (5 µg/ml) and targeted for binding with 108 pfu of insertless phage, Lyp-1 phage, or control phage carrying another tumor homing peptide (CREKA, SEQ ID NO:3). After 16 hours of incubation at 37° C., bound phages were eluted and quantified by plaque assay. The results are show in FIG. 2(a). Results are expressed as fold of Lyp-1 and CREKA (SEQ ID NO:3) phages recovered over insertless phage and are representative of five independent experiments.

An antibody against the N-terminus of gC1qR/p32 was shown to inhibit Lyp-1 phage binding to purified gC1qR/p32. The left panel of FIG. 2(b) shows a diagram of precursor (aa 1-282) and mature (aa 74-282) gC1qR/p32 protein. Boxes indicate the amino acid residues recognized by the monoclonal antibodies, mAb 60.11 and mAb 74.5.2, respectively at the N-terminus (aa 76-93) and C-terminus (aa 204-282) of the mature protein. The amino acid sequence recognized by mAb 60.11 is also indicated. $1.5 \times 10^7$ pfu of insertless and Lyp-1 phages were allowed to bind for 6 hours at 37° C. to gC1qR/p32 protein coated onto microtiter plates in the presence or absence of 20 µg/ml of either mAbs 60.11, 74.5.2 or purified mouse IgG1 (mIgG). The results are shown in the right panel of FIG. 2(b). The results are representative of three independent experiments and are expressed as percentage of phage binding, with Lyp-1 phage binding alone as 100%.

gC1qR/p32 protein levels and cell surface expression was measured in cultured tumor cells and tumor xenografts. Lysates of different tumor cell lines were subjected to Western blot analysis for gC1qR/p32. Actin was used as loading control. C8161 melanoma cells and HL-60 promyelocitic leukemia cells, both low binders of Lyp-1 phage (Laakkonen et al., 2002), express low levels of gC1qR/p32 compared to MDA-MB-435 and BT549 breast cancer cells which exhibit higher Lyp-1 phage binding ability (see FIG. 4(a)). (b-c) FACS analysis was used to detect the cell surface expression of gC1qR/p32 in tumor cell cultures (FIG. 4(b)) or primary cell suspensions from MDA-MB-435 tumor xenografts (FIG. 4(c)). Propidium iodide negative (living) cells were gated for the analysis. In cell suspensions from MDA-MB-435 tumor xenografts, polyclonal anti-gC1qR/p32 antibody causes a significant shift of the FACS peak compared with the rabbit IgG control (see FIG. 4(c)). The cell surface expression of gC1qR/p32 is low in cultured MDA-MB-435 and BT549 cells (see FIG. 4(b)). MDA-MB-435 S35, a MDA-MB-435 subclone with higher Lyp-1 phage binding ability, exhibits a bigger shift of the FACS peak compared to the parental MDA-MB-435 cells. gC1qR/p32 is not expressed on the cell surface in C8161 cells.

gC1qR/p32 overexpression was shown to enhance Lyp-1 phage binding to C8161 melanoma cells. C8161 cells were transiently transfected with pEGFP (2 µg) together with either pcDNA3 or pcDNA3gC1qR/p32 (10 µg). 22 hours post transfection cells were sorted for EGFP expression. The two sorted populations were used for phage binding assay and Western blot analysis to detect gC1qR/p32 overexpression. The results are shown in FIG. 5. Lyp-1 phage binding to empty vector or gC1qR/p32 transfected cells is expressed as fold of binding over insertless phage. The graph represents the mean fold of binding of two independent experiments performed in duplicate.

RNAi-mediated gC1qR/p32 silencing was shown to decrease Lyp-1 peptide binding to the cell surface. MDA-MB-435 cells were transiently transfected with gC1qR/p32-specific or control siRNAs. 48 hours after transfection, inhibition of gC1qR/p32 expression was checked by Western blot analysis and immunostaining. β-actin was used as a control. gC1qR/p32 silencing visibly reduced gC1qR/p32 in both the Western blot and in immunostaining. gC1qR/p32 cell surface expression in control and gC1qR/p32-siRNA transfected cells was determined by FACS analysis on living (propidium iodide negative) cells. Rabbit IgG were used as staining control. gC1qR/p32 silencing reduced cell surface expression to be the same as the control. gC1qR/p32 or control siRNA transfected cells were incubated for 1 hour at 4° C. in the presence of 10 µM FITC conjugated Lyp-1 peptide or a control peptide-ARAL-which has same amino acid charge (ARALPSQRSR, SEQ ID NO:5) and exhibits less binding ability (first graft on the left). The amount of fluorescence in living cells was analyzed by FACS. Cells incubated in the absence of peptide served as FITC negative control. Compared to control siRNA transfected cells, down-regulation of gC1qR/p32 expression (in the presence of gC1qR/p32 siRNA) caused a shift in the peak of Lyp-1 fluorescence but not control peptide fluorescence. Detection of the control peptide showed no difference in the cells exposed to the gC1qR/p32 siRNA and the control siRNA.

Tumor localization of gC1qR/p32 and Lyp-1 peptide were visualized. gC1qR/p32, lymphatic or blood vessels, podoplanin and Meca32/CD31 were stained with fluorescently-labeled antibodies in MDA-MB-435 tumor xenografts. Polyclonal anti-gC1qR/p32 antibody recognizes cell clusters that lack blood vessels but contain lymphatics, or cells lining vessel-like structures positive for Podoplanin but not CD31 or Meca32. Fluorescein-conjugated Lyp-1 peptide was i.v. injected into mice bearing MDA-MB-435 tumors and allowed to circulate for 1 hour before removal of the tumor for gC1qR/p32 immunohistochemical analysis. Lyp-1 peptide localizes in gC1qR/p32-positive patches within the tumor.

Example 2

The Mitochondrial/Cell Surface Protein p32/gC1qR Regulates the Balance Between Glycolysis and Oxidative Phosphorylation in Tumor Cells i. Introduction A tumor homing peptide, LyP-1, selectively binds to tumor-associated lymphatic vessels and tumor cells in certain tumors and exhibits an anti-tumor effect. It is herein shown that the multi-ligand, multi-compartment protein p32/gC1qR is the receptor for LyP-1. The LyP-1 peptide specifically bound gC1qR/p32 from extracts of cultured tumor cells, and gC1qR/p32 co-localized with intravenously injected LyP-1 in tumor lymphatics and in cells positioned adjacent to these vessels. Immunohistochemical analysis of human tissues revealed greatly elevated expression of gC1qR/p32 in several cancers relative to corresponding normal tissues. Knocking down gC1qR/p32 expression with shRNA elevated glycolysis and decreased mitochondrial respiration in MDA-MB-435 tumor cells. Surprisingly, the knockdown compromised the ability of the tumor cells to survive and proliferate in low glucose conditions and severely diminished their tumorigenicity in vivo. Restored expression of gC1qR/p32 reversed these changes.

Tumors can be distinguished from their non-malignant counterparts by specific molecular signatures expressed in malignant cells and tumor vasculature. Tumor associated antigens such as certain growth factor and cytokine receptors, membrane-type matrix metalloproteinases, and cell adhesion molecules are highly expressed in many tumors. Similarly, biochemical features that distinguish tumor vasculature from the vasculature of normal tissues include the expression of various angiogenesis-related molecules (Ruoslahti, 2002; St Croix et al., 2000). Tumor lymphatics are also specialized, since they express markers that are not present in the lymphatics of normal tissues (or in tumor blood vessels) (Laakkonen et al., 2002; Zhang et al., 2006). The markers in tumor blood vessels and lymphatics can vary between tumor types, and the marker profile of the vessels changes as tumorigenesis advances from premalignant lesions to fully malignant tumors (Hoffman et al., 2003; Joyce et al., 2003; Zhang et al., 2006).

The distinct protein profile of tumor vessels and tumor cells can be exploited in ligand-directed (synaphic) targeting of diagnostic therapeutic agents. Targeting can improve the specificity and efficacy of a compound while reducing side effects (Arap et al., 2002; Arap et al., 1998b; Jain, 1998). This partial success emphasizes the need to find new molecules that recognize selectively expressed markers in tumors.

In vivo screening of phage libraries that display random peptide sequences on their surface has yielded a number of specific homing peptides for tumor vasculature and tumor cells (Arap et al., 1998a; Porkka et al., 2002). Identification of receptors for homing peptides provides new tumor markers, and may also reveal signaling pathways that, if interrupted, affect tumor growth/malignancy. LyP-1, a cyclic nonapeptide that specifically recognizes lymphatic vessels in certain tumors (Laakkonen et al., 2002), is a case in point. Lymphatic vessels are an important conduit for the spread of solid tumors, and their abundance in and around tumors correlates with propensity to metastasize (Alitalo et al., 2004; Stacker et al., 2002).

The LyP-1 peptide provides a marker for these vessels, but also binds to tumor cells, offering the ability to selectively target both tumor lymphatics and tumor cells. Moreover, the target molecule (receptor) for the LyP-1 peptide appears to be involved in tumor growth because systemic administration of LyP-1 inhibits tumor growth in mice (Laakkonen et al., 2004). LyP-1 appears to be cytotoxic against tumor cells undergoing stress, as LyP-1 accumulation coincides with hypoxic areas in tumors and tumor starvation enhances its binding and internalization in cultured tumor cells (Laakkonen et al., 2004). These unique properties of the LyP-1 system prompted the search for the tumor cell receptor for this peptide.

In this study, p32/p33/gC1qR/HABP1 (p32) has been identified as the cellular receptor for LyP-1. This protein was originally isolated based on its co-purification with the nuclear splicing factor SF-2 (Krainer et al., 1991). It was also found to bind to the globular heads of the C1q protein and was therefore designated the gC1q/p32 receptor (gC1qR/p32) (Ghebrehiwet et al., 1994). Plasma proteins and extracellular matrix components, such as kininogen, factor XII, vitronectin and hyaluronic acid, have been also reported to bind to gC1qR/p32 (Deb and Datta, 1996; Herwald et al., 1996; Joseph et al., 1996; Lim et al., 1996). In addition, gC1qR/p32 interacts with several bacterial and viral proteins, showing its possible role in microbial pathogenesis (Braun et al., 2000; Kittlesen et al., 2000; Matthews and Russell, 1998; Tange et al., 1996).

The gC1qR/p32 protein can be present in diverse cellular compartments depending on the cell type and physiological conditions. This protein has been variously located in mitochondria (Dedio et al., 1998; Matthews and Russell, 1998; Muta et al., 1997), nucleus (Krainer et al., 1991; Majumdar et al., 2002), and at the cell surface (Ghebrehiwet et al., 1994; Gupta et al., 1991; Soltys et al., 2000). It may also be secreted and bound to the extracellular matrix (Herwald et al., 1996; Lim et al., 1996; Rozanov et al., 2002a). The disparate observations on its multiple protein interactions and cellular localization, have left the physiological role(s) of gC1qR/p32 in mammalian cells unclear. In the yeast, the gC1qR/p32 homologue has been reported to regulate oxidative phosphorylation (Muta et al., 1997).

It is herein shown that knocking down gC1qR/p32 expression in tumor cells shift their metabolism toward glycolysis and that, surprisingly, the glycolytic phenotype is associated with impaired tumor cell survival and growth, especially under adverse growth conditions. At the same time, tumorigenicity of the gC1qR/p32 knockdown cells is reduced.

ii. Results a. LyP-1 Peptide Binds to gC1qR/p32 Protein

To identify the receptor for the LyP-1 peptide, biotin-labeled LyP-1 and control peptides were incubated with extracts of MDA-MB-435 cells, a cell line that binds and internalizes LyP-1 (Laakkonen et al., 2004). LyP-1 bound a specific band in the 30 kDa range that was not seen in the controls (FIG. 3A, left panel), which were the pentapeptide CREKA (SEQ ID NO: 3) (Simberg et al., 2007) and the nonapeptide CRVRTRSGC (SEQ ID NO: 4), which resembles LyP-1 in its amino acid composition and cyclic structure. Two independent MALDI-TOF analyses indicated that the specific band represents the mature form of a protein known as gC1qR/p32, a receptor for the globular head of complement component C1q (Ghebrehiwet et al., 2002; Ghebrehiwet et al., 1994). LyP-1 affinity isolation also yielded gC1qR/p32 from cultured BT549 breast carcinoma cells and from extracts of MDA-MB-435 xenograft tumors.

Figure 3A:
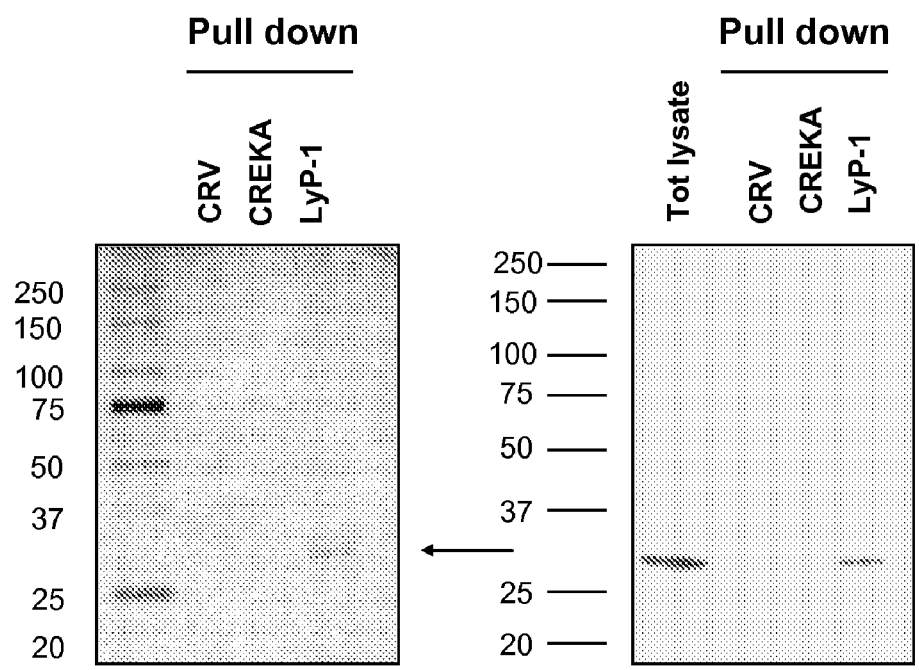
Figure 3B:
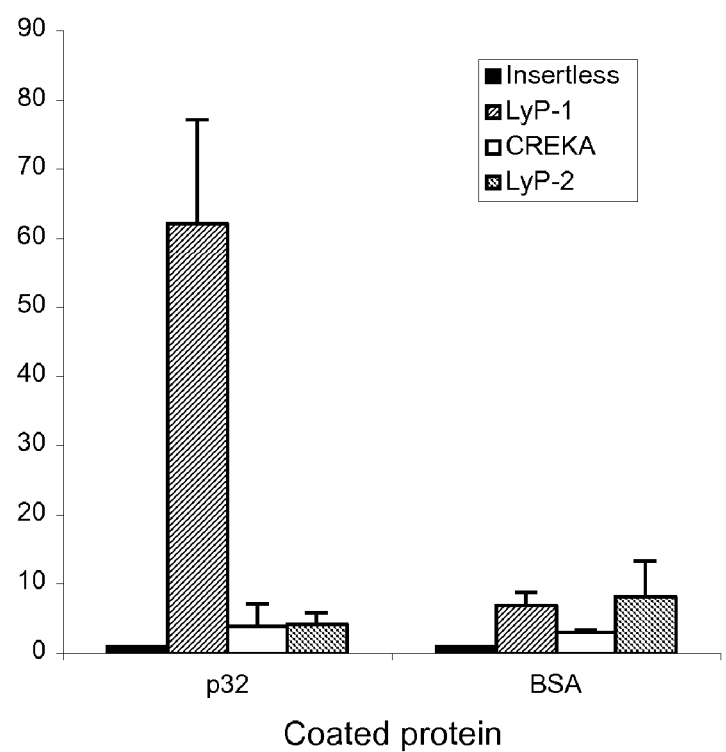
Figure 3C:
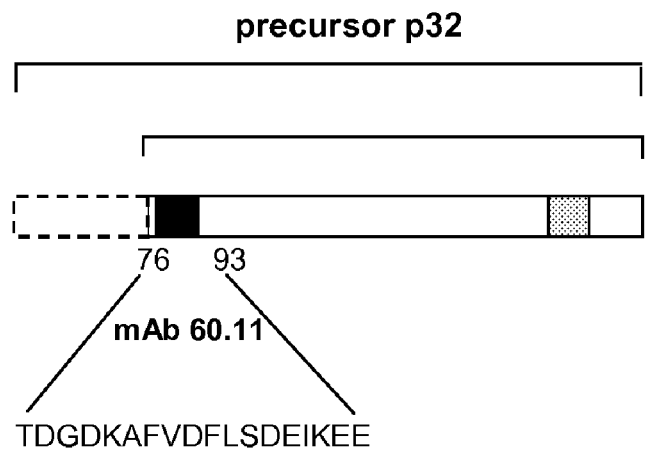
Figure 3D:
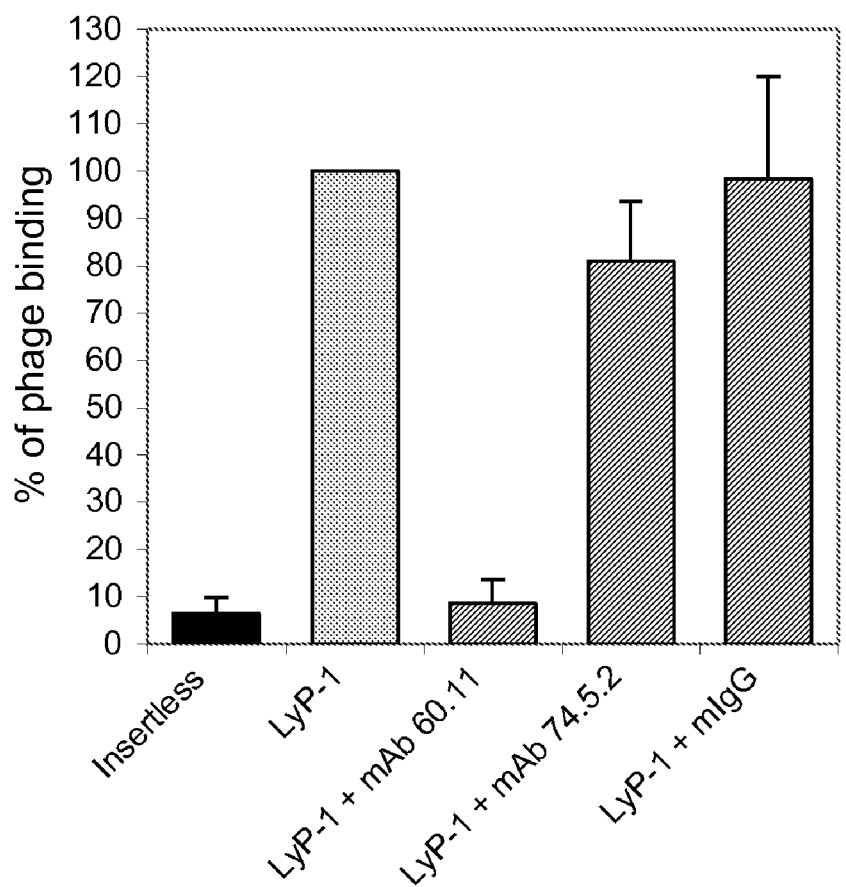

The identification of the LyP-1-binding protein as gC1qR/p32 was confirmed by immunoblotting and phage binding assays. A monoclonal antibody directed against gC1qR/p32 specifically recognized the band (FIG. 3A right panel). No detectable gC1qR/p32 was pulled down by the control peptides. The LyP-1 phage bound to purified gC1qR/p32 protein an average of 60-fold more than insertless control phage, while only marginal binding of either phage to plates coated with BSA was seen (FIG. 3B). LyP-2, a peptide, which shares a consensus sequence with LyP-1 but binds a different spectrum of tumor lymphatics (Zhang et al., 2006), did not significantly bind to gC1qR/p32. A monoclonal antibody, mAb 60.11, which binds to gC1qR/p32 near the N-terminus (amino acids 76-93), reduced LyP-1 phage binding to gC1qR/p32 by 90% (FIG. 3C). In contrast, mAb 74.5.2, which recognizes the C-terminal end of gC1qR/p32 (amino acids 204-218), did not inhibit the phage binding. These results indicate that the interaction between LyP-1 and gC1qR/p32 is specific and that the N-terminus of gC1qR/p32 between amino acids 76 and 93 plays an important role in the interaction.

Figure 4B:
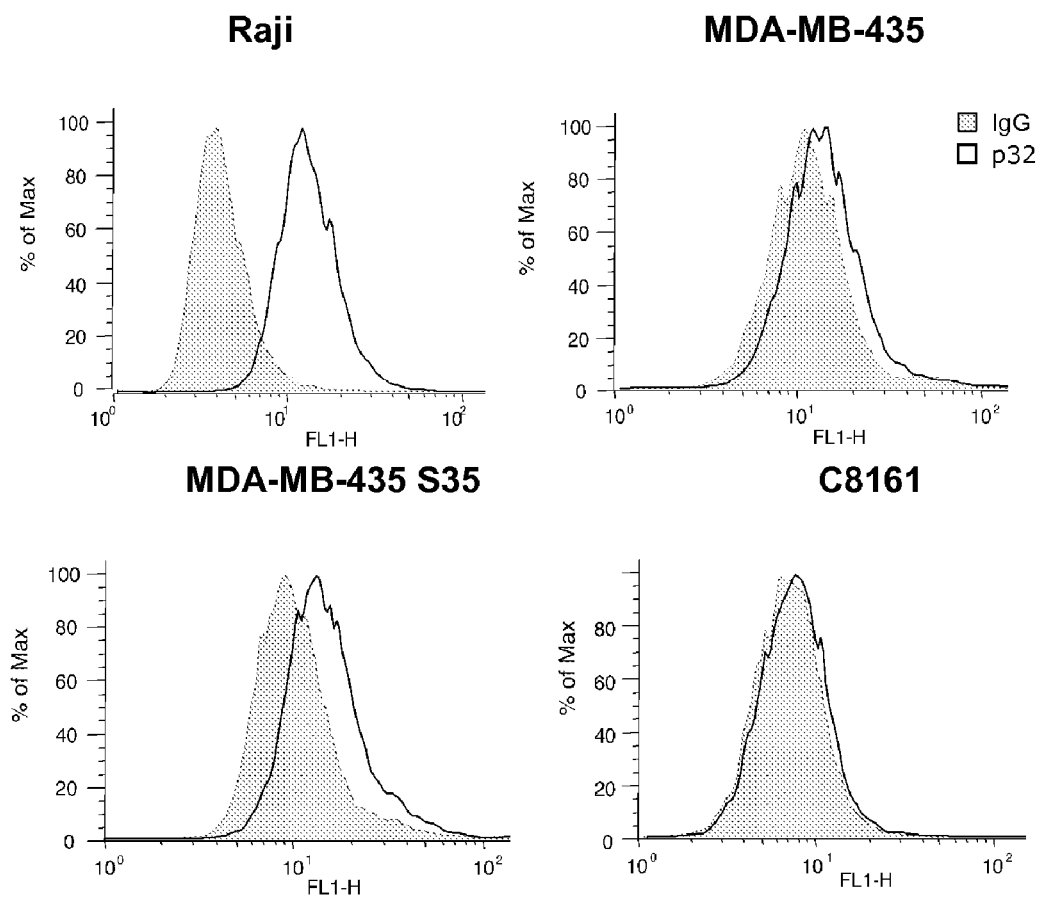
Figure 4C:
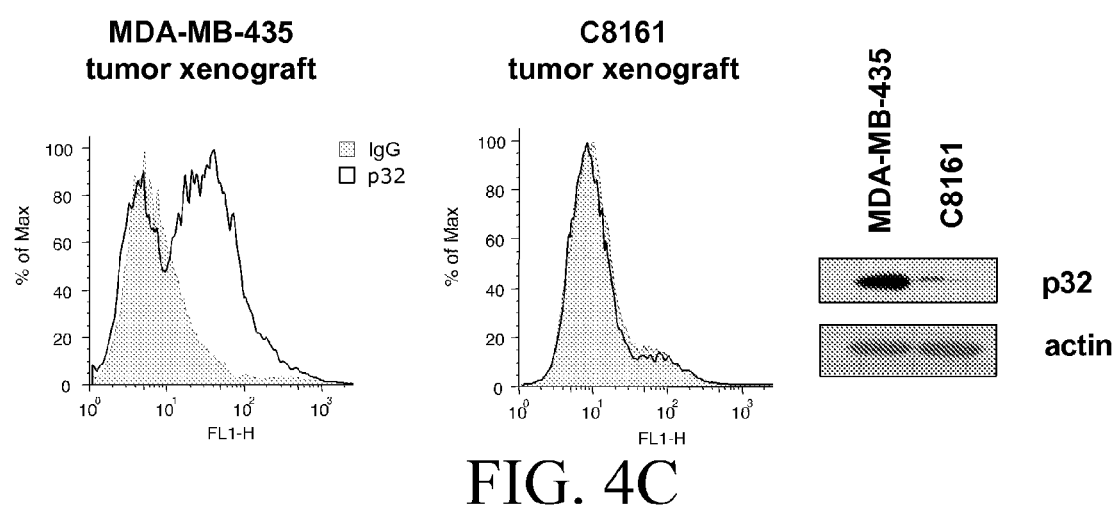

Immunoblotting revealed a correlation between gC1qR/p32 expression and LyP-1 binding in a number of tumor cell lines; HL-60 leukemia cells and C8161 melanoma cells, previously shown not to significantly bind LyP-1 (Laakkonen et al., 2002), expressed low levels of gC1qR/p32 protein, whereas two strong LyP-1 binders, MDA-MB-435 and BT549 ((Laakkonen et al., 2002), expressed abundant gC1qR/p32 (FIG. 4A).

b. The gC1qR/p32 Protein is Expressed at the Cell Surface and Mediates LyP-1 Binding For gC1qR/p32 to act as a LyP-1 receptor, it would have to be expressed at the cell surface. While primarily localized in intracellular compartments (mitochondria, nucleus and cytoplasm), gC1qR/p32 has also been reported to be present at cell surface (Ghebrehiwet et al., 1994; Guo et al., 1999; Peerschke et al., 1994). gC1qR/p32 was also found at the cell surface. A polyclonal anti-gC1qR/p32 antibody produced a small but consistent shift in FACS analysis of live MDA-MB-435 cells (FIG. 4B). A greater shift was obtained in an MDA-MB-435 subclone (S35), which binds LyP-1 with higher efficiency than the parental cell line. Raji Burkitt lymphoma cells were even more strongly positive. Interestingly, the total gC1qR/p32 expression level was similar in the parental MDA-MB-435 and the S35 variant cells (FIG. 4A). Single cell suspensions from MDA-MB-435 tumor xenografts were more strongly positive for cell surface gC1qR/p32 protein than cultured MDA-MB-435 cells, whereas C8161 cells remained essentially negative for LyP-1 binding even as primary tumor cells (FIG. 4C).

Figure 5A:
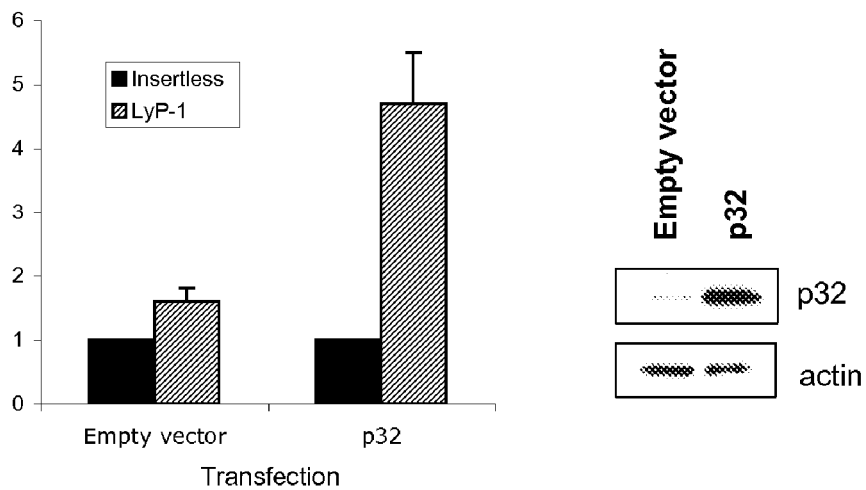
Figure 5B:
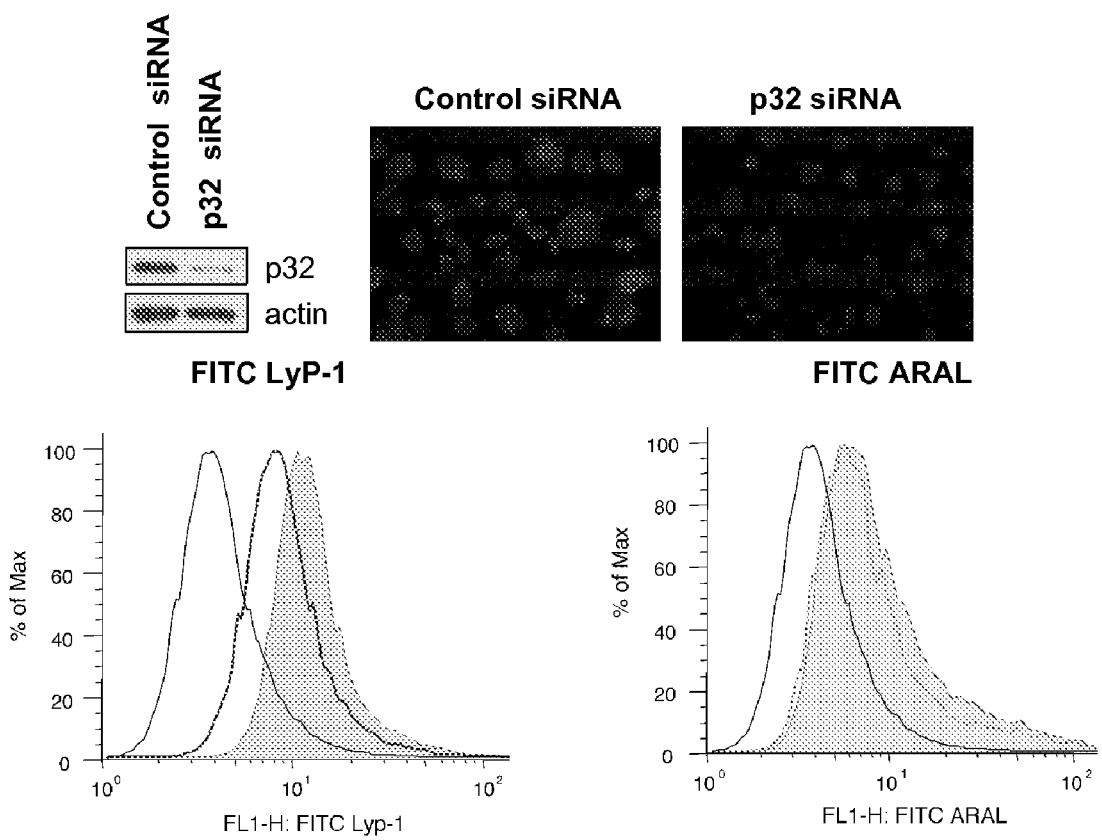
Figure 5C:
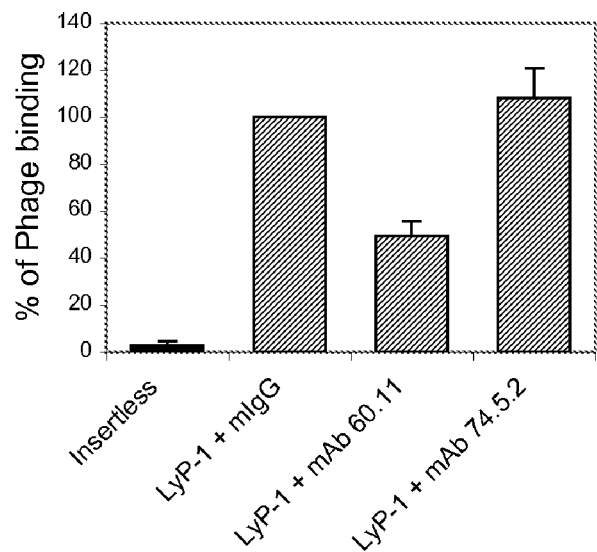

The effect of forced expression and knockdown of gC1qR/p32 on LyP-1 binding was next studied. Transient transfection of C8161 cells with gC1qR/p32 cDNA increased LyP-1 phage binding to 5-fold over control phage (FIG. 5A). A less than 2-fold binding was obtained upon transfection with the empty vector. Transfection with a gC1qR/p32 siRNA construct markedly reduced expression in MDA-MB-435 cells (FIG. 5B, upper left panel), with an accompanying reduction in the binding of FITC-LyP-1 peptide to the cells (FIG. 5B lower left panel). Controls showed that an unrelated siRNA did not affect gC1qR/p32 expression or LyP-1 binding, and neither siRNA changed the expression of β-actin. Also, a control peptide, which like LyP-1 has three basic residues but does not significantly bind to the MDA-MB-435 cells (Laakkonen et al., 2002), gave the same amount of background fluorescence in the gC1qR/p32 knockdown and control cells (FIG. 5B, lower right panel). Finally, blocking gC1qR/p32 with mAb 60.11 in Raji cells (which express high levels of cell surface gC1qR/p32) reduced LyP-1 binding to these cells by 50%, while the phage binding was unaffected by mAb 74.5.2 (FIG. 5C). These results are consistent with those obtained with purified gC1qR/p32 protein (FIG. 3C) and indicate that the gC1qR/p32 level expression at the cell surface dictates LyP-1 binding to the cells. They also suggest that cell surface localization of gC1qR/p32 is regulated independently of total gC1qR/p32 expression, and that tumor microenvironment may enhance the cell surface expression.

c. Expression of gC1qR/p32 in MDA-MB-435 Tumor Xenografts and Human Cancers

Figure 6A:
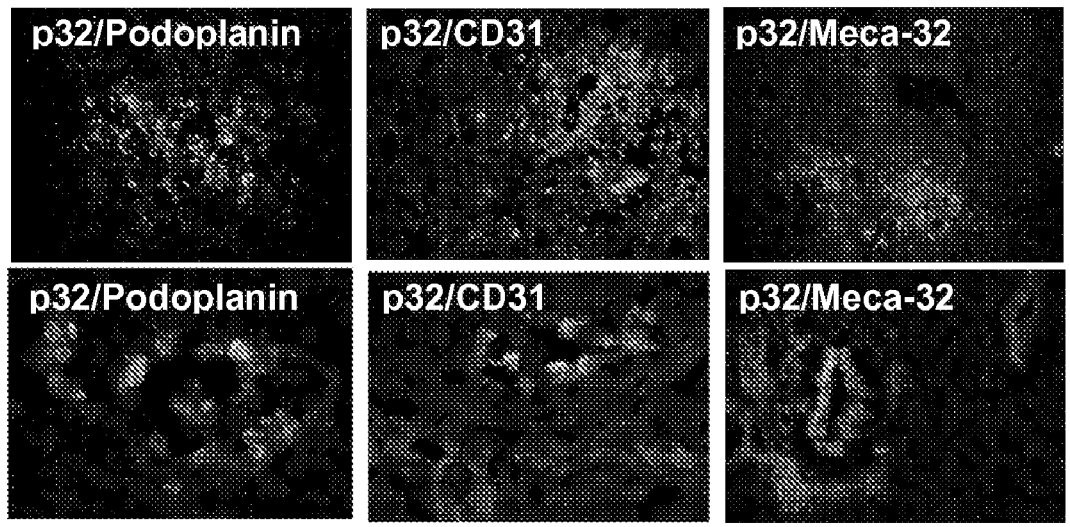
Figure 6B:
Figure 6C:
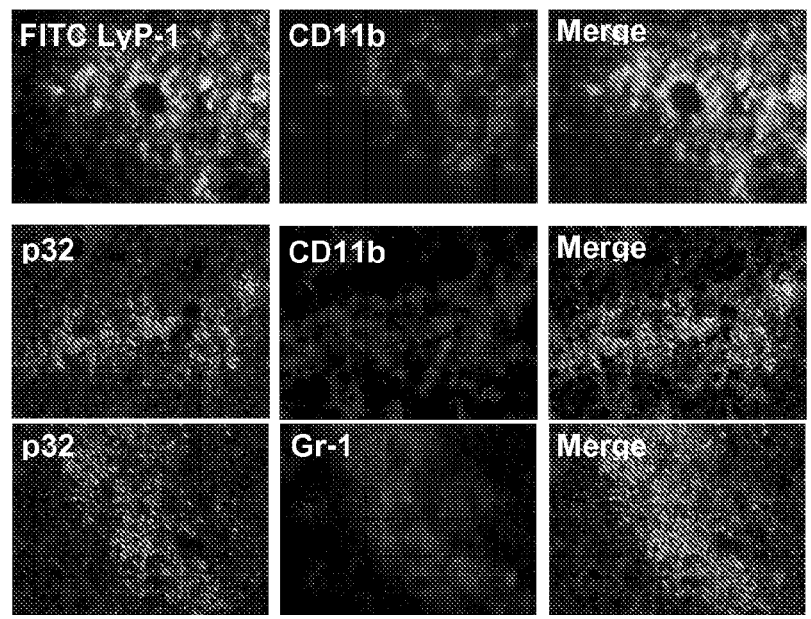
Figure 6D:
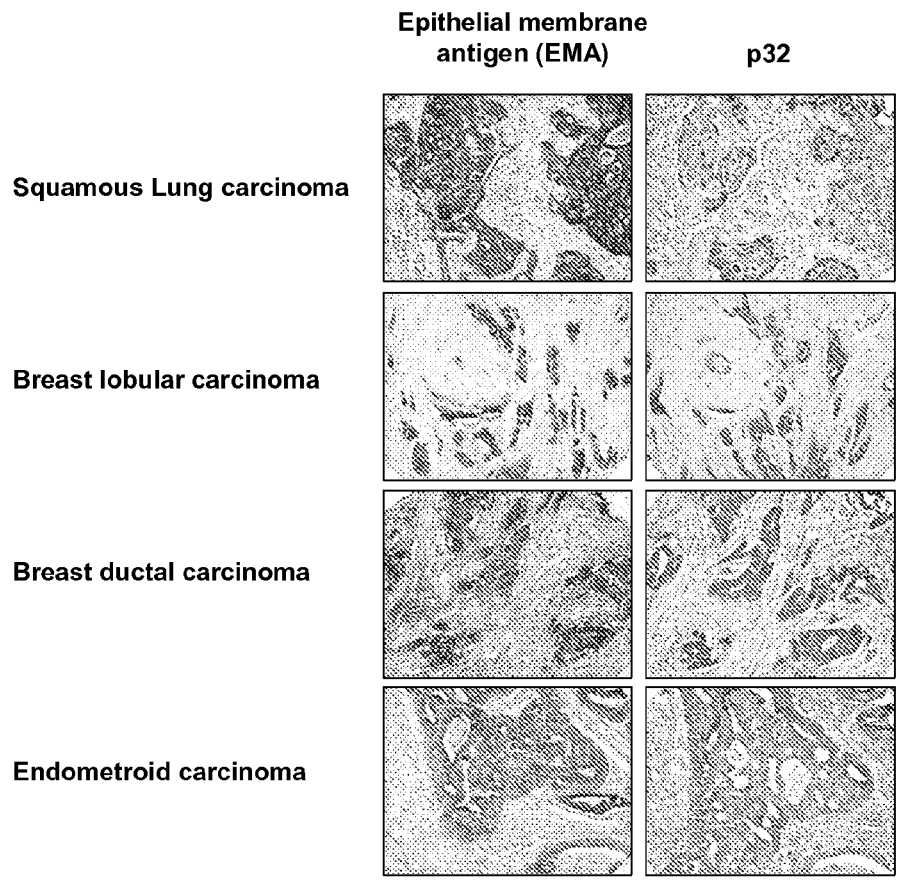

To investigate the localization of gC1qR/p32 in tumors, sections of MDA-MB-435 tumor xenografts were stained for gC1qR/p32 and podoplanin (a lymphatic/macrophage marker). Clusters of cells strongly positive for gC1qR/p32 were found in close proximity to tumor lymphatics, whereas there was no association with blood vessels as visualized by staining for CD31 or Meca-32 (FIG. 6A, upper panels). Cells expressing gC1qR/p32 were also found lining vessel-like structures that were also positive for podoplanin, but not for CD31 or Meca-32 (FIG. 6A, lower panels). Normal tissues and C8161 tumor xenografts showed much less gC1qR/p32 staining than the MDA-MB-435 tumors. Intravenously injected FITC-LyP-1 peptide accumulated in tumor areas with high expression levels of gC1qR/p32 and closely associated with vessel lumens (FIG. 6B). There was a good degree of co-localization of the gC1qR/p32/LyP-1 positive cells and the macrophage markers DC11b and Gr-1 (FIG. 6C). The localization of gC1qR/p32 in the lymphatic areas of tumors confirms the previously noted association of LyP-1 with MDA-MB-435 tumor lymphatics. The gC1qR/p32-positive cells integrated into the lymphatics in these tumors are likely tumor macrophages and/or macrophage-like precursors of lymphatic endothelial cells.

Figure 6E:
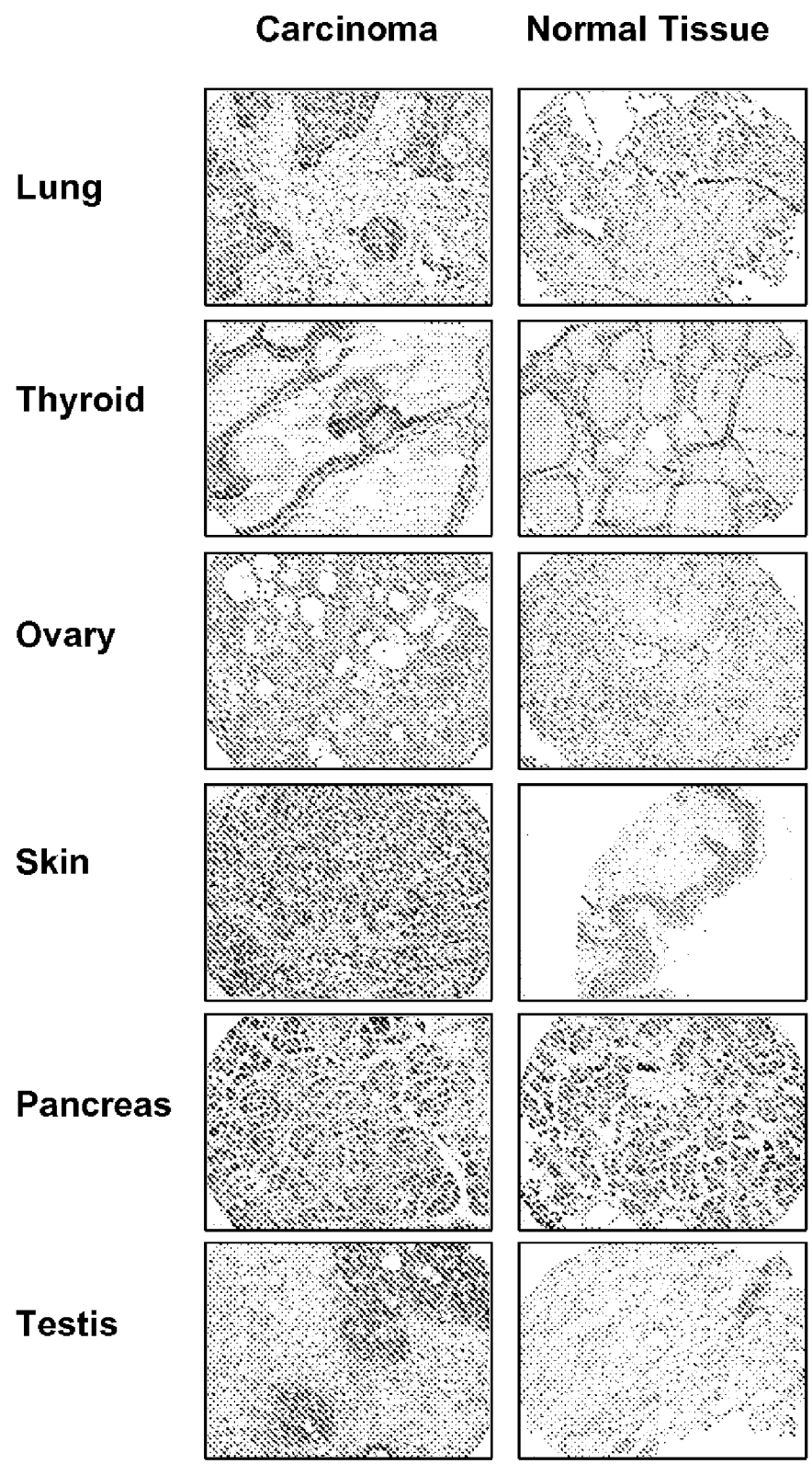

Next, the levels of gC1qR/p32 expression in a variety of human carcinomas were compared by immunohistochemical staining for gC1qR/p32 in clinical samples. The intensity of the staining (FIG. 6D, right panel) was visually scored and compared with a parallel staining for an epithelial membrane antigen in tumor cells (6D, left panel). An immuno-score was assigned to each sample based on the percentage of tumor cells within the tissue and their intensity of gC1qR/p32 staining (Table 1). Compared to non-malignant tissues, several tumor types showed elevated gC1qR/p32 expression levels (FIG. 6E). In particular, breast lobular carcinoma, endometroid adenocarcinoma, melanoma, and carcinomas of the colon and testis, as well as squamous cell carcinomas of the lung, exhibited markedly elevated gC1qR/p32 expression. None of the nine prostate carcinomas examined contained significant gC1qR/p32 levels. The expression of gC1qR/p32 was high in cancers of stomach, pancreas and kidney, but the corresponding non-malignant tissues also expressed gC1qR/p32 at substantial levels. These results confirm and extend previous reports showing preferential expression of gC1qR/p32 by adenocarcinoma cells.

d. Stable Knockdown of gC1qR/p32 Alters Tumor Cell Metabolism and Growth

Figure 7A:
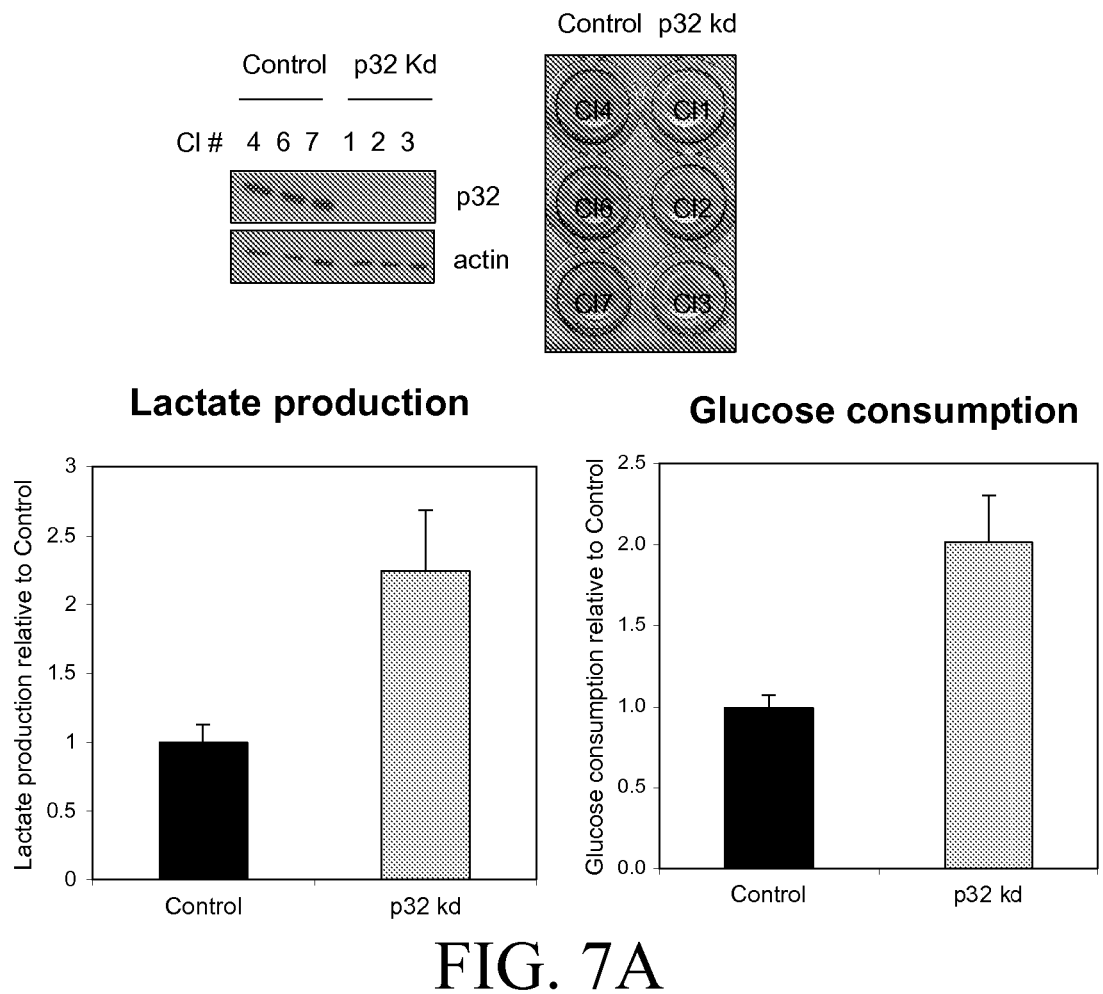

To delineate the role of gC1qR/p32 in tumor physiology shRNA-based knockdown of gC1qR/p32 expression was employed in tumor with subsequent analysis of the cells in vitro and in vivo. shRNAs complementary to gC1qR/p32 or a two-base-pair mismatch control shRNA were expressed in MDA-MB-435 tumor cells. A series of gC1qR/p32 and control shRNA stable clones were screened for gC1qR/p32 expression. Three gC1qR/p32 shRNA clones, with undetectable gC1qR/p32 expression, and three control shRNA clones were selected for analysis (FIG. 7A, upper left panel). Each of the gC1qR/p32 knockdown clones showed markedly reduced uptake of FITC-LyP-1 peptide compared to control clones. Strikingly, gC1qR/p32 knockdown induced acidification of the culture medium, as indicated by a phenol red color change 3-4 days after cell seeding (FIG. 7A upper right panel). Consistent with a decrease in pH, lactate production was significantly increased in gC1qR/p32 knockdown compared to control cells (FIG. 7A lower left panel).

Lactic acid is a byproduct of glycolysis and can accumulate under anaerobic conditions or in cases of mitochondrial dysfunction. The ensuing reliance on glycolysis for ATP production is associated with a high rate of conversion of glucose to lactate and a high rate of glucose uptake. It was found that gC1qR/p32 knockdown cells consumed more glucose than the control clones, indicating increased glycolysis (FIG. 7A lower right panel). However, the elevated glycolytic rate and lactate production was not related to increased cell growth of the gC1qR/p32 knockdown cells, as these cells grew more slowly than the control cells (see FIG. 8 below).

Figure 7B:
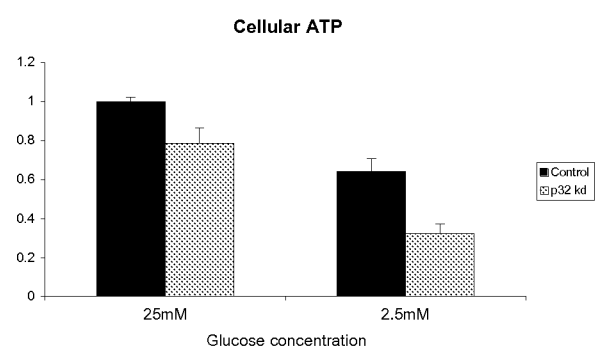
Figure 7C:
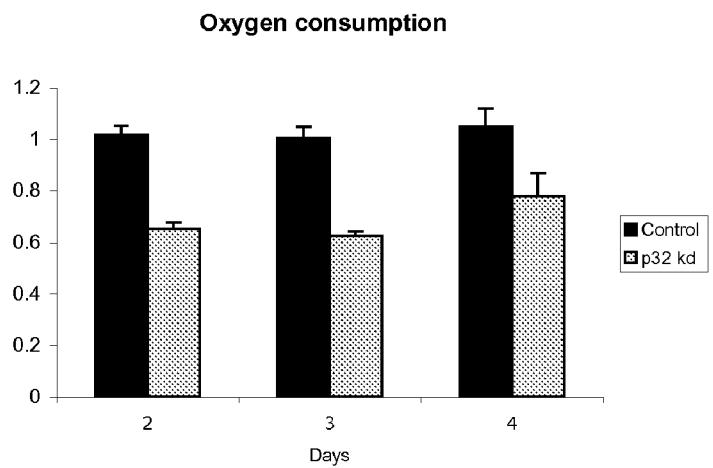

The gC1qR/p32 protein has been found to be present in each of the main cellular compartments, but it is predominantly a mitochondrial protein (Dedio et al., 1998; Jiang et al., 1999; Muta et al., 1997; Soltys et al., 2000; van Leeuwen and O'Hare, 2001). Consistent with a mitochondrial role of gC1qR/p32, a growth defect in yeast lacking the gC1qR/p32 homolog has been linked to an abnormality in maintaining mitochondrial ATP synthesis (Muta et al., 1997). The gC1qR/p32 knockdown cells, when grown in normal media containing high (25 mM) glucose, produced 20% less total ATP than control cells (FIG. 7B). The decrease in mitochondrial ATP production may have been greater than that, as increased ATP production via glycolysis may have compensated for some of the lost mitochondrial ATP synthesis. Reducing glucose concentration in the media to 2.5 mM was more detrimental to cellular ATP production in gC1qR/p32 knockdown (50% reduction) compared to control clones. These data show that gC1qR/p32 can be required for efficient ATP production through oxidative phosphorylation (OXPHOS). Consistent with such a role, gC1qR/p32 knockdown cells consumed less oxygen than control clones (FIG. 7C). Thus, loss of gC1qR/p32 shifts energy metabolism toward glycolysis, likely via perturbation of mitochondrial function.

Figure 7D:
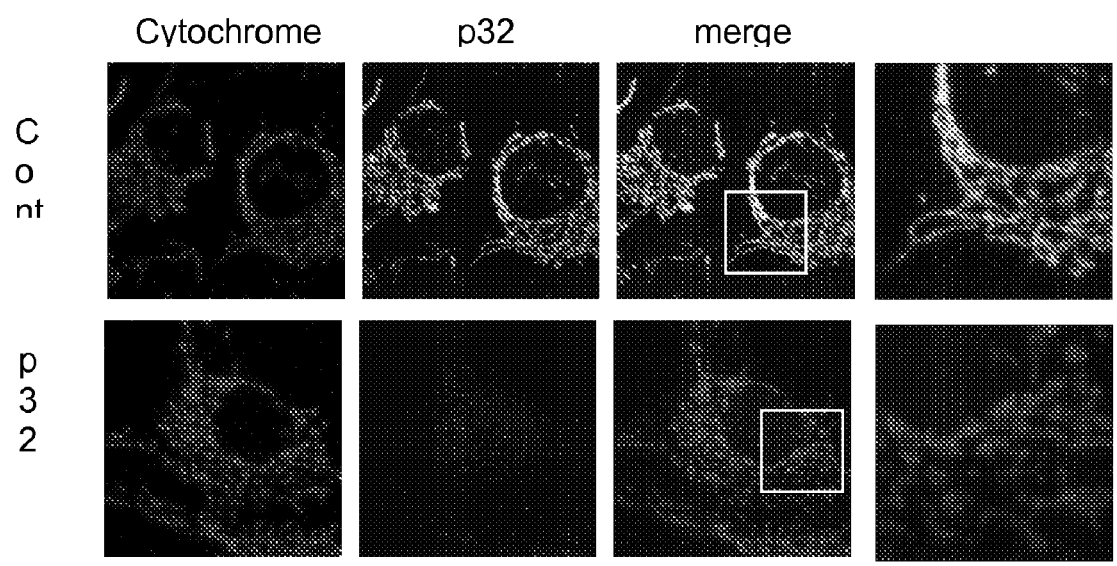

Mitochondrial morphology is closely linked to energy metabolism. Enhanced respiration correlates with an interconnected mitochondrial network and enlarged cristae compartment, while reduced OXPHOS and enhanced glycolysis correlates with fragmented mitochondria and matrix expansion (Alirol and Martinou, 2006). Confocal analysis of mitochondria in gC1qR/p32 knockdown and control clones showed that the mitochondrial network was fragmented rather than fibrillar when gC1qR/p32 was not expressed (FIG. 7D). Taken together, these data support the view that gC1qR/p32 is critical for mitochondrial function, and its inactivation alters energy metabolism in favor of glycolysis.

e. Loss of gC1qR/p32 Impairs Cell Growth and Increases Cell Death

Figure 8A:
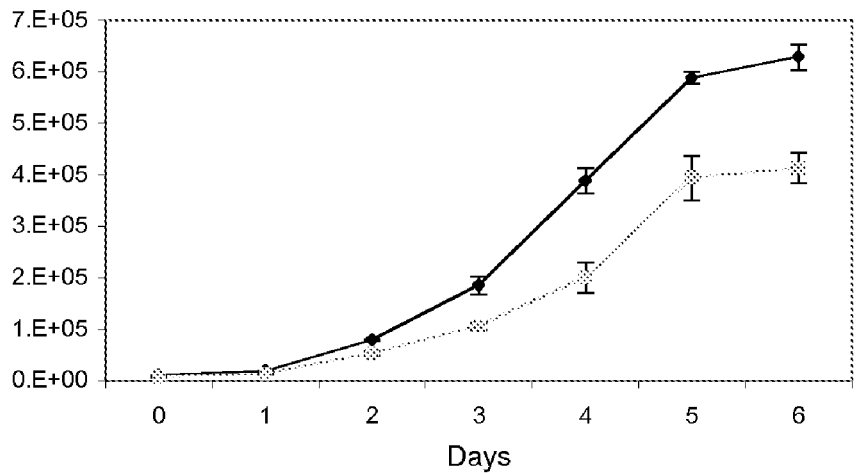
Figure 8A:
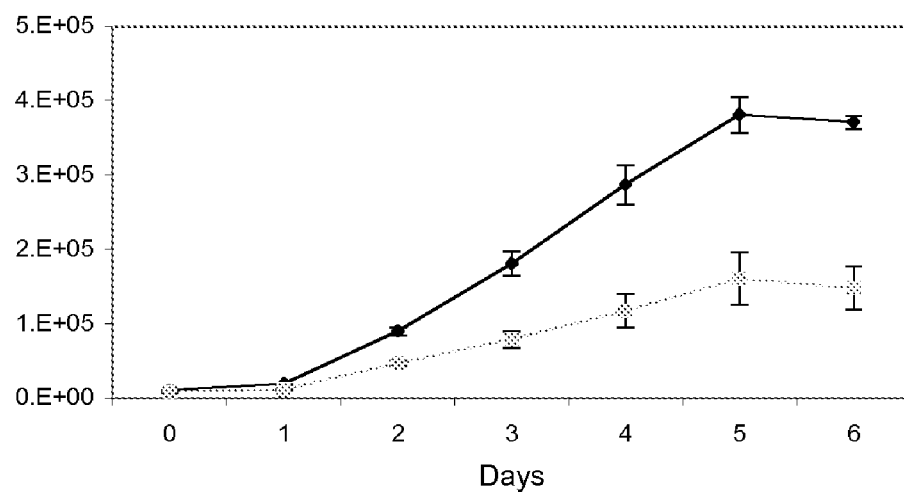
Figure 8A:
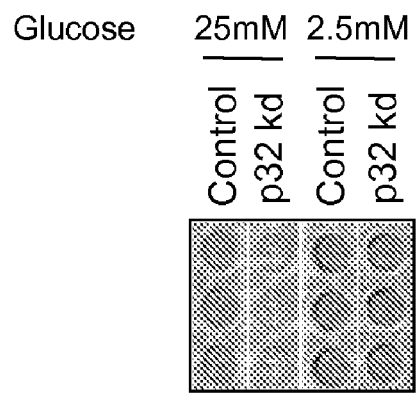

The gC1qR/p32 knockdown cells grew more slowly than control cells (FIG. 8A, left and middle panels). The difference was particularly striking in medium containing only 2.5 mM glucose. Under these low glucose conditions, the medium in the gC1qR/p32 knockdown cells did not become acidic (FIG. 8A, right panel), indicating that the cells were not able to carry out glycolysis at a level that would support cell growth.

Figure 8B:
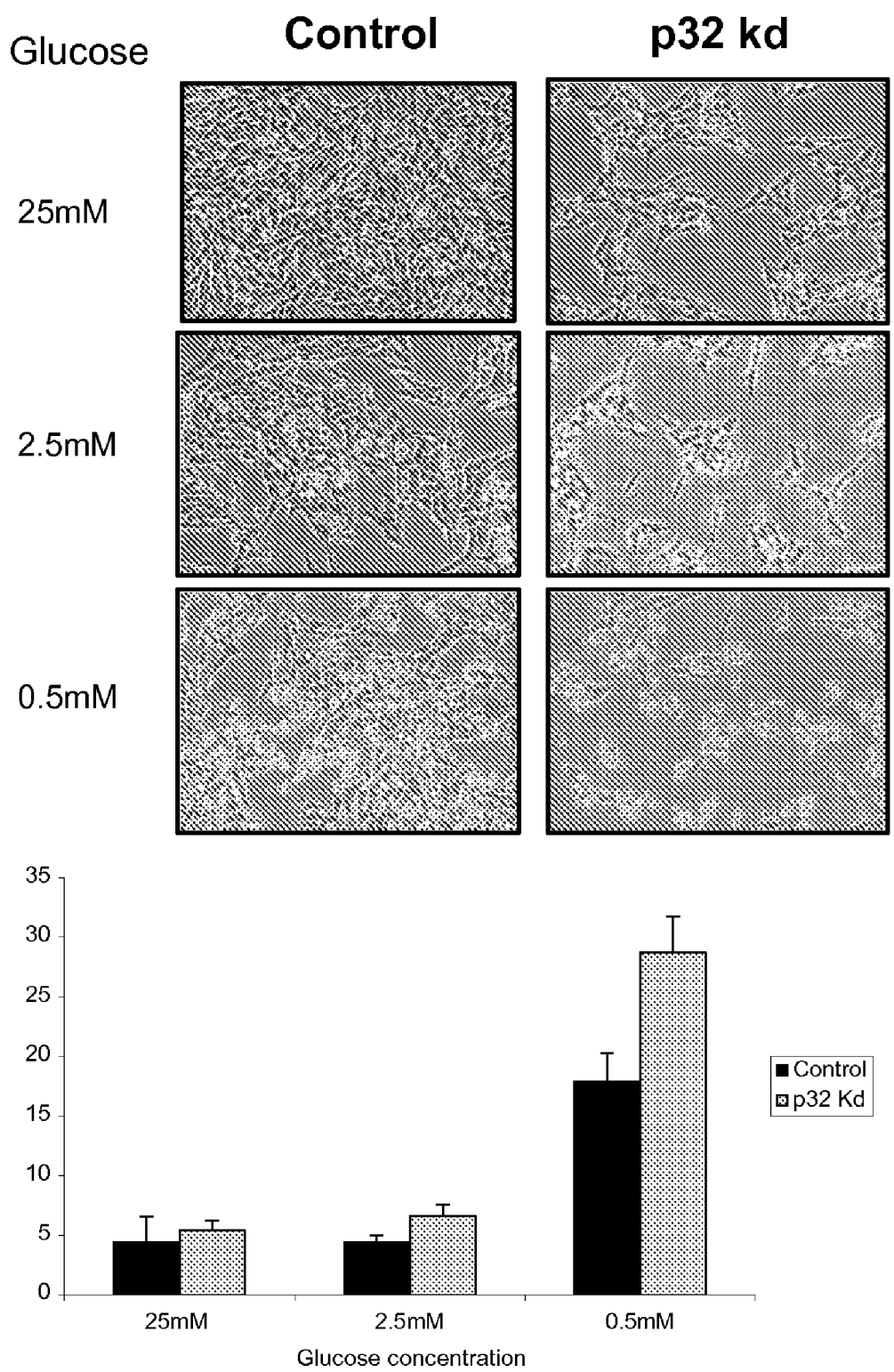

Tumor cells have a tendency to undergo cell death under low glucose conditions (Inoki et al., 2003; Jones et al., 2005). It was next determined whether loss of gC1qR/p32 would confer this trait to the MDA-MB-435 cells. The percentage of annexin V-positive cells in the gC1qR/p32 knockdown and control cells was similar in high glucose media, but a greater sensitivity of the knockdown cells became evident in low glucose media (FIG. 8B).

Figure 8C:
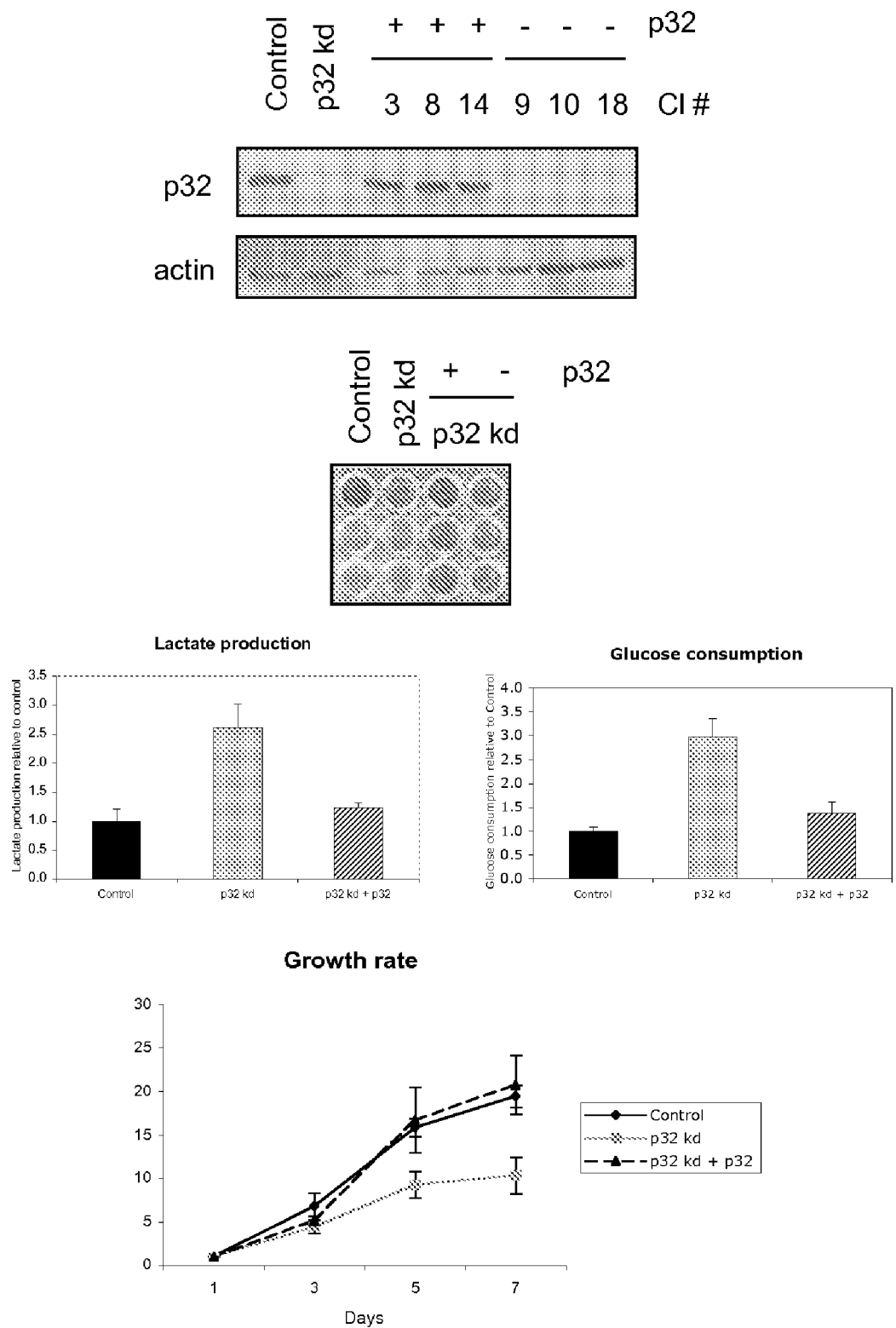

To show the specificity of the shRNA knockdown, gC1qR/p32 production was restored in knockdown cells. A gC1qR/p32 cDNA in which silent mutations confer resistance to inhibition by the gC1qR/p32 shRNA was employed to bring gC1qR/p32 expression to the original level (FIG. 8C). This treatment normalized lactate accumulation, glucose consumption, and proliferation of the knockdown cells (FIG. 8C). These results show that off-target effects are not responsible for the phenotypic effects of the knockdown.

f. Loss of gC1qR/p32 Suppresses Malignancy of Tumor Cells

Figure 9A:
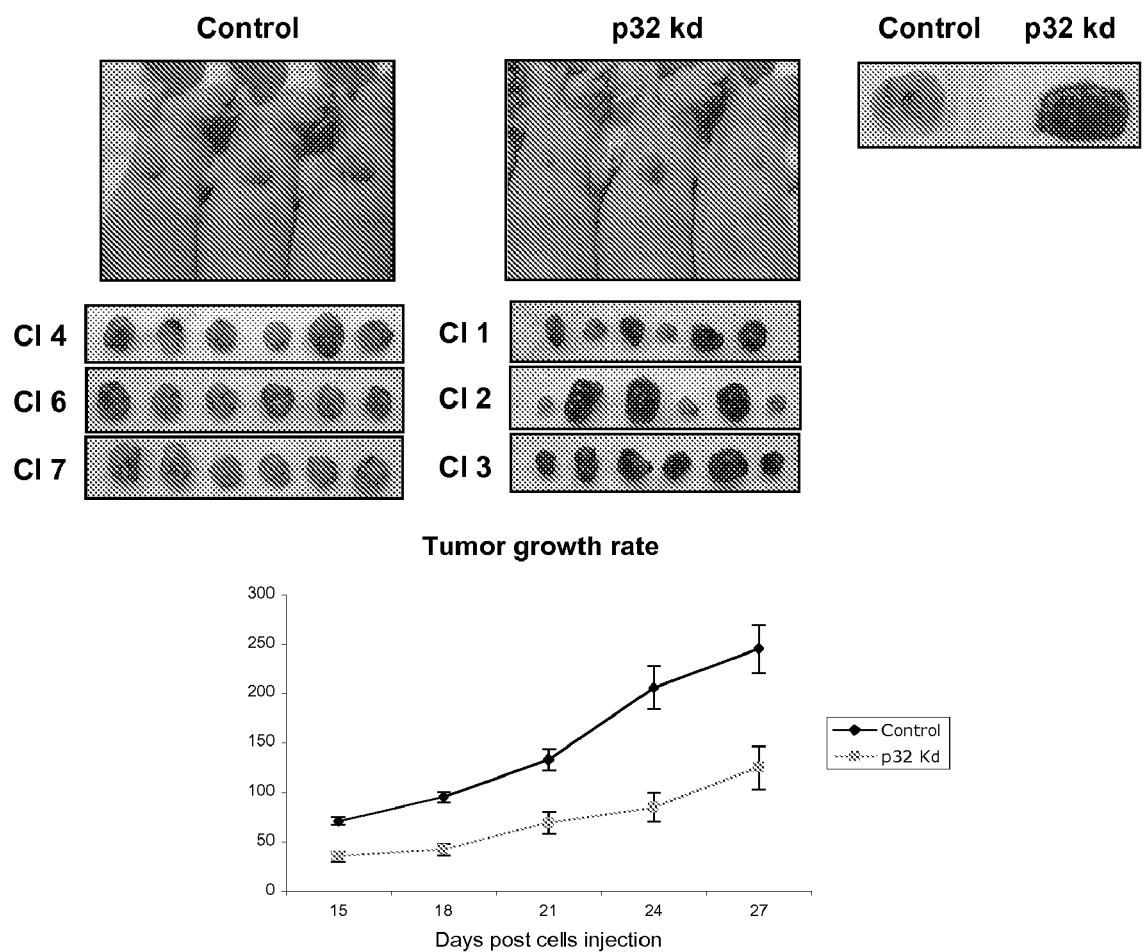
Figure 9B:
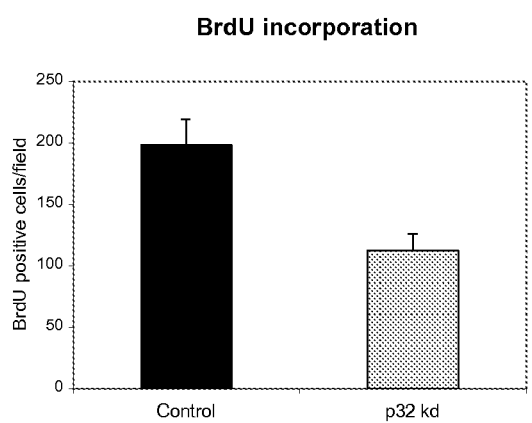
Figure 9C:
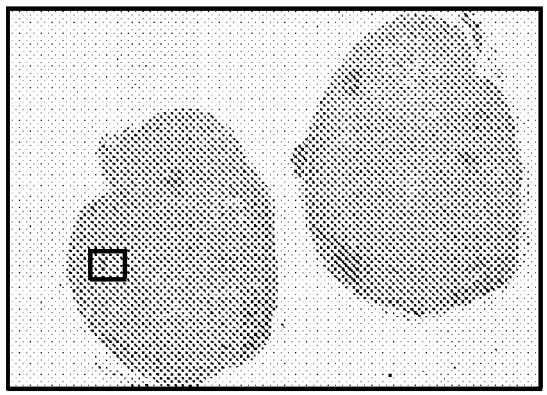
Figure 9C:
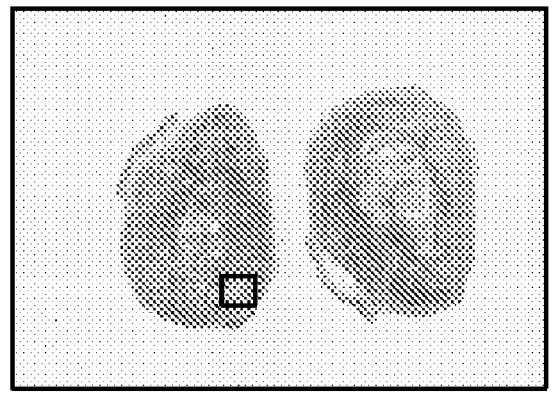
Figure 9C:
Figure 9C:
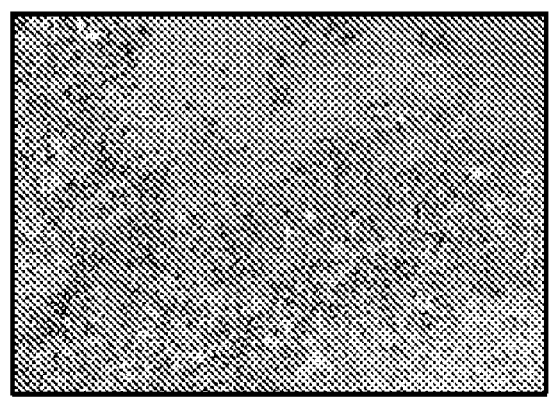
Figure 9C:
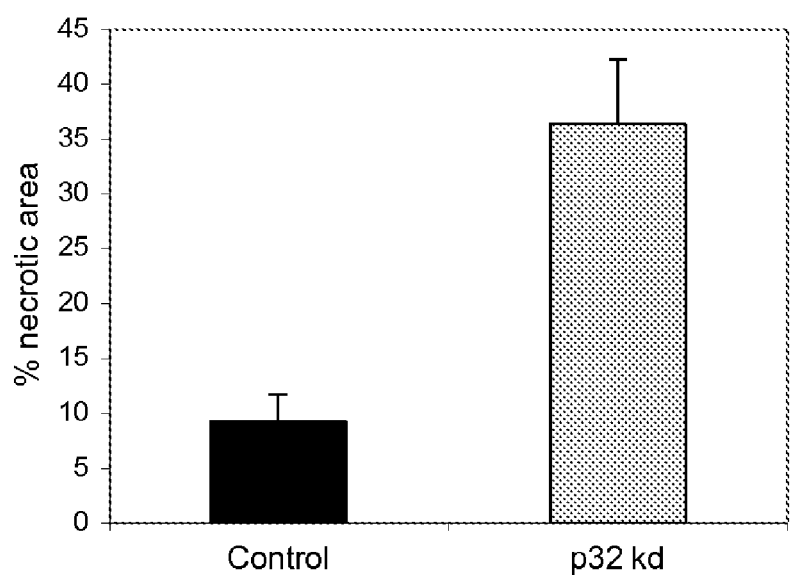

The elevated gC1qR/p32 expression in tumors and impaired proliferation and survival of gC1qR/p32 knockdown cells, prompted the investigation of the role of gC1qR/p32 in tumorigenesis. Control and gC1qR/p32 knockdown cell clones were orthotopically injected into the mammary gland fat pad of nude mice, and tumor growth was monitored. The gC1qR/p32 knockdown cells produced smaller tumors than controls or the tumors were swollen and soft, and purple color and release of blood upon cutting indicated intratumoral hemorrhage (FIG. 9A, left and middle panels). Even with the hemorrhage contributing to the size of the knockdown tumors, the growth rate of these tumors was significantly lower than that of control tumors ($p<0.001$). Assessment of cell proliferation in the tumors by BrdU incorporation showed significantly reduced number of BrdU-positive cells in the gC1qR/p32 knockdown tumors (FIG. 9B), which is consistent with the slow proliferation rate of the knockdown cells in vitro. Histopathological analysis of tumor sections revealed extensive necrosis in the gC1qR/p32 knockdown compared to control tumors (FIG. 9C). Some necrosis was evident even in small gC1qR/p32 knockdown tumors, indicating that necrosis is an early event in tumors produced by gC1qR/p32-deficient cells. Taken together these data establish an important role for gC1qR/p32 in tumor growth and maintenance.

iii. Discussion

It is herein shown that a mitochondrial/cell surface protein, p32/gC1qR, is the receptor for a tumor-homing peptide, LyP-1, which specifically recognizes an epitope in tumor lymphatics and tumor cells in certain cancers. It is shown that knocking down gC1qR/p32 expression with shRNA elevates glycolysis, decreases mitochondrial respiration, and reduces tumorigenicity in MDA-MB-435 tumor cells. As the expression of gC1qR/p32 is frequently up-regulated in experimental and human cancers, the results show that elevated glycolysis (the Warburg effect) is not necessarily advantageous to tumor growth.

Several lines of evidence show that the LyP-1 peptide specifically binds a protein known as gC1qR/p32 or the receptor for the C1q component of the complement, gC1qR/p32. First, LyP-1 phage binds purified gC1qR/p32 protein and the interaction was inhibited by an antibody directed against the N-terminus of gC1qR/p32. Second, endogenous expression levels and cell surface localization of gC1qR/p32 correlated with the ability of different cell lines to bind LyP-1. Third, overexpression of gC1qR/p32 enhanced and RNAi silencing decreased LyP-1 binding to cells. Finally, intravenously injected FITC-LyP-1 peptide homed in vivo to the areas in tumors where gC1qR/p32 expression was high. The identification of gC1qR/p32 as the LyP-1 receptor prompted the further study of the expression and role of gC1qR/p32 in cancer.

The gC1qR/p32 protein is primarily mitochondrial, but it can be found in the cytoplasm, nuclei, and most importantly for the LyP-1 binding, at the cell surface (Ghebrehiwet et al., 1994; Guo et al., 1999; Peerschke et al., 1994). Several other mitochondrial proteins are also found in extra-mitochondrial locations (Soltys and Gupta, 1999). For example, the mitochondrial chaperone proteins HSP60 and HSP70 have also been observed at the cell surface (Soltys and Gupta, 1997) and endoplasmic reticulum (Singh et al., 1997; Soltys and Gupta, 1996). HSP60 found at the surface of tumor cells and stressed cells (Kaur et al., 1993; Xu et al., 1994) can function as a chaperone for certain proteins (Khan et al., 1998). Interestingly, a chaperone-like function has also been suggested for gC1qR/p32 (Hirasawa et al., 2001; Kittlesen et al., 2000; Robles-Flores et al., 2002; Rozanov et al., 2002b; Schaerer et al., 2001; Storz et al., 2000). FACS data corroborate the earlier findings on the cell surface localization of gC1qR/p32 and indicate that the tumor microenvironment may enhance the cell surface expression of gC1qR/p32.

The amount of gC1qR/p32 at the surface did not necessarily correlate with the total amount of gC1qR/p32 in the cell, showing that the localization is separately controlled. Interestingly, two ubiquitous intracellular proteins, nucleolin (Christian et al., 2003) and annexin 1 (Oh et al., 2004) have been shown to be aberrantly expressed at the cell surface in tumor blood vessels, where they serve as specific markers of angiogenesis. The expression of gC1qR/p32 in tissues is much more restricted than that of nucleolin or annexin 1, but its cell surface expression may add a further degree of tumor specificity, as the LyP-1 peptide (Laakkonen et al., 2004; Laakkonen et al., 2002) and anti-gC1qR/p32 (this study) are strikingly specific in their tumor accumulation upon systemic administration.

Antibody staining of tissue sections with anti-gC1qR/p32 antibody, and intravenously injected anti-gC1qR/p32, confirmed the previously reported association of LyP-1 with specific areas in tumors. Similar to the LyP-1 peptide (Laakkonen et al., 2004; Laakkonen et al., 2002), the antibody outlined two main locations within tumors: cell clusters in areas that were rich in lymphatics, but sparsely populated with blood vessels, and vessel-like structures that apparently represent lymphatics. Bone marrow-derived macrophages that contribute to lymphagiogenesis have been described (Kerjaschki et al., 2006; Maruyama et al., 2007; Maruyama et al., 2005), and it was found that a significant number of intensely gC1qR/p32-positive cells within tumors were also positive for macrophage markers. It was hypothesized that the LyP-1/anti-gC1qR/p32-positive cells represent a rare macrophage population that can serve as a precursor to lymphatic endothelial cells.

The findings with shRNA-mediated knockdown of gC1qR/p32 show an important role of gC1qR/p32 in tumor cells. In vitro, the knockdown resulted in a striking increase in the utilization of the glycolytic pathway of glucose metabolism by tumor cells. These metabolic changes are similar to those caused by mutations that disable the gC1qR/p32 homologue in yeast (Muta et al., 1997). The gC1qR/p32 knockdown was also associated with impaired cell growth, increased cell death, and compromised tumorigenicity. These changes were specifically caused by the knockdown, as an shRNA-resistant gC1qR/p32 construct reversed them.

It was found that breast cancers and some other adenocarcinomas up-regulate gC1qR/p32, but some other cancers, notably prostate cancers, do not express gC1qR/p32 at detectable levels. The mouse and human genomes appear to contain only one gC1qR/p32-related gene, making it unlikely that a related gene would serve in the same role in tumors that lack gC1qR/p32. Interestingly, in contrast to most malignancies, a majority of prostate cancers are not highly glycolytic (Effert et al., 1996; Hofer et al., 1999; Liu, 2006). Hence, they may not need the offsetting activity of gC1qR/p32.

One factor that drives the glycolytic response in tumors is the myc oncogene (Shim et al., 1997). It is noteworthy that c-myc changes are common in breast cancers (Blancato et al., 2004; Liao and Dickson, 2000) which exhibit high glycolytic activity (Isidoro et al., 2005). Thus, the role of gC1qR/p32 can be to counteract excessive glycolysis-promoting activities of c-myc, while allowing its tumor-promoting effects to remain intact.

There can also exist a link between mitochondrial metabolism, autophagy and gC1qR/p32. Autophagy is a dynamic process of subcellular degradation. By mobilizing nutrients that result from macromolecular degradation, autophagy acts to buffer metabolic stress in organisms from yeast to mammals (Levine, 2007; Rubinsztein et al., 2007). A role for gC1qR/p32 protein in autophagy has been previously suggested (Sengupta et al., 2004) and recently gC1qR/p32 has been reported to interact with and stabilize the autophagic inducer protein smARF in mitochondria (Reef et al., 2007). Moreover, deletion of the genes for various autophagy-related proteins in yeast resulted in abnormal mitochondrial morphology and lowered oxidative phosphorylation, along with a growth defect (Zhang et al., 2007). This phenocopies observations in tumor cells with knocked down gC1qR/p32, as these cells also displayed altered mitochondria, a shift from oxidative phosphorylation to glycolysis, and poor growth.

Autophagy can act as a tumor suppressor, but it can also enhance tumor growth (Degenhardt et al., 2006; Levine, 2007). The tumor suppressor function can relate to the role of autophagy in removal of sources of oxygen radicals that would cause DNA damage, with the resulting accumulation of mutations that can accelerate tumor progression. The other side of the coin is that autophagy is a survival mechanism for cells under stress. Tumors often outgrow their blood supply, which results in local areas of hypoxia and nutrient depletion; turning on autophagy provide a cannibalistic mechanism for survival under such stress.

These results agree well with the assumption that gC1qR/p32 expression is involved in the autophagy response. First, the LyP-1 peptide accumulated in hypoxic (and presumably also nutrient-deficient) regions in tumors (Laakkonen et al., 2004), and it is demonstrated in the present work with anti-gC1qR/p32 antibodies that these regions preferentially express gC1qR/p32. Second, tumors that lack the autophagy response are prone to necrosis through a process dubbed metabolic catastrophe (Jin et al., 2007). This is exactly what was observed with tumors grown from gC1qR/p32 knockdown cells; these tumors often contained a large necrotic and hemorrhagic core. Moreover, LyP-1 peptide treatment induced TUNEL-positive lesions in tumors in vivo (Laakkonen et al., 2004), indicating apoptosis or incipient necrosis at these sites.

Given the dual effect of autophagy (and by extension presumably of gC1qR/p32 expression) on tumorigenesis, the question arises as to whether suppressing autophagy would be helpful in treating tumors, or that might be harmful. Partial tumor necrosis resulting from suppression of autophagy is one mechanism that could produce a harmful result, as necrosis causes inflammation, and inflammatory mediators can promote tumor growth (Degenhardt et al., 2006). The results show that necrosis elicited by autophagy suppression can be beneficial as a treatment modality. Extensive necrosis was observed in a majority of the gC1qR/p32 knockdown tumors, yet the tumors grew more slowly than the wild type tumors. The results show that gC1qR/p32 represents a new target for tumor therapy; RNAi, or human monoclonal antibodies and small molecular weight compounds that mimic the LyP-1 peptide, for example, can be used for harnessing this potential.

iv. Experimental Procedures a. Reagents

Mouse monoclonal 60.11 and 74.5.2 anti-gC1qR/p32 antibodies were purchased from Chemicon (Temecula, Calif.). Rat monoclonal anti-mouse CD-31, rat anti-MECA-32, rat anti mouse CD-11b and R-Phycoerythrin (R-PE)-conjugated rat anti-mouse Gr-1 were from BD-PharMingen (San Jose, Calif.), the anti-epithelial membrane antigen (clone E29) was from Chemicon and anti β-actin from Sigma-Aldrich (St. Louis, Mo.). Monoclonal anti-cytochrome c was purchased from BD-PharMingen. Rat anti-podoplanin antibody was kindly provided by Drs. T. Petrova and K. Alitalo (University of Helsinki, Helsinki, Finland). ChromPure Rabbit IgG (whole molecule) was from Jackson ImmunoResearch Laboratories (West Grove, Pa.) and purified Mouse IgG1 (mIgG) from BD-Pharmingen. Purified polyclonal anti-full-length gC1qR/p32 was a generous gift from Dr. B. Ghebrehiwet (Stony Brook University, NY). Polyclonal antibody anti-gC1qR/p32 NH2-terminal antibody was generated in New Zealand White rabbits against a mixture of peptides corresponding to amino acids 76-93 of mouse (TEGDKAFVE-FLTDEIKEE, SEQ ID NO 8) and human (TDGDKAFVD-FLSDEIKEE, SEQ ID NO: 9) gC1qR/p32 protein. The peptides were coupled to keyhole limpet hemocyanin (Pierce, Rockford, Ill.) via a cysteine residue added at their N-termini and the conjugate was used to immunize the rabbits according to instructions of the hemocyanine manufacturer. The antibody was affinity purified on the peptides coupled to Sulfolink Gel (Pierce,) via the N-terminal cysteine. Dr. A. Strongin (Burnham Institute for Medical Research, La Jolla, Calif.) kindly provided human gC1qR/p32 cDNA in pcDNA3.1 Zeo and pET-15b vectors. Oligonucleotide duplexes for transient siRNA knock-down of gC1qR/p32 (C1QBP-HSS101146-47-48 Stealth RNAi) and negative control duplexes (Stealth RNAi control low GC and medium GC) were purchased from Invitrogen (Carlsbad, Calif.). Tissue Arrays (core diameter 0.6 mm) of paraformaldehyde fixed and paraffin-embedded tumor and normal tissue samples were from Applied Phenomics LLC (Tartu, Estonia).

b. Cell Culture and Generation of Stable Cell Lines

MDA-MB-435, C8161, BT549, HL60, and Raji cells were maintained in DMEM containing 4500 mg/ml (25 mM) of glucose (without sodium pyruvate) and supplemented with 10% FBS and 1% Glutamine Pen-Strep (Omega Scientific, Tarzana, Calif.) at 37° C./5% CO2. For experiments in high and low glucose conditions, cells were first adapted for a few days to DMEM (25 mM glucose) supplement with 10% dialized FBS (dFBS; glucose≦5 mg/dl, Invitrogen).

Stable expression of control and gC1qR/p32 shRNA in MDA-MB-435 cells was achieved through the BLOCK-iT Lentiviral RNAi Expression system (Invitrogen). The design of shRNAs sequences complementary to gC1qR/p32 (GeneBank NM_001212) was carried out using Invitrogen's RNAi Designer. The double-stranded oligonucleotides were first cloned into the pENTRTM/U6 vector and tested for gC1qR/p32 silencing by transient transfection. The optimal gC1qR/p32 shRNA sequence (targeting nucleotides 5'-GGATGAG-GTTGGACAAGAAGA-3', SEQ ID NO: 10) was subsequently transferred into the pLenti6/BLOCK-iTTM-DEST vector for lentiviral RNAi production in 293FT cell line according to the manufacturer's instructions. As a control shRNA, we used a two-base-pair mismatched shRNA targeting a different region of gC1qR/p32 cDNA (5'-CCCAATaTCGTGGTTGAtGTTATAA-3', SEQ ID NO 11) lowercase nucleotides indicate the base pair mismatch). MDA-MB-435 cells were transduced with gC1qR/p32 and control RNAi lentiviral stocks. Selection of stably transduced clones was done in medium containing Blasticidin (5 µg/ml, Invitrogen).

To produce a gC1qR/p32 construct resistant to the selected shRNA, the quick Change II site-directed mutagenesis kit (Stratagene; Cedar Creek, Tex.) was used to introduce two silent mutations within the gC1qR/p32 sequence targeted by the shRNA (5'-GGATGAGGTTGGACAgGAgGA-3', SEQ ID NO: 12, lowercase nucleotides indicate silent mutations). The pcDNA3.1Zeo gC1qR/p32 construct was used as a template. The resulting construct was transfected into an MDA-MB-435 cell clone stably expressing the gC1qR/p32 shRNA, and Zeocin (600 µg/ml, Invitrogen) was used to select clones with restored gC1qR/p32 expression.

c. Pull-Down Assays and Mass Spectrometry

Streptavidin agarose beads (Sigma-Aldrich) were resuspended in 2 volumes of phosphate buffer saline (PBS) and conjugated to 3 µg/10 µl beads of biotynilated peptides for 2 h on ice. After incubation, beads were washed three times with PBS/50 mM n-octyl-β-D glucopyranoside (Calbiochem; San Diego, Calif.) to remove free peptides. Cells at 80-90% of confluence were pelleted and lysed in cold PBS/200 mM n-octyl-β-D glucopyranoside and 1% protease inhibitor cocktail (Sigma-Aldrich). The lysate was incubated on ice for 30 min before centrifugation at 14000 rpm for 30 min. An aliquot of the supernatant containing 1 mg of protein was pre-cleared with 40 µl of streptavidin beads for 2 h at 4° C. and subsequently incubated with streptavidin beads loaded with biotinylated peptides over night at 4° C. After 6 washes with PBS/50 mM n-octyl-β-D glucopyranoside, the beads were boiled for 5 min in 40 µl of SDS-PAGE-loading buffer, and the eluted material was separated on a 4-20% polyacrylamide gel and visualized by silver staining (Invitrogen). Bands that appeared in the LyP-1 but not control peptide pull down were cut out, digested with trypsin, and the resulting peptides were analyzed by matrix-assisted laser desorption ionization-time of flight (MALDI-TOF) mass spectrometry. The information was queried against a protein sequence data via Profound software.

d. In Vitro Phage Binding Assays

Microtiter wells (Costar, Corning, N.Y.) were coated overnight at 4° C. with 5 µg/ml of either purified gC1qR/p32 or BSA (Sigma-Aldrich) in 100 µl/well of carbonate buffer (15 mM sodium carbonate, 35 mM sodium bicarbonate). Wells were washed three times with TBS and blocked with Pierce Superblock buffer according to the manufactures instructions. 108 pfu of LyP-1 and control phages were added to the wells in 100 µl/well of TBS/0.05% tween-20 and incubated for 16 h at 37° C. After 6 washes in TBS/0.05% tween-20, bound phages were eluted with 200 µl of Tris-HCl 1M pH 7.5/0.5% SDS for 30 min and subsequently quantified by plaque assay. For inhibition of phage binding by anti gC1qR/p32 antibodies the assay was performed as described above with the difference that 1.5×107 pfu of LyP-1 or insertless phages were allowed to bind for 6 h at 37° C. to gC1qR/p32 protein in the presence of 20 µg/ml of mAb anti gC1qR/p32 antibodies or mIgG. When the assay was performed with cells, 2×106 Raji cells were resuspended in 500 µl of PBS/1% BSA and pre-incubated for 1 h at 4° C. with 40 µg/ml of mAb anti gC1qR/p32 antibodies or mIgG. 108 pfu of insertless or LyP-1 phages were subsequently added to the cells and incubated at 4° C. for 3 h. Cells were washed 5 times with PBS/1% BSA and bound phages were quantified by plaque assay.

e. Immunoblotting and Immunohistology

Cells grown in tissue culture plates were rinsed with PBS and lyzed with NET buffer 1% NP40 (150 mM NaCl, 50 mM Tris-Hcl pH 7.5, 5 mM EDTA pH 8, 1% NP40) containing complete protease inhibitor cocktail. Unbound material was removed by centrifugation at 14,000 rpm for 20 min. Protein concentration of the supernatant was determined by Bio-Rad protein assay. To prepare tumor lysates, tumors were removed, minced, and dissociated in DMEM (1:4 weight to volume) supplemented with 1 mg/ml collagenase (Sigma-Aldrich) for 30 min at 37° C. The cell suspension was centrifuged at 1000 rpm for 5 min and the cell pellet was washed 3 times with PBS/1% BSA prior to lysis in NET buffer containing 1% NP40. An aliquot of each lysate containing equivalent amounts of protein was separated by SDS-PAGE on 4-20% gradient gels and proteins were transferred to nitrocellulose membrane (Invitrogen). Immunoblots were prepared with 1 µg/ml of primary antibodies 60.11 monoclonal anti-gC1qR/p32, polyclonal anti-gC1qR/p32 and anti-β-actin and goat anti-rabbit or rabbit anti-mouse IgG-HRP (diluted 1:1000, Dako Cytomation; Carpinteria, Calif.). The blots were developed using SuperSignal West Pico Chemiluminescent Substrate (Pierce, Rockford, Ill.).

Immunohistochemical staining of frozen tissue sections was carried out using acetone fixation and reagents from Molecular Probes (Invitrogen). The secondary antibodies were: AlexaFluor-594 goat anti-rat or rabbit IgG, AlexaFluor-488 goat anti rabbit IgG. The slides were washed with PBS, incubated for 5 min with DAPI (1 µg/ml) and mounted with ProLong Gold anti-fade reagent. Cytochrome c and gC1qR/p32 were detected in cultured cells fixed in 4% PFA for 20 min at room temperature, followed by permeabilization with 0.2% Triton-X-100 in PBS for 5 min. Paraffin-embedded normal and malignant human tissue array sections were deparaffinized and then treated with Target Retrieval Solution (Dako-Cytometion). The tissue array sections were stained as described above, except gC1qR/p32 and epithelial membrane antigen, which were detected with biotinylated anti-mouse IgG and Vectastain ABC kit (Vector Laboratories Inc, Burlingame, Calif.). To prevent non-specific staining due to endogenous biotin, sections were treated with DAKO Biotin Blocking system prior to antibody incubation.

f. FACS Analysis

Cultured cells were detached with cell enzyme-free dissociation buffer (Gibco/Invitrogen) and collected in PBS containing 1% BSA (PBSB). Single cells suspensions from tumors were obtained as indicated above. For FACS staining, 2.5×105 cells were resuspended in 100 µl of PBSB and incubated with polyclonal anti-full-length gC1qR/p32 or rabbit IgG (20 µg/ml) in PBSB for 30 min at 4° C. The cells were washed in PBSB and stained with goat anti rabbit Alexa 488 (2.5 µg/ml) for 30 min at 4° C. For FACS analysis of bound FITC-peptides, cultured cells were detached as above and incubated with 10 µM of FITC-peptides in 10% FCS/DMEM for 1 hour at 4° C. After washes with PBSB, the cells were resuspended in PBS containing 2 µg/ml of propidium iodide (PI, Molecular Probes/Invitrogen) to distinguish between live and dead cells, and 10,000 cells per sample were analyzed using a BD Biosciences FACSort.

g. Quantification of Growth Rates and Cell Death

MDA-MB-435 clones were seeded in DMEM (25 mM glucose)/10% dialyzed FBS in duplicate at a density of 2.5× 104 cells per well in 12-well plates and allowed to adhere overnight. The medium was removed by washing and substituted with glucose-free DMEM supplement with 10% dialyzed FBS and either 25 or 2.5 mM glucose (Mediatech, Inc., Herndon, Va.). The absolute cell count in each well at each time point was quantified by flow cytometry using CountBright absolute counting beads (Molecular Probes/Invitrogen). For cell death quantification, cells were grown for 3 days in either 25, 2.5, or 0.5 mM glucose, and the Annexin V-FITC kit from BioVision (Mountain View, Calif.) was used to quantify dead cells by flow cytometry.

h. Quantification of Lactate Production and Glucose Consumption

The amount of lactate present in the culture media was determined by generally following the Sigma Diagnostic procedure No 836-UV. All the components were purchased separately from Sigma. Nicotinamide adenine dinucleotide (10 mg) was dissolved in 2 ml glycine buffer, 4 ml of water and 100 µl lactate dehydrogenase (1000 U/ml). In a 96-well plate, 5 µl of media sample was added to 145 µl of the enzyme mixture and incubated at room temperature for 30 min. Increased absorbance at 340 nm due to NADH production was used as measure of lactate originally present in the media. Lactate production/well at a given time point (Tx) was determined from: (A340 nm of cells media at Tx—A340 nm of media only [To]) divided by cell number at Tx. The amount of glucose present in the media was determined using the Glucose Assay Kit (K606-100) from BioVision. Glucose consumption/well was calculated as: (nmol glucose in media only (To)—nmol glucose in cell media at Tx) divided by cell number at Tx.

i. Measurement of Cellular ATP

Cellular ATP levels were determined by a luciferin-luciferase-based assay using the ATP Bioluminescence Assay Kit CLS II (Roche; city, state). Cells (2.5×106) were seeded in 6-well plates in DMEM (25 mM glucose)/10% dFCS. The day after cells were washed, and fresh medium containing 25 or 2.5 mM glucose was added. Four days later, the cells were lysed in 300 µl of NET buffer containing 1% NP40. Supernatants were diluted 4 times in 100 mM Tris, 4 mM EDTA, pH 7.75, and 50 µl samples were assayed with 50 µl of luciferase reagent in duplicate on a Spectra Max Gemini plate reader. The light signal was integrated for 10 s after a delay of 1 s. The bioluminescence units were normalized for the protein concentration determined by Bio-Rad protein assay (Bio-Rad Laboratories, Hercules, Calif.).

j. Quantification of Oxygen Consumption

Oxygen consumption rates of cells in culture were measured using the BD Oxygen Biosensor Systems (OBS) from BD Bioscience. Triplicate samples of 12,000 cells seeded onto 96-well OBS plates in final media volume of 200 µl were used for the measurement. The number of cells at each time point was determined using CountBright absolute counting beads by sampling cells seeded onto side-by-side plates. Fluorescence was measured every 24 h on a Spectra Max Gemini plate reader (excitation 485 nm and emission 630 nm) using the bottom plate reading configuration. Each measurement was normalized by factoring in a blank reading from the same well prior to the addition of the cells and the number of cells in the well at the time of the measurement (Guarino et al., 2004).

k. Mice and Tumors

To produce tumors, BALB/c nude mice were orthotopically injected into the mammary fat pad with 2×106 MDA- MB-435 cells/100 μl of PBS. All animal experimentation received approval from the Animal Research Committee of Burnham Institute for Medical Research. The sizes of tumors were monitored and measured every three days. For in vivo BrdU labeling of tumor cells, tumor-bearing mice were intraperitoneally injected with 1 mg of BrdU (Sigma-Aldrich). The mice were sacrificed 24 h later, and the tumors were removed and fixed in Bouin's solution (Ricca Chemical Company, Arlington, Tex.) for 72 h prior to processing for paraffin embedding.

TABLE 1

Immuno-score of gC1qR/p32 expression in malignant and normal tissues. I = staining intensity (scale 1-3), % = percentage of tumor cells (EMA positive) with a given gC1qR/p32 intensity of staining (scale 0-100). IS = immuno-score: I × % (scale 0-300). NT (non-tumor) was used to indicate samples were tumor cells were not identified.

| CARCINOMA | TYPE | Score | 1 | 2 | 3 | 4 | 5 | 6 | 7 | 8 | 9 | 10 | 11 |
|---|---|---|---|---|---|---|---|---|---|---|---|---|---|
| Breast | Ductal | I | 1 | 1.5 | 2.5 | 1 | 1 | 1.5 | 1 | 1 | 2 | 1 | 1.5 |
|  |  | % | 60 | 70 | 100 | 60 | 70 | 80 | 50 | 60 | 100 | 60 | 80 |
|  |  | IS | 60 | 105 | 250 | 60 | 70 | 123 | 50 | 60 | 200 | 60 | 120 |
|  | Lobular | I | 2.5 | 2.5 | 0 | 2.5 | 2 |  | 1.5 | 1 |  |  |  |
|  |  | % | 90 | 90 |  | 80 | 100 | NT | 70 | 40 |  |  |  |
|  |  | IS | 225 | 225 | 0 | 200 | 200 |  | 105 | 40 |  |  |  |
|  | Mucinous | I | 1 | 1 |  |  |  |  |  |  |  |  |  |
|  |  | % | 60 | 20 |  |  |  |  |  |  |  |  |  |
|  |  | IS | 60 | 20 |  |  |  |  |  |  |  |  |  |
| Endometroid | Adenocarcinoma | I | 2 | 1.5 | 1.5 | 3 | 1 |  |  |  |  |  |  |
|  |  | % | 60 | 90 | 100 | 90 | 90 |  |  |  |  |  |  |
|  |  | IS | 120 | 135 | 150 | 270 | 90 |  |  |  |  |  |  |
| Ovarial | Adenocarcinoma | I | 1.5 | 1 | 1 | 1 | 1 |  |  |  |  |  |  |
|  |  | % | 50 | 15 | 10 | 40 | 30 |  |  |  |  |  |  |
|  |  | IS | 75 | 15 | 10 | 40 | 30 |  |  |  |  |  |  |
| Colon | Adenocarcinoma | I | 2.5 | 2 | 2.5 | 3 | 2 |  |  |  |  |  |  |
|  |  | % | 100 | 40 | 100 | 80 | 90 |  |  |  |  |  |  |
|  |  | IS | 250 | 80 | 250 | 240 | 180 |  |  |  |  |  |  |
| Stomac | Adenocarcinoma | I | 2 | 2 |  | 3 | 3 |  |  |  |  |  |  |
|  |  | % | 70 | 90 | NT | 100 | 100 |  |  |  |  |  |  |
|  |  | IS | 140 | 180 |  | 300 | 300 |  |  |  |  |  |  |
| Pancreas |  | I | $1_{(NT\ islet)}$ | $2.5_{(NT)}$ |  | 2 | 0 |  |  |  |  |  |  |
|  |  | % | 40 | 80 | NT | 90 |  |  |  |  |  |  |  |
|  |  | IS | 40 | 200 |  | 180 | 0 |  |  |  |  |  |  |
| Kidney | Clear cells | I | 1.5 | 1.5 | 2 | 2 | 1 |  |  |  |  |  |  |
|  | carcinoma | % | 90 | 70 | 70 | 80 | 10 |  |  |  |  |  |  |
|  |  | IS | 135 | 105 | 140 | 160 | 10 |  |  |  |  |  |  |
| Melanoma | Skin | I | 2.5 | 2 |  |  |  |  |  |  |  |  |  |
|  |  | % | 80 | 40 |  |  |  |  |  |  |  |  |  |
|  |  | IS | 200 | 80 |  |  |  |  |  |  |  |  |  |
|  | Metastasis | I | 2 | 1.5 |  |  |  |  |  |  |  |  |  |
|  |  | % | 70 | 30 |  |  |  |  |  |  |  |  |  |
|  |  | IS | 140 | 45 |  |  |  |  |  |  |  |  |  |
| Liver |  | I | 0 |  |  |  |  |  |  |  |  |  |  |
|  |  | % |  |  |  |  |  |  |  |  |  |  |  |
|  |  | IS | 0 |  |  |  |  |  |  |  |  |  |  |
| Testis |  | I | 3 | 3 | 3 |  |  |  |  |  |  |  |  |
|  |  | % | 100 | 100 | 90 |  |  |  |  |  |  |  |  |
|  |  | IS | 300 | 300 | 270 |  |  |  |  |  |  |  |  |
| Lung | Squamous cells | I | 2.5 | $1_{(necr)}$ | $1_{(necr)}$ |  |  |  |  |  |  |  |  |
|  |  | % | 50 | 15 | 10 | NT |  |  |  |  |  |  |  |
|  |  | IS | 125 | 15 | 10 |  |  |  |  |  |  |  |  |
| Sarcoma |  | I | $0_{(necr)}$ |  |  |  |  |  |  |  |  |  |  |
|  |  | % |  |  |  |  |  |  |  |  |  |  |  |
|  |  | IS | 0 |  |  |  |  |  |  |  |  |  |  |
| Glioblastoma |  | I | 1 | 1 | 1 |  |  |  |  |  |  |  |  |
|  |  | % | 30 | 30 | 20 |  |  |  |  |  |  |  |  |
|  |  | IS | 30 | 30 | 20 |  |  |  |  |  |  |  |  |
| Spleen | Histiocytoma | I | 1.5 |  |  |  |  |  |  |  |  |  |  |
|  |  | % | 80 |  |  |  |  |  |  |  |  |  |  |
|  |  | IS | 120 |  |  |  |  |  |  |  |  |  |  |
| Prostate |  | I | 0 | $0_{(stroma\ 2+)}$ | 1 | $0_{(stroma+)}$ | $3_{(stroma+)}$ | $0_{(stroma+)}$ | 0 | 0 | 1.5 |  |  |
|  |  | % |  |  | 10 |  | 10 |  |  |  | 15 |  |  |
|  |  | IS | 0 | 0 | 10 | 0 | 30 | 0 | 0 | 0 | 22.5 |  |  |
| Bladder |  | I | 1 |  |  |  |  |  |  |  |  |  |  |
|  |  | % | 10 |  |  |  |  |  |  |  |  |  |  |
|  |  | IS | 10 |  |  |  |  |  |  |  |  |  |  |

| NORMAL TISSUE | INTENSITY | TYPE OF CELLS POSITIVE |
|---|---|---|
| frontal lobe (gray matter) | 1-2+ | microglia |
| frontal lobe (white matter) | 1-2+ | microglia |
| cerebellum (cortex) | 1+ | Purkinje cells |
| Peripheral nerve | – | |
| Adrenal gland | 2+ | cortex |
| Liver | 1-2+ | |
| Pancreas | 3+ | |
| Ovary | – | |
| Testis | +/– | gonia cells |
| | 2+ | Leydig cells |
| Thyroid | 1-2+ | epithelium |
| Spleen | +/– + | small lymphocytes |
| Lung | 2+/3+ | macrophages |
| Myocard | 1+ | |
| Aorta | +/– | |
| Salivary gland | 1+/2+ | |
| Liver | 1/2+ | |
| Esophagus | 1+ | Musc. Mucosa |
| Stomac (antrum) | 1-2+ | |
| Small intestine (Ileum) | 3+ | |
| Cecum | 1+ | ! no epithelium, sm muscle |
| Kidney (cortex) | 2-3+ | distal ducts |
| Kidney (medulla) | 2+/3+ | |
| Bladder | +/– | ! no epithelium, sm muscle |
| Uterus | – | |
| Oviduct | 3+ | Epithelium |
| Prostate | 2-3+ | |
| Skeletal muscle | +/– | |
| Skin | – | Dermis |
| | 1+ | Epidermis |
| Lymph node | | ! Not considered: smoker |
| Adipose tissue | – | |
| Ependymis | – | |
| Tongue | +/– | |
| Thymus | – | stroma |
| | +/– | Hassal bodies |
| Placenta | 1-2+ | |
| Fetal membranes | – | |
| Umbilical cord | – | |

REFERENCES

Alirol, E., and Martinou, J. C. (2006). Mitochondria and cancer: is there a morphological connection? Oncogene 25, 4706-4716.

Alitalo, K., Mohla, S., and Ruoslahti, E. (2004). Lymphangiogenesis and cancer: meeting report. Cancer Res 64, 9225-9229.

Arap, W., Haedicke, W., Bernasconi, M., Kain, R., Rajotte, D., Krajewski, S., Ellerby, H. M., Bredesen, D. E., Pasqualini, R., and Ruoslahti, E. (2002). Targeting the prostate for destruction through a vascular address. Proc Natl Acad Sci USA 99, 1527-1531.

Arap, W., Pasqualini, R., and Ruoslahti, E. (1998a). Cancer treatment by targeted drug delivery to tumor vasculature in a mouse model. Science 279, 377-380.

Arap, W., Pasqualini, R., and Ruoslahti, E. (1998b). Chemotherapy targeted to tumor vasculature. Curr Opin Oncol 10, 560-565.

Blancato, J., Singh, B., Liu, A., Liao, D. J., and Dickson, R. B. (2004). Correlation of amplification and overexpression of the c-myc oncogene in high-grade breast cancer: FISH, in situ hybridisation and immunohistochemical analyses. Br J Cancer 90, 1612-1619.

Braun, L., Ghebrehiwet, B., and Cossart, P. (2000). gC1q-R/p32, a C1q-binding protein, is a receptor for the InlB invasion protein of Listeria monocytogenes. Embo J 19, 1458-1466.

Christian, S., Pilch, J., Akerman, M. E., Porkka, K., Laakkonen, P., and Ruoslahti, E. (2003). Nucleolin expressed at the cell surface is a marker of endothelial cells in angiogenic blood vessels. J Cell Biol 163, 871-878.

Deb, T. B., and Datta, K. (1996). Molecular cloning of human fibroblast hyaluronic acid-binding protein confirms its identity with P-32, a protein co-purified with splicing factor SF2. Hyaluronic acid-binding protein as P-32 protein, co-purified with splicing factor SF2. J Biol Chem 271, 2206-2212.

Dedio, J., Jahnen-Dechent, W., Bachmann, M., and Muller-Esterl, W. (1998). The multiligand-binding protein gC1qR, putative C1q receptor, is a mitochondrial protein. J Immunol 160, 3534-3542.

Degenhardt, K., Mathew, R., Beaudoin, B., Bray, K., Anderson, D., Chen, G., Mukherjee, C., Shi, Y., Gelinas, C., Fan, Y., et al. (2006). Autophagy promotes tumor cell survival and restricts necrosis, inflammation, and tumorigenesis. Cancer Cell 10, 51-64.

Effert, P. J., Bares, R., Handt, S., Wolff, J. M., Bull, U., and Jakse, G. (1996). Metabolic imaging of untreated prostate cancer by positron emission tomography with 18fluorine-labeled deoxyglucose. J Urol 155, 994-998.

Fantin, V. R., St-Pierre, J., and Leder, P. (2006). Attenuation of LDH-A expression uncovers a link between glycolysis, mitochondrial physiology, and tumor maintenance. Cancer Cell 9, 425-434.

Garber, K. (2006). Energy deregulation: licensing tumors to grow. Science 312, 1158-1159.

Ghebrehiwet, B., Jesty, J., and Peerschke, E. I. (2002). gC1q-R/p33: structure-function predictions from the crystal structure. Immunobiology 205, 421-432.

Ghebrehiwet, B., Lim, B. L., Peerschke, E. I., Willis, A. C., and Reid, K. B. (1994). Isolation, cDNA cloning, and overexpression of a 33-kD cell surface glycoprotein that binds to the globular "heads" of C1q. J Exp Med 179, 1809-1821.

Ghosh, I., Chowdhury, A. R., Rajeswari, M. R., and Datta, K. (2004). Differential expression of Hyaluronic Acid Binding Protein 1 (HABP1)/P32/C1QBP during progression of epidermal carcinoma. Mol Cell Biochem 267, 133-139.

Guarino, R. D., Dike, L. E., Haq, T. A., Rowley, J. A., Pitner, J. B., and Timmins, M. R. (2004). Method for determining oxygen consumption rates of static cultures from microplate measurements of pericellular dissolved oxygen concentration. Biotechnol Bioeng 86, 775-787.

Guo, W. X., Ghebrehiwet, B., Weksler, B., Schweitzer, K., and Peerschke, E. I. (1999). Up-regulation of endothelial cell binding proteins/receptors for complement component C1q by inflammatory cytokines. J Lab Clin Med 133, 541-550.

Gupta, S., Batchu, R. B., and Datta, K. (1991). Purification, partial characterization of rat kidney hyaluronic acid binding protein and its localization on the cell surface. Eur J Cell Biol 56, 58-67.

Herwald, H., Dedio, J., Kellner, R., Loos, M., and Muller-Esterl, W. (1996). Isolation and characterization of the kininogen-binding protein p33 from endothelial cells. Identity with the gC1q receptor. J Biol Chem 271, 13040-13047.

Hirasawa, A., Awaji, T., Xu, Z., Shinoura, H., and Tsujimoto, G. (2001). Regulation of subcellular localization of alpha1-adrenoceptor subtypes. Life Sci 68, 2259-2267.

Hofer, C., Laubenbacher, C., Block, T., Breul, J., Hartung, R., and Schwaiger, M. (1999). Fluorine-18-fluorodeoxyglucose positron emission tomography is useless for the detection of local recurrence after radical prostatectomy. Eur Urol 36, 31-35.

Hoffman, J. A., Giraudo, E., Singh, M., Zhang, L., Inoue, M., Porkka, K., Hanahan, D., and Ruoslahti, E. (2003). Progressive vascular changes in a transgenic mouse model of squamous cell carcinoma. Cancer Cell 4, 383-391.

Inoki, K., Zhu, T., and Guan, K. L. (2003). TSC2 mediates cellular energy response to control cell growth and survival. Cell 115, 577-590.

Isidoro, A., Casado, E., Redondo, A., Acebo, P., Espinosa, E., Alonso, A. M., Cejas, P., Hardisson, D., Fresno Vara, J. A., Belda-Iniesta, C., et al. (2005). Breast carcinomas fulfill the Warburg hypothesis and provide metabolic markers of cancer prognosis. Carcinogenesis 26, 2095-2104.

Jain, R. K. (1998). The next frontier of molecular medicine: delivery of therapeutics. Nat Med 4, 655-657.

Jiang, J., Zhang, Y., Krainer, A. R., and Xu, R. M. (1999). Crystal structure of human p32, a doughnut-shaped acidic mitochondrial matrix protein. Proc Natl Acad Sci USA 96, 3572-3577.

Jin, S., DiPaola, R. S., Mathew, R., and White, E. (2007). Metabolic catastrophe as a means to cancer cell death. J Cell Sci 120, 379-383.

Jones, R. G., Plas, D. R., Kubek, S., Buzzai, M., Mu, J., Xu, Y., Birnbaum, M. J., and Thompson, C. B. (2005). AMP-activated protein kinase induces a p53-dependent metabolic checkpoint. Mol Cell 18, 283-293.

Joseph, K., Ghebrehiwet, B., Peerschke, E. I., Reid, K. B., and Kaplan, A. P. (1996). Identification of the zinc-dependent endothelial cell binding protein for high molecular weight kininogen and factor XII: identity with the receptor that binds to the globular "heads" of C1q (gC1q-R). Proc Natl Acad Sci USA 93, 8552-8557.

Joyce, J. A., Laakkonen, P., Bernasconi, M., Bergers, G., Ruoslahti, E., and Hanahan, D. (2003). Stage-specific vascular markers revealed by phage display in a mouse model of pancreatic islet tumorigenesis. Cancer Cell 4, 393-403.

Kaur, I., Voss, S. D., Gupta, R. S., Schell, K., Fisch, P., and Sondel, P. M. (1993). Human peripheral gamma delta T cells recognize hsp60 molecules on Daudi Burkitt's lymphoma cells. J Immunol 150, 2046-2055.

Kerjaschki, D. (2005). The crucial role of macrophages in lymphangiogenesis. J Clin Invest 115, 2316-2319.

Kerjaschki, D., Huttary, N., Raab, I., Regele, H., Bojarski-Nagy, K., Bartel, G., Krober, S. M., Greinix, H., Rosenmaier, A., Karlhofer, F., et al. (2006). Lymphatic endothelial progenitor cells contribute to de novo lymphangiogenesis in human renal transplants. Nat Med 12, 230-234.

Khan, I. U., Wallin, R., Gupta, R. S., and Kammer, G. M. (1998). Protein kinase A-catalyzed phosphorylation of heat shock protein 60 chaperone regulates its attachment to histone 2B in the T lymphocyte plasma membrane. Proc Natl Acad Sci USA 95, 10425-10430.

Kittlesen, D. J., Chianese-Bullock, K. A., Yao, Z. Q., Braciale, T. J., and Hahn, Y. S. (2000). Interaction between complement receptor gC1qR and hepatitis C virus core protein inhibits T-lymphocyte proliferation. J Clin Invest 106, 1239-1249.

Krainer, A. R., Mayeda, A., Kozak, D., and Binns, G. (1991). Functional expression of cloned human splicing factor SF2: homology to RNA-binding proteins, U1 70K, and Drosophila splicing regulators. Cell 66, 383-394.

Laakkonen, P., Akerman, M. E., Biliran, H., Yang, M., Ferrer, F., Karpanen, T., Hoffman, R. M., and Ruoslahti, E. (2004). Antitumor activity of a homing peptide that targets tumor lymphatics and tumor cells. Proc Natl Acad Sci USA 101, 9381-9386.

Laakkonen, P., Porkka, K., Hoffman, J. A., and Ruoslahti, E. (2002). A tumor-homing peptide with a targeting specificity related to lymphatic vessels. Nat Med 8, 751-755.

Lee, S. M., Lee, E. J., Hong, H. Y., Kwon, M. K., Kwon, T. H., Choi, J. Y., Park, R. W., Kwon, T. G., Yoo, E. S., Yoon, G. S., et al. (2007). Targeting bladder tumor cells in vivo and in the urine with a peptide identified by phage display. Mol Cancer Res 5, 11-19.

Levine, B. (2007). Cell biology: autophagy and cancer. Nature 446, 745-747.

Liao, D. J., and Dickson, R. B. (2000). c-Myc in breast cancer. Endocr Relat Cancer 7, 143-164.

Lim, B. L., Reid, K. B., Ghebrehiwet, B., Peerschke, E. I., Leigh, L. A., and Preissner, K. T. (1996). The binding protein for globular heads of complement C1q, gC1qR. Functional expression and characterization as a novel vitronectin binding factor. J Biol Chem 271, 26739-26744.

Liu, Y. (2006). Fatty acid oxidation is a dominant bioenergetic pathway in prostate cancer. Prostate Cancer Prostatic Dis 9, 230-234.

Majumdar, M., Meenakshi, J., Goswami, S. K., and Datta, K. (2002). Hyaluronan binding protein 1 (HABP1)/C1QBP/p32 is an endogenous substrate for MAP kinase and is translocated to the nucleus upon mitogenic stimulation. Biochem Biophys Res Commun 291, 829-837.

Maruyama, K., Asai, J., Ii, M., Thorne, T., Losordo, D. W., and D'Amore, P. A. (2007). Decreased macrophage number and activation lead to reduced lymphatic vessel formation and contribute to impaired diabetic wound healing. Am J Pathol 170, 1178-1191.

Maruyama, K., Ii, M., Cursiefen, C., Jackson, D. G., Keino, H., Tomita, M., Van Rooijen, N., Takenaka, H., D'Amore, P. A., Stein-Streilein, J., et al. (2005). Inflammation-induced lymphangiogenesis in the cornea arises from CD11b-positive macrophages. J Clin Invest 115, 2363-2372.

Matthews, D. A., and Russell, W. C. (1998). Adenovirus core protein V interacts with p32—a protein which is associated with both the mitochondria and the nucleus. J Gen Virol 79 (Pt 7), 1677-1685.

Muta, T., Kang, D., Kitajima, S., Fujiwara, T., and Hamasaki, N. (1997). p32 protein, a splicing factor 2-associated protein, is localized in mitochondrial matrix and is functionally important in maintaining oxidative phosphorylation. J Biol Chem 272, 24363-24370.

Oh, P., Li, Y., Yu, J., Durr, E., Krasinska, K. M., Carver, L. A., Testa, J. E., and Schnitzer, J. E. (2004). Subtractive proteomic mapping of the endothelial surface in lung and solid tumours for tissue-specific therapy. Nature 429, 629-635.

Parle-McDermott, A., McWilliam, P., Tighe, O., Dunican, D., and Croke, D. T. (2000). Serial analysis of gene expression identifies putative metastasis-associated transcripts in colon tumour cell lines. Br J Cancer 83, 725-728.

Peerschke, E. I., Reid, K. B., and Ghebrehiwet, B. (1994). Identification of a novel 33-kDa C1q-binding site on human blood platelets. J Immunol 152, 5896-5901.

Porkka, K., Laakkonen, P., Hoffman, J. A., Bemasconi, M., and Ruoslahti, E. (2002). A fragment of the HMGN2 protein homes to the nuclei of tumor cells and tumor endothelial cells in vivo. Proc Natl Acad Sci USA 99, 7444-7449.

Reef, S., Shifman, O., Oren, M., and Kimchi, A. (2007). The autophagic inducer smARF interacts with and is stabilized by the mitochondrial p32 protein. Oncogene.

Robles-Flores, M., Rendon-Huerta, E., Gonzalez-Aguilar, H., Mendoza-Hernandez, G., Islas, S., Mendoza, V., Ponce-Castaneda, M. V., Gonzalez-Mariscal, L., and Lopez-Casillas, F. (2002). p32 (gC1qBP) is a general protein kinase C(PKC)-binding protein; interaction and cellular localization of P32-PKC complexes in ray hepatocytes. J Biol Chem 277, 5247-5255.

Rozanov, D. V., Ghebrehiwet, B., Postnova, T. I., Eichinger, A., Deryugina, E. I., and Strongin, A. Y. (2002a). The hemopexin-like C-terminal domain of membrane type 1 matrix metalloproteinase regulates proteolysis of a multifunctional protein, gC1qR. J Biol Chem 277, 9318-9325.

Rozanov, D. V., Ghebrehiwet, B., Ratnikov, B., Monosov, E. Z., Deryugina, E. I., and Strongin, A. Y. (2002b). The cytoplasmic tail peptide sequence of membrane type-1 matrix metalloproteinase (MT1-MMP) directly binds to gC1qR, a compartment-specific chaperone-like regulatory protein. FEBS Lett 527, 51-57.

Rubinstein, D. B., Stortchevoi, A., Boosalis, M., Ashfaq, R., Ghebrehiwet, B., Peerschke, E. I., Calvo, F., and Guillaume, T. (2004). Receptor for the globular heads of C1q (gC1q-R, p33, hyaluronan-binding protein) is preferentially expressed by adenocarcinoma cells. Int J Cancer 110, 741-750.

Rubinsztein, D. C., Gestwicki, J. E., Murphy, L. O., and Klionsky, D. J. (2007). Potential therapeutic applications of autophagy. Nat Rev Drug Discov 6, 304-312.

Ruoslahti, E. (2002). Specialization of tumour vasculature. Nat Rev Cancer 2, 83-90.

Schaerer, M. T., Kannenberg, K., Hunziker, P., Baumann, S. W., and Sigel, E. (2001). Interaction between GABA(A) receptor beta subunits and the multifunctional protein gC1q-R. J Biol Chem 276, 26597-26604.

Schledzewski, K., Falkowski, M., Moldenhauer, G., Metharom, P., Kzhyshkowska, J., Ganss, R., Demory, A., Falkowska-Hansen, B., Kurzen, H., Ugurel, S., et al. (2006). Lymphatic endothelium-specific hyaluronan receptor LYVE-1 is expressed by stabilin-1+, F4/80+, CD11b+ macrophages in malignant tumours and wound healing tissue in vivo and in bone marrow cultures in vitro: implications for the assessment of lymphangiogenesis. J Pathol 209, 67-77.

Sengupta, A., Tyagi, R. K., and Datta, K. (2004). Truncated variants of hyaluronan-binding protein 1 bind hyaluronan and induce identical morphological aberrations in COS-1 cells. Biochem J 380, 837-844.

Shaw, R. J. (2006). Glucose metabolism and cancer. Curr Opin Cell Biol 18, 598-608.

Shim, H., Dolde, C., Lewis, B. C., Wu, C. S., Dang, G., Jungmann, R. A., Dalla-Favera, R., and Dang, C. V. (1997). c-Myc transactivation of LDH-A: implications for tumor metabolism and growth. Proc Natl Acad Sci USA 94, 6658-6663.

Simberg, D., Duza, T., Park, J. H., Essler, M., Pilch, J., Zhang, L., Derfus, A. M., Yang, M., Hoffman, R. M., Bhatia, S., et al. (2007). Biomimetic amplification of nanoparticle homing to tumors. Proc Natl Acad Sci USA 104, 932-936.

Singh, B., Soltys, B. J., Wu, Z. C., Patel, H. V., Freeman, K. B., and Gupta, R. S. (1997). Cloning and some novel characteristics of mitochondrial Hsp70 from Chinese hamster cells. Exp Cell Res 234, 205-216.

Soltys, B. J., and Gupta, R. S. (1996). Immunoelectron microscopic localization of the 60-kDa heat shock chaperonin protein (Hsp60) in mammalian cells. Exp Cell Res 222, 16-27.

Soltys, B. J., and Gupta, R. S. (1997). Cell surface localization of the 60 kDa heat shock chaperonin protein (hsp60) in mammalian cells. Cell Biol Int 21, 315-320.

Soltys, B. J., and Gupta, R. S. (1999). Mitochondrial-matrix proteins at unexpected locations: are they exported? Trends Biochem Sci 24, 174-177.

Soltys, B. J., Kang, D., and Gupta, R. S. (2000). Localization of P32 protein (gC1q-R) in mitochondria and at specific extramitochondrial locations in normal tissues. Histochem Cell Biol 114, 245-255.

St Croix, B., Rago, C., Velculescu, V., Traverso, G., Romans, K. E., Montgomery, E., Lal, A., Riggins, G. J., Lengauer, C., Vogelstein, B., and Kinzler, K. W. (2000). Genes expressed in human tumor endothelium. Science 289, 1197-1202.

Stacker, S. A., Achen, M. G., Jussila, L., Baldwin, M. E., and Alitalo, K. (2002). Lymphangiogenesis and cancer metastasis. Nat Rev Cancer 2, 573-583.

Storz, P., Hausser, A., Link, G., Dedio, J., Ghebrehiwet, B., Pfizenmaier, K., and Johannes, F. J. (2000). Protein kinase C [micro] is regulated by the multifunctional chaperon protein p32. J Biol Chem 275, 24601-24607.

Tange, T. O., Jensen, T. H., and Kjems, J. (1996). In vitro interaction between human immunodeficiency virus type 1 Rev protein and splicing factor ASF/SF2-associated protein, p32. J Biol Chem 271, 10066-10072.

van Leeuwen, H. C., and O'Hare, P. (2001). Retargeting of the mitochondrial protein p32/gC1Qr to a cytoplasmic compartment and the cell surface. J Cell Sci 114, 2115-2123.

Wallace, D. C. (2005). Mitochondria and cancer: Warburg addressed. Cold Spring Harb Symp Quant Biol 70, 363-374.

Xu, Q., Schett, G., Seitz, C. S., Hu, Y., Gupta, R. S., and Wick, G. (1994). Surface staining and cytotoxic activity of heat-shock protein 60 antibody in stressed aortic endothelial cells. Circ Res 75, 1078-1085.

Zhang, L., Giraudo, E., Hoffman, J. A., Hanahan, D., and Ruoslahti, E. (2006). Lymphatic zip codes in premalignant lesions and tumors. Cancer Res 66, 5696-5706.

Zhang, Y., Qi, H., Taylor, R., Xu, W., Liu, L. F., and Jin, S. (2007). The Role of Autophagy in Mitochondria Maintenance: Characterization of Mitochondrial Functions in Autophagy-Deficient S. cerevisiae Strains. Autophagy 3, 337-346.

We claim:

1. A method, the method comprising:
   a. identifying a subject having cancer cells having an elevated level of gC1q/p32 receptor compared with non-cancerous cells in the subject; and
   b. administering to the subject a composition comprising SEQ ID NO:1.

2. The method of claim 1, wherein the subject has cancer.

3. The method of claim 1, wherein the composition further comprises a moiety.

4. The method of claim 3, wherein the moiety is a therapeutic moiety, a diagnostic agent, or a nanoparticle.

5. The method of claim 4, wherein the therapeutic moiety targets a DNA-associated process.

6. The method of claim 4, wherein the therapeutic moiety is selected from the group consisting of a cytotoxic agent, an alkylating agent, an anti-tumor antibiotic, a sequence-selective agent, an anti-angiogenic agent, cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286.

7. A method of delivering a Lyp-1 composition to a gC1q/p32 receptor, wherein the Lyp-1 composition comprises a moiety linked to a composition comprising SEQ ID NO:1; wherein the method comprises bringing into contact the Lyp-1 composition and a cell, thereby delivering the Lyp-1 composition to the gC1q/p32 receptor, wherein the cell is in a subject, wherein the cell is selected for its potential to comprise a gC1q/p32 receptor by detecting the presence of gC1q/p32 receptor on another cell of the subject.

8. A method, the method comprising:
   a. identifying a subject having cells having an increased level of gC1q/p32 receptor; and
   b. administering to the subject a composition comprising SEQ ID NO:1.

9. The method of claim 8, wherein the cells have an increased number of gC1q/p32 receptors over the normal amount.

10. A method, the method comprising:
    a. identifying a subject having cells having an increased level of gC1q/p32 receptor; and
    b. administering to the subject a composition comprising SEQ ID NO:1;
    wherein the cells have an increased number of gC1q/p32 receptors over the normal amount, wherein the normal amount is the amount of gC1q/p32 receptors in normal cells.

11. The method of claim 8, wherein the cells having an increased level of gC1q/p32 receptor are cancer cells.

12. A method, the method comprising:
    a. identifying a subject having a tumor having an elevated level of gC1q/p32 receptor compared with the corresponding normal tissue; and
    b. administering to the subject a composition comprising SEQ ID NO:1.

13. A method, the method comprising:
    a. identifying a subject having a disease exhibiting an increased level of gC1q/p32 receptor; and
    b. administering to the subject a composition comprising SEQ ID NO:1.

* * * * *